US010066232B2

(12) United States Patent
Brune et al.

(10) Patent No.: US 10,066,232 B2
(45) Date of Patent: Sep. 4, 2018

(54) E. COLI SEPARATOME-BASED PROTEIN EXPRESSION AND PURIFICATION PLATFORM

(71) Applicants:BOARD OF TRUSTEES OF THE UNIVERSITY OF ARKANSAS, Little Rock, AR (US); UNIVERSITY OF PITTSBURGH-OF THE COMMONWEALTH SYSTEM OF HIGHER EDUCATION, Pittsburgh, PA (US)

(72) Inventors: Ellen M. Brune, Little Rock, AR (US); Robert R. Beitle, Jr., Little Rock, AR (US); Mohammad M. Ataai, Pittsburgh, PA (US); Patrick R. Bartlow, Pittsburgh, PA (US); Ralph L. Henry, Little Rock, AR (US)

(73) Assignees: BOARD OF TRUSTEES OF THE UNIVERSITY OF ARKANSAS, Little Rock, AR (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/791,803

(22) Filed: Oct. 24, 2017

(65) Prior Publication Data
US 2018/0073030 A1 Mar. 15, 2018

Related U.S. Application Data

(63) Continuation of application No. 15/022,852, filed as application No. PCT/US2014/056013 on Sep. 17, 2014, now Pat. No. 9,822,371.

(60) Provisional application No. 61/878,882, filed on Sep. 17, 2013.

(51) Int. Cl.
| | |
|---|---|
| *C12P 21/06* | (2006.01) |
| *C12N 9/00* | (2006.01) |
| *C12N 15/70* | (2006.01) |
| *C12P 21/02* | (2006.01) |
| *C12P 21/00* | (2006.01) |
| C12P 21/04 | (2006.01) |
| C12N 1/21 | (2006.01) |

(52) U.S. Cl.
CPC ............... *C12N 15/70* (2013.01); *C12N 9/00* (2013.01); *C12P 21/00* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,989,265 B2 | 1/2006 | Blattner et al. | |
| 7,303,906 B2 | 12/2007 | Blattner et al. | |
| 8,039,243 B2 | 10/2011 | Blattner et al. | |
| 8,043,842 B2 | 10/2011 | Blattner et al. | |
| 8,119,365 B2 | 2/2012 | Blattner et al. | |
| 8,178,339 B2 | 5/2012 | Campbell et al. | |
| 8,697,359 B1 | 4/2014 | Zhang | |
| 8,927,231 B2 | 1/2015 | Brune et al. | |
| 9,816,068 B2 * | 11/2017 | Brune ...................... | C12N 1/20 |
| 9,822,371 B2 * | 11/2017 | Brune ...................... | C12N 15/70 |
| 2005/0136449 A1 | 6/2005 | Hanson et al. | |
| 2009/0075333 A1 | 3/2009 | Campbell et al. | |
| 2009/0075352 A1 | 3/2009 | Lee et al. | |
| 2012/0183995 A1 | 7/2012 | Ferrari et al. | |
| 2012/0219994 A1 | 8/2012 | Blattner et al. | |
| 2015/0139944 A1 | 5/2015 | Brune et al. | |
| 2016/0230177 A1 | 8/2016 | Brune et al. | |

(Continued)

FOREIGN PATENT DOCUMENTS

| | | |
|---|---|---|
| EP | 1483367 B1 | 5/2010 |
| JP | 2007306910 A | 11/2007 |

(Continued)

OTHER PUBLICATIONS

Yu et al. (2002) "Minimization of the *Escherichia coli* genome using a Tn5-targeted Cre/IoxP excision system", Nature Biotechnol. 20:1018-1023.
Asenjo et al. (2004) "Is there a rational method to purify proteins? From expert systems to proteomics", Journal of Molecular Recognition 17:236-247.
Cai et al. (2004) "Genomic Data for Alternate Production Strategies. I. Identification of Major Contaminating Species for Cobalt+2 Immobilized Metal Affinity Chromatography", Biotechnol. Bioeng. 88(1):77-83.

(Continued)

*Primary Examiner* — Nancy J Leith
(74) *Attorney, Agent, or Firm* — Charles E. Cohen

(57) ABSTRACT

Provided is a separatome-based peptide, polypeptide, and protein expression and purification platform based on the juxtaposition of the binding properties of host cell genomic peptides, polypeptides, and proteins with the characteristics and location of the corresponding genes on the host cell chromosome of *E. coli*. The separatome-based protein expression and purification platform quantitatively describes and identifies priority deletions, modifications, or inhibitions of certain gene products to increase chromatographic separation efficiency, defined as an increase in column capacity, column selectivity, or both, with emphasis on the former. Moreover, the separatome-based protein expression and purification platform provides a computerized knowledge tool that, given separatome data and a target recombinant peptide, polypeptide, or protein, intuitively suggests strategies facilitating efficient product purification. The separatome-based protein expression and purification platform is an efficient bioseparation system that intertwines host cell expression systems and chromatography.

19 Claims, 15 Drawing Sheets

Specification includes a Sequence Listing.

(56) References Cited

U.S. PATENT DOCUMENTS

2017/0218422 A1* 8/2017 Brune .................... C12P 19/56

FOREIGN PATENT DOCUMENTS

| WO | 2012033653 A1 | 3/2012 |
| WO | 2013138351 A1 | 9/2013 |

OTHER PUBLICATIONS

Tiwari et al. (2010) "Identification and characterization of native proteins of *Escherichia coli* BL-21 that display affinity towards Immobilized Metal Affinity Chromatography and Hydrophobic Interaction Chromatography Matrices", Protein Expression and Purification 70:191-195.
Liu et al. (2009) "Use of proteomics for design of a tailored host cell for highly efficient protein purification", J. Chromatog. A 1216:2433-2438.
Bartlow et al. (2011a) "Identification of native *Escherichia coli* BL21 (DE3) proteins that bind to immobilized metal affinity chromatography under high imidazole conditions and use of 2D-DIGE to evaluate contamination pools with respect to recombinant protein expression level", Protein Expression and Purification 78:216-224.
Bartlow et al. (2011b) "Evaluation of *Escherichia coli* Proteins that Burden Nonaffinity-Based Chromatography as a Potential Strategy for Improved Purification Performance", American Institute of Chemical Engineers Biotechnol. Prog. 28(1):137-145.
Caparon et al. (2009) "Integrated Solution to Purification Challenges in the Manufacture of a Soluble Recombinant Protein in *E. coli*", Biotechnol. Bioeng. 105(2):239-249.
Conrad et al. (2010) "RNA polymerase mutants found through adaptive evolution reprogram *Escherichia coli* for optimal growth in minimal media", Proc. Natl. Acad. Sci. USA 107(47):20500-20505.
Song et al. (2009) "Bioinformatic Comparison of Bacterial Secretomes", Genomics Proteomics Bioinformatics 7(1-2):37-46.
PCT International Search Report and Written Opinion of the International Searching Authority in PCT/US2013/030549 (dated Aug. 7, 2013).
Brune et al. (Jan. 21, 2013) Cambridge Healthtech Institute (CHI) Oral Abstract entitled "Genetic Engineering of *E. coli* to Facilitate Downstream Purification".
Brune et al. (Jan. 21, 2013) Cambridge Healthtech Institute (CHI) Peptalk Oral Presentation entitled "Genetic Engineering of *E. coli* to Facilitate Downstream Purification".
Brune et al. (Jan. 21, 2013) Cambridge Healthtech Institute (CHI) Peptalk Poster Abstract entitled "Genetic Engineering of *E. coli* to Facilitate Downstream Purification".
Brune et al. (Jan. 21, 2013) Cambridge Healthtech Institute (CHI) Peptalk Poster entitled "Genetic Engineering of *E. coli* to Facilitate Downstream Purification".
Beitle et al. (Oct. 23, 2012) Arkansas Biosciences Institute Oral Presentation entitled "Proteome-driven efficient bioseparation by rewriting the host cell genome".
E. Brune (Oct. 20, 2011) AIChE Annual Meeting Oral Presentation entitled "Proteome-Based Development of Affinity Motifs and Reduced Contaminant Strains".
E. Brune (Dec. 5, 2012) Dept. of Defense Threat Reduction Agency (DTRA) TechWatch Oral Presentation entitled "An *Escherichia coli* platform for biotherapeutics based on robust, separation-friendly strains".
E. Brune (Dec. 5, 2012) Dept. of Defense Threat Reduction Agency (DTRA) Abstract entitled "Development of a recombinant protein expression platform: Simplifying purification through genomic modifications".
Bartlow et al. (Fall, 2008) American Chemical Society Presentation entitled "Design of recombinant strains based on host cell elution profiles".
Bartlow et al. (Nov. 8-13, 2009) AIChE 2009 Annual Fall Scientific Meeting Presentation entitled "Knockout and Mutational Tailoring of Host Strains to Simplify Bioseparation".
Bartlow et al. (Oct. 19, 2011) AIChE Annual Meeting Presentation entitled "Evaluation of *Escherichia coli* Proteins that Burden Recombinant Protein Purification on Inexpensive, Non-Affinity-Based Resins".
Haley et al. (Nov. 2, 2005) AIChE Annual Meeting Abstract entitled "Circumventing the Effects of High Binding Immobilized Metal Affinity Chromatography Contaminants".
Varakala et al. (Nov. 2, 2005) AIChE Annual Meeting Abstract entitled "Improvement Upon Bioseparation by Altering the Host Genome".
Beitle et al. (Nov. 15, 2006) AIChE Annual Meeting Abstract entitled "A Rational Method to Improve Bioseparation Via Proteomics".
Varakala et al. (Nov. 7, 2007) AIChE Annual Meeting Abstract entitled "The Metalloproteome of *Escherichia coli*: Its Application in Downstream Processing Via Imac".
Bartlow et al. (Oct. 19, 2011) AIChE Annual Meeting Abstract entitled "Evaluation of *Escherichia coli* Proteins That Burden Recombinant Protein Purification on Inexpensive, Non-Affinity-Based Resins".
Brune et al (Oct. 20, 2011) AIChE Annual Meeting Abstract entitled "Proteome-Based Development of Affinity Motifs and Reduced Contaminant Strains".
R. Varakala (May 2008) Ph.D. Dissertation, University of Arkansas, entitled "Proteome Based Improvements for Immobilized Metal Affinity Chromatography in an *Escherichia coli* Expression System".
Brune et al. (Mar. 27, 2011) 41st ACS National Meeting & Exposition, Poster Presentation entitled "Novel Affinity Tails, Based on Genomic Data, for Immobilized Metal Affinity and Ion-Exchange Chromatographies".
Brune et al. (Jan. 11, 2011) Cambridge Healthtech Institute (CHI) Peptalk Poster Presentation entitled "Development of Next-Generation Affinity Sequences for Use With Both Immobilized Metal Affinity Chromatography and Ion Exchange Chromatography".
Brune et al. (Mar. 27, 2011) 41st ACS National Meeting & Exposition, Abstract for Poster entitled "Novel Affinity Tails, Based on Genomic Data, for Immobilized Metal Affinity and Ion-Exchange Chromatographies".
Brune et al. (Jan. 11, 2011) Cambridge Healthtech Institute (CHI) Peptalk Abstract for Poster entitled "Development of Next-Generation Affinity Sequences for Use With Both Immobilized Metal Affinity Chromatography and Ion Exchange Chromatography".
Jun-Ichi Kato et al. (2007) "Construction of consecutive deletions of the *Escherichia coli* chromosome", Molecular Systems Biology 3: Article No. 132:1-7.
Jun-Ichi Kato et al. (2008) "Construction of Long Chromosomal Deletion Mutants of *Escherichia coli* and Minizimation of the Genome", Meth. Mol. Biol., vol. 416: Microbial Gene Essentiality, Humana Press, NJ, pp. 279-293.
Hashimoto et al. (2005) "Cell size and nucleoid organization of engineered *Escherichia coli* cells with a reduced genome", Molecular Microbiology 55(1):137-149.
Lee et al. (2005) "Metabolic Engineering of *Escherichia coli* for Enhanced Production of Succinic Acid, Based on Genome Comparison and In Silico Gene Knockout Simulation", Applied and Environmental Microbiology 71 (12):7880-7887.
Ellen M. Brune, Ph.D. Dissertation entitled "Bacterial Strains Based on the Separatome of *Escherichia coli*", May 2013, University of Arkansas.
Patrick R. Bartlow, Ph.D. Dissertation entitled "Design of *Escherichia coli* Host Strains for Improved Recombinant Protein Purification . . . ", Sep. 2011, University of Pittsburgh.
Le Cong et al. (2013) "Multiplex Genome Engineering Using CRISPR/Cas Systems", Science, vol. 339:819-823.
Jiang et al. (2013) "RNA-Guided Editing of Bacterial Genomes Using CRISPR/Cas Systems", Nature Biotechnology, vol. 31(3):233-239.
Mali et al. (2013) "Cas9 As a Versatile Tool for Engineering Biology", Nature Methods, vol. 10(10):957-963.

(56) References Cited

OTHER PUBLICATIONS

Sander et al. (2014) "CRISPR/Cas Systems for Editing, Regulating and Targeting Genomes", Nature Biotechnology, vol. 32(4):347-355.
Amrein et al. (1995) "Purification and characterization of recombinant human p50csk protein-tyrosine kinase from an *Escherichia coli* expression system overproducing the bacterial chaperones GroES and Gro EL", Proceedings of the National Academy of Sciences USA, vol. 92(4):1048-1052.
Shin et al. (2008) "Extracellular Recombinant Protein Production From an *Escherichia coli* lpp Deletion Mutant", Biotechnology and Bioengineering, vol. 101(6):1288-1296.
Posfai et al. (2006) "Emergent Properties of Reduced-Genome *Escherichia coli*", Science, vol. 312:1044-1046.
International Preliminary Report on Patentability dated Mar. 22, 2016 (including Written Opinion dated Dec. 8, 2014 (6 pages total)), and International Search Report dated Dec. 8, 2014, in priority PCT application PCT/US2014/056013.
Morimoto et al. (2008) "Enhanced Recombinant Protein Productivity by Genome Reduction in Bacillus subtilis", DNA Research, vol. 15:73-81.
Communication from the European Patent Office in connection with the examination of European Patent Application Publication No. EP13714069.5, dated Jan. 14, 2016 (6 pages).
Communication from the European Patent Office in connection with the examination of European Patent Application Publication No. EP13714069.5, dated Sep. 7, 2016 (10 pages).
Communication from the European Patent Office in non-counterpart European Patent Application EP14846151.0, dated Mar. 8, 2017 (8 pages total).
Communication from the European Patent Office in counterpart European Patent Application EP13714069.5, dated Mar. 24, 2017 (12 pages total).
Official Action from the Canadian Intellectual Property Office in non-counterpart Canadian Patent Application No. 2,924,650, dated Mar. 31, 2017 (4 pages total).
Notice of Intention to Grant from the European Patent Office in counterpart European Patent Application No. EP14846151.0 (21pages total: 8 pages of Notice; 13 pages of claims), issued Jan. 26, 2018.
Requisition by the Examiner in Accordance With Subsection 30(2) of the Patent Rules, dated Jul. 16, 2018, issued by the Canadian Intellectual Property Office (3 pages total).

* cited by examiner

E. COLI SEPARATOME-BASED PROTEIN EXPRESSION AND PURIFICATION PLATFORM

CROSS-REFERENCE TO RELATED APPLICATIONS

This application is a Continuation of U.S. application Ser. No. 15/022,852, filed Mar. 17, 2016, now U.S. Pat. No. 9,822,371, issued on Nov. 21, 2017; which is a U.S. national stage filing under 35 U.S.C. § 371 of PCT International Application Ser. No. PCT/US2014/056013, filed Sep. 17, 2014; which claims the benefit of priority of U.S. provisional application Ser. No. 61/878,882, filed Sep. 17, 2013. This application claims the benefit of priority of each of the listed prior applications, and the contents of each of these prior applications are herein incorporated by reference in their entirety.

STATEMENT REGARDING FEDERALLY SPONSORED RESEARCH OR DEVELOPMENT AND JOINT RESEARCH AGREEMENT DISQUALIFICATION UNDER THE CREATE ACT (COOPERATIVE RESEARCH AND TECHNOLOGY ENHANCEMENT ACT OF 2004 (CREATE ACT) (PUB. L. 108-453, 118 STAT. 3596 (2004))

This invention was made with government support under grants Nos. 0534836, 0533949, 1237252, 1142101, and 1048911, awarded by the National Science Foundation. The U.S. government has certain rights in the invention.

The present invention was collaboratively made by scientists from the University of Arkansas and the University of Pittsburgh under the above-noted joint NSF grants that were in effect on or before the date the presently claimed invention was made. The claimed invention was made as a result of activities undertaken within the scope of the joint research agreement. The term "joint research agreement" means the joint NSF research grants awarded to the above-noted parties for the performance of experimental, developmental, or research work in the field of the claimed invention.

BACKGROUND

Disclosed herein is a proteomics-based protein expression and purification platform, more particularly a single cell line, or set of cell lines, designed by manipulating the separatomes associated with various separation techniques, in particular column chromatography, that can be used in a wide variety of processes for the expression of recombinantly produced peptides, polypeptides, and proteins, and to the subsequent rapid, efficient, and economical recovery thereof in high yield, thereby eliminating the need to develop individualized host cells for each purification process.

Current society is heavily dependent on mass-manufactured peptides, polypeptides and proteins that are used in everything from cancer treatment medications to laundry detergents. More than 325 million people worldwide have been helped by the over 155 recombinantly produced polypeptides and peptides (drugs and vaccines) currently approved by the United States Food and Drug Administration. In addition, there are more than 370 biotechnology drug products and vaccines ("biologics") currently in clinical trials targeting more than 200 diseases, including various cancers, Alzheimer's disease, heart disease, diabetes, multiple sclerosis, immunodeficiency, and arthritis. Enzymes used in industrial processes claim approximately a 2.7 billion dollar market, with an expected growth to a value of 6 billion dollars by 2016. Of the approximately 3000 industrial enzymes in use today for applications in biotechnology, food, fuel, and pulp and paper industries, about one-third of these are produced in recombinant bacteria.

Manufacturing of therapeutically useful peptides, polypeptides, and proteins has been hampered, in large part, by the limitations of the organisms currently used to express these molecules, and by the often extensive recovery steps necessary as the final product is isolated. Recombinant protein expression is the preferred, predominant method for the manufacture of these pharmaceuticals, herein referred to as "biologics" to differentiate them, in particular, both from chemically synthesized therapeutics (e.g., antihistamines or CNS drugs) and from industrial enzymes such as pectinases or restriction endonucleases, for example. In general, the purification of a biologic to within tolerable limits is the most costly stage of manufacturing and validation, with the burden of regulation placed upon it by the Food and Drug Administration (FDA) or similar (inter)national entities. Recombinant DNA techniques, hybridoma technologies, mammalian cell culturing, metabolic engineering, and fermentation improvements have permitted large-scale production of biologics.

As large-scale production issues are solved, manufacturing steps that limit productivity are shifted downstream. In an effort to quicken time-to-clinic and market, research efforts have focused on cutting material costs, improving productivity at large-scale, and developing robust, generic separation steps. In the biologics manufacturing process, cell lines are cultivated to produce, or express, the biologic; during this process, the desired biologic is expressed alongside unwanted host cell proteins. These contaminants then have to be separated from the biologic through expensive and time-consuming multi-step purification processes that often include centrifugation, ultrafiltration, extraction, precipitation, and the cornerstone of bioseparation, chromatographic separation. Since downstream processes account for 50% to 80% of total manufacturing costs, efforts to optimize purification of high-value, high-quality products are critical to success in the biopharmaceutical industry. For example, if there is a modest 5% loss of biologic per purification step, final yields of about 70% are encountered should the processing require 5 to 8 downstream steps. This overall loss is intolerable as market demands for biologics increase. End-uses for peptides, polypeptides, and proteins produced recombinantly, other than biologics, include, but are not limited to, diagnostic kits (e.g., glucose dehydrogenase for glucose sensing), enabling technologies (e.g., ligases for recombinant DNA efforts), consumer products (e.g., proteases for laundry soap), manufacturing (e.g., isomerases for production of corn syrup), and biofuel generation (e.g., cellulases for switchgrass processing). Materials of these product categories also suffer from the desire for efficient downstream processing, although their product validation is less stringent than for a biologic.

For the illustrations above, both recovery from the culture and purification are paramount. Challenges to the industry standard technique of column chromatography, a critical element to most bioseparation schemes, are dictated by lack of separation efficiency, the variety of chromatography separation media, and the diverse composition of the mobile phase. Lack of separation efficiency manifests itself predominantly as a reduction in column capacity, defined as the amount of target molecule bound per adsorption cycle, and selectivity, defined as the amount of target molecule bound divided by the total amount of material bound per adsorption cycle. The traditional method of addressing separation efficiency is empirical, and is driven by past experience because no software design tool, similar to CHEMCAD (chemical engineering) and SPICE (electrical engineering), for bioseparation process design exists in the public domain, if at all. Therefore, any improvements in the recovery of peptides, polypeptides, or proteins in terms of an increase in separation efficiency, column capacity in particular, have been traditionally gained by improvements in the properties of the chromatographic adsorbent, by artful design of the gradient used to elicit separation, or in some cases, by the enhancement of binding through the addition of $His_6$, maltose binding protein, $Arg_8$, or similarly designed affinity tails or tags. Although affinity tails or tags are widely used for purification of recombinant proteins, in particular through the use of $His_6$, the continued presence of genomic peptides, polypeptides, and proteins exhibiting affinity for the resins used in these chromatographic methods remains problematic. Notably, when host cell genomic peptides, polypeptides, and proteins are retained in the adsorption step, significant losses in column capacity and complications in gradient elution occur. Selection of companion chromatographic steps in a rational manner to increase separation efficiency, i.e., separation capacity (product recovery), separation selectivity (product purity), or both, is nearly impossible due to lack of knowledge regarding the contaminant species, and is therefore developed somewhat arbitrarily, requiring tedious, time-consuming, and expensive trial and error experimentation.

As disclosed herein, one route to supplement traditional means to aid in the purification of peptides, polypeptides, or proteins would be to alter the proteome of the host cell in order to reduce the burden of host cell contaminant adsorption. This concept is orthogonal to the series of patents and applications by Blattner et al. that disclose a number of different strains of *E. coli* engineered to contain reduced genomes—in contrast to the proteome—to facilitate the production of recombinant proteins (U.S. Pat. Nos. 8,178,339; 8,119,365; 8,043,842; 8,039,243; 7,303,906; 6,989,265; US20120219994A1; and EP1483367B1). U.S. Pat. No. 8,119,365 claims *E. coli* wherein the genome is between 4.41 Mb and 2.78 Mb. U.S. Pat. No. 8,043,842 claims *E. coli* wherein the genome is between 4.27 Mb and 4.00 Mb. U.S. Pat. No. 8,039,243 claims variously between 4.41 and 3.71 Mb, 4.31 Mb and 3.71 Mb, and 4.27 Mb and 3.71 Mb. U.S. Pat. No. 6,989,265 discloses *E. coli* wherein the genome is at least 5% to at least 14% smaller than the genome of its native parent strain. EP1483367B1 claims *E. coli* having a chromosome that is genetically engineered to be 5% to 40% smaller than the chromosome of its native parent *E. coli* strain.

These documents variously discuss the concepts of reduced genome *E. coli* for use in the production of recombinant proteins, improving recombinant protein expression in *E. coli* by improving the growth/yield properties and robustness as a recombinant host by eliminating large numbers of non-essential genes and improving *E. coli* transformation competence. Expression of endogenous/native proteins in host cells is also presumed to be reduced. None of these documents either discloses or discusses chromatographic purification procedures, or the optimization thereof in conjunction with the design of optimized host cells, to improve separation efficiency leading to a purified or partially purified target peptide, polypeptide, or protein.

U.S. 2009/0075352 discloses the use of in silico comparative metabolic and genetic engineering analyses to improve the production of useful substances in host strains by comparing the genomic information of a target strain for producing a useful substance to the genomic information of a strain that overproduces the useful substance by screening for, and by deleting genes unnecessary for the overproduction of the useful substance, thereby improving product yield. This work illustrates metabolic engineering efforts directed to small molecule production (succinic acid), and as in the case of the patent documents discussed above, this application does not disclose or discuss chromatographic purification procedures, or the optimization thereof to improve separation efficiency leading to a target peptide, polypeptide, or protein.

Yu et al. (2002) *Nature Biotechnol.* 20:1018-1023 discloses a method for determining essential genes in *E. coli* and minimizing the bacterial genome by deleting large genomic fragments, thereby deleting genes that are nonessential under a given set of growth conditions and identifying a minimized set of essential *E. coli* genes and DNA sequences. Neither the term "chromatography" nor "purification" is mentioned.

U.S. application 2012/0183995 discloses genetic modification of *Bacillus* species to improve the capacity to produce expressed proteins of interest, wherein one or more chromosomal genes are inactivated or deleted, or wherein one or more indigenous chromosomal regions are deleted from a corresponding wild-type *Bacillus* host chromosome. This includes removing large regions of chromosomal DNA in a *Bacillus* host strain wherein the deleted indigenous chromosomal region is not necessary for strain viability. These modifications enhance the ability of an altered *Bacillus* strain to express a higher level of a protein of interest over a corresponding non-altered *Bacillus* host strain. This application does not discuss improved chromatographic separation of expressed target recombinant peptides, polypeptides, or proteins from endogenous *Bacillus* proteins.

Asenjo et al. (2004), "Is there a rational method to purify proteins? From expert systems to proteomics", *Journal of Molecular Recognition* 17:236-247, discusses optimizing protein purification steps based on knowledge of the physicochemical properties of the target protein product and the protein contaminants. The paper notes "the rule of thumb that reflects the logic of first separating impurities present in higher concentrations." The concept of reduced genome host cells is not disclosed.

While the above-mentioned patents and journal articles do not disclose or discuss chromatographic purification procedures or the improvement of chromatographic separation efficiency, other references either outline the general process by which data on host cell proteins that interact with chromatography media can be obtained, or focus on the elimination of product-specific impurities through gene knockout. Cai et al. (2004) *Biotechnol. Bioeng.* 88:77 and Tiwari et al. (2010) *Protein Expression and Purification* 70:191-195 disclose the application of cellular extracts of *E. coli* to various affinity and non-affinity chromatographic media, and the identification of adsorbed proteins by mass spectroscopy and 2D gel electrophoresis. While the metabolic characteristics of the proteins encountered were discussed, these references do not disclose any indications of improvement in separation efficiency. Liu et al. (2009) *J. Chromatog. A* 1216:2433-2438, Bartlow et al. (2011) *Protein Expression and Purification* 78:216-224, and Bartlow et al. (2012) *American Institute of Chemical Engineers Biotechnol. Prog.* 28:137-145 disclose the potential for improvement in product quality, purity in particular, should genes that express proteins that co-elute with a specific protein, i.e., histidine-extended Green Fluorescent Protein, be deleted from the chromosome of *E. coli*. The quantitative data in this series of papers do not disclose or suggest improvements that lead to an increase in column capacity, nor do they demonstrate or suggest improvements that point to a universally applicable host strain with improved properties, useful for producing a variety of different peptides, polypeptides, or proteins, be they extended with an affinity tail or tag (or not). Indeed, should the genes identified and deemed important in Liu et al. (2009), supra, be deleted, an increase of significantly less than one percent (1%) in column capacity would be achieved. A similar argument for the deletion of genes responsible for product-specific contaminants applies to Caparon et al. (2010) *Biotechnol. Bioeng.* 105(2):239-249. This article discloses four specific gene deletions that improve the purity of the final biologic, since three of the proteins co-elute with the target and a fourth causes proteolytic degradation of the biologic. Lacking in this reference is a means of applying quantitative metrics to prioritize efforts that lead to increases in separation efficiency independent of target peptides, polypeptides, and proteins, and a method to interpret these data to prepare a host cell or set of host cells that provide increases in separation efficiency for as many different target molecules as possible.

In view of the foregoing, there exists a need for improved methods for recovering in quantity, and purifying, recombinant target peptides, polypeptides, and proteins from *E. coli* and other host cells routinely used for recombinant expression of, for example, therapeutic proteinaceous molecules and industrial enzymes. Development of bioseparation regimens can be challenging, requiring somewhat arbitrary trial and error combination of conventional chromatographic methods. The presence of host cell peptides, polypeptides, and proteins reduces separation step efficiency (adsorption and elution), and the tradeoff between overall yield and purity may not be optimal. Alternately, although the use of an affinity tail helps reduce the chromatographic space explored, it can still be plagued by co-adsorbing/co-eluting molecules, requiring further purification steps; addition/removal of the affinity tail via digestion steps; and cost (ligand and endonuclease).

The methods and host cells disclosed herein address these problems and meet these needs. These methods and host cells provide a novel route to supplement or supplant conventional methods to aid in the purification of target recombinant peptides, polypeptides, and proteins. This is accomplished by providing a rational scheme for altering the proteome of host cells used for expression in order to reduce the burden of adsorption of host cell peptides, polypeptides, and proteins that may interfere with the recovery and purification of any target molecule. This is accomplished by first identifying the separatome, defined as a sub-proteome associated with a separation technique, column chromatography for example, by applying a formal method that mathematically prioritizes specific modifications to the proteome via, for example, gene knockout, gene silencing, gene modification, or gene inhibition, and designing host cells with the desired property of improved chromatographic separation based on this information. Host cells, or sets of host cells, as disclosed herein display a reduced separatome, the properties of which lead to an increase in column capacity as peptides, polypeptides, or proteins with high affinity are eliminated first. Uniquely focusing on host cell peptides, polypeptides, or proteins with high affinity, rather than those with affinity similar to, or less than a presumed target recombinant molecule, facilitates a set of modifications that are useful for improving separation efficiency for a wide range of peptides, polypeptides, or proteins. Such high affinity host cell peptides, etc., are problematic regardless of the nature of the target recombinant molecule because not only can they display an elution profile that may decrease purity, but they also remain bound to the column due to the stringent conditions necessary for their desorption.

The separatome-based protein expression and purification platform disclosed herein provides the benefits of, but is not be limited to, reduction of the chromatography regimen, column capacity loss due to host cell contaminating peptide, polypeptide, and protein adsorption, and complexity of elution protocols since the number, and nature, of interfering peptides, polypeptides, and proteins to be resolved is less.

The present separatome-based protein expression and purification platform facilitates the modification of unoptimized host cell lines in order to eliminate the expression of undesirable, interfering peptides, polypeptides, and proteins during host cell cultivation, thereby reducing the total amount and cost of purification needed to produce a higher concentration, and absolute amount, of purified target recombinant product.

The separatome-based invention disclosed herein further provides a proteomics-based protein expression and purification platform based on a computer database and modeling system of separatome data for individually customized cell lines that facilitate recovery and purification of difficult to express, low yield proteins.

The separatome-based expression and purification platform disclosed herein also provides for modified host cell lines having a genome encoding and/or expressing a reduced number of nuisance or contaminating proteins, thereby decreasing the complexity and costs of the purification process.

Furthermore, the present invention provides a separatome-based expression and purification platform that utilizes an engineered series of broadly applicable bacterial and other host cells to provide facile purification systems for target recombinant peptide, polypeptide, and protein separation.

Compared to previous approaches involving the deletion of large numbers of host cell genes, the separatome-based method for designing host cells for expression of target peptides, polypeptides, and proteins provided herein is more "surgical", i.e., targeted and precise, and does not result in the deletion of large regions of host cell genomes. The present invention provides a rational framework for optimizing target recombinant peptide, polypeptide, or protein recovery and purification based on identification of host cell peptide, polypeptide, and protein contaminants that reduce the separation efficiency, i.e., separation capacity (product recovery), separation selectivity (product purity), or both, of target recombinant peptides, polypeptides, and proteins based on knowledge of the binding characteristics of contaminating species during chromatographic purification. This permits the coordinated design of universally useful, optimized host cells for target recombinant peptide, polypeptide, or protein expression and concomitant purification procedures using the smallest number of operations, and eliminates the need for arbitrary, tedious, time-consuming, and expensive trial and error experimentation. The methods disclosed herein avoid the need to design individualized host cell expression and chromatographic systems for specific recombinant target proteinaceous products, and provide a rational "separatomic" procedure and materials to eliminate and separate the main interfering peptide, polypeptide, and protein components of host cells using the minimum number of process steps. The present methods and host cells minimize, or in most cases, completely avoid the problems of eliminating host cell genes and proteins required for growth, viability, and target molecule expression that would adversely affect the use of such cells for expression of target recombinant peptides, polypeptides, and proteins. In some cases, the present engineered host cells exhibit improved growth, viability, and expression compared to the parental cells from which they are derived. This can be attributed, at least in part, to avoiding or circumventing the problem of eliminating genes that are dispensable individually, but not in combination.

SUMMARY

Accordingly, among its many embodiments, the present invention provides a separatome-based protein expression and purification platform comprising a system of separatome data for a host cell, which comprises data compiled on the genome and proteome sequences of the host cell, and a data visualization tool for graphically displaying such separatome data for identification and/or modification of contiguous or individual regions of nuisance or coeluting proteins of host cells. The separatome data can comprise data compiled on the metalloproteome and metabolome of the host cell. Host cells included in this platform include, for example, Escherichia coli, yeasts, Bacillus subtilis and other prokaryotes, and any of the other host cells conventionally used for expression of peptides, polypeptides, and proteins disclosed herein.

The system of separatome data is based on identified, conserved genomic regions of host cells that span resin- and gradient-specific chromatographies based on a relationship of binding properties of the peptides, polypeptides, and proteins encoded by the identified, conserved genomic regions for these chromatographies with the characteristics and location of genes on the chromosome(s) of host cells. The chromatographies include Immobilized-Metal Affinity Chromatography (IMAC), cation exchange chromatography (cation IEX), anion exchange chromatography (anion IEX), Hydrophobic Interaction Chromatography (HIC), or combinations thereof.

Among its many embodiments, the present invention also encompasses a separatome-based protein expression and purification process for manufacturing of a modified cell line having a genome encoding a reduced number of contaminating peptides, polypeptides and proteins, wherein the process comprises the steps of:

(1) graphically displaying a separatome of a target host cell line as a visualization tool in conjunction with relevant biochemical information;

(2) identifying specific genes, and combinations of genes, coding for contaminating peptides, polypeptides, and proteins for the target host cell line, and/or identifying specific genes, or combinations of genes, encoding particular nuisance peptides, polypeptides, and proteins of the target host cell line;

(3) identifying, when possible, large contiguous genomic regions coding for contaminating peptides, polypeptides, and proteins for the target host cell line, and/or identifying specific genes encoding particular nuisance peptides, polypeptides, and proteins of the target host cell line;

(4) deleting the large contiguous genomic regions coding for contaminating peptides, polypeptides, and proteins, and/or the specific genes, or combinations of genes, encoding particular nuisance peptides, polypeptides, and proteins, of the target host cell line from the genome of the target host cell by large scale or targeted knockout, respectively; and (5) deleting regions encoding any contaminant peptides, polypeptides, or proteins remaining in the genome of the target host cell after step (3) by gene specific knockout and/or PCR point mutation to form the modified cell line.

The target host cells specifically exemplified herein are Escherichia coli cells conventionally used for expression.

In this process, the separatome is a system of chromatographic data of the juxtaposition of binding properties of peptides, polypeptides, and proteins encoded by identified, conserved genomic regions for chromatography methods with the characteristics and location of genes on the chromosome of the target host cell. The chromatographic methods of this process comprise Immobilized-Metal Affinity Chromatography (IMAC), cation exchange chromatography (cation IEX), anion exchange chromatography (anion IEX), Hydrophobic Interaction Chromatography (HIC), or combinations thereof.

In this process, step (1) further comprises identifying the contaminating proteins as essential and nonessential peptides, polypeptides, and proteins of the target host cell. Coding regions (genes) for essential peptides, polypeptides, and proteins can be reintroduced into the genome of the target host cell. The process can further comprise the step of constructing a larger fragment homologous to the target host cell. The fragment can be linear and sequenced with essential genes, and further comprises marker selection and selection removal.

The present invention also provides optimized strains of Escherichia coli modified by a separatome-based peptide, polypeptide, and protein expression and purification process, wherein the strain comprises a genome having (encoding) a reduced number of nuisance or coeluting peptides, polypeptides, and proteins. The separatome-based peptide, polypeptide, and protein expression and purification process can be a two-step purification process based on chromatotomes of combinations of chromatographies of Escherichia coli, and the nuisance or coeluting proteins can be reduced via large scale knockout, gene specific knockout, PCR point mutation, or a combination thereof.

More particularly, in a first set of embodiments, the present invention encompasses the following:

1. A host cell for expression of a target recombinant peptide, polypeptide, or protein, comprising:
   i) a reduced genome compared to the genome in the parent cell from which it is derived, or
   ii) a modified genome compared to the genome in the parent cell from which it is derived, or
   iii) in which expression of genes is reduced or completely inhibited compared to expression of said genes in the parent cell from which it is derived,
   wherein genes that are deleted, modified, or the expression of which is reduced or completely inhibited in said host cell, code for peptides, polypeptides, or proteins that impair the chromatographic separation efficiency of said target recombinant peptide, polypeptide, or protein expressed in said host cell.

2. The host cell of 1, wherein said chromatographic separation efficiency of said target recombinant peptide, polypeptide, or protein is improved compared to the chromatographic separation efficiency of said target recombinant peptide, polypeptide, or protein in the presence of peptides, polypeptides, or proteins coded for by said genes that are deleted, modified, or the expression of which is reduced or completely inhibited in said host cell upon affinity or adsorption, non-affinity column chromatography of said target recombinant peptide, polypeptide, or protein.

3. The host cell of 2, wherein improvement of said chromatographic separation efficiency of said target recombinant peptide, polypeptide, or protein is in the range of from about 5% to about 35%, or from about 10% to about 20%, compared to chromatographic separation efficiency of said target recombinant peptide, polypeptide, or protein in the presence of peptides, polypeptides, or proteins coded for by said genes that are deleted, modified, or the expression of which is reduced or completely inhibited in said host cell upon affinity or adsorption, non-affinity column chromatography of said target recombinant peptide, polypeptide, or protein.

4. The host cell of any one of 1-3, wherein said chromatographic separation efficiency is independent of elution conditions under which said target recombinant peptide, polypeptide, or protein emerges from an affinity or adsorption, non-affinity chromatography column as an enriched fraction.

5. The host cell of any one of 1-4, wherein deletion of said gene is performed by homologous recombination or frame shift mutation.

6. The host cell of any one of 1-4, wherein modification of said genes is performed by a method selected from the group consisting of point mutation, isozyme substitution, and transposon mutagenesis.

7. The host cell of any one of 1-4, wherein expression of said genes is reduced or completely inhibited by a method selected from the group consisting of RNA silencing, antisense oligonucleotide inhibition, and replacement of a native promoter with a weaker promoter.

8. The host cell of any one of 1-7, which exhibits about 75% to about 100% of the viability, growth rate, or capacity for expression of said target recombinant peptide, polypeptide, or protein expressed in said host cell compared to that of said parent cell from which it is derived, or which exhibits viability, growth rate, or capacity for expression of said target recombinant peptide, polypeptide, or protein expressed in said host cell greater than that of said parent cell from which it is derived.

9. The host cell of any one of 1-8, wherein said target recombinant peptide, polypeptide, or protein is present in a lysate of said host cell, or is secreted by said host cell.

10. The host cell of any one of 1-9, wherein said target recombinant peptide, polypeptide, or protein is an endogenous peptide, polypeptide, or protein.

11. The host cell of 10, wherein said endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

12. The host cell of any one of 1-9, wherein said target recombinant peptide, polypeptide, or protein is a heterologous peptide, polypeptide, or protein.

13. The host cell of 12, wherein said heterologous peptide, polypeptide, or protein is selected from the group consisting of an enzyme and a therapeutic peptide, polypeptide, or protein.

14. The host cell of 13, wherein said enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and said therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, tissue plasminogen activator, and insulin.

15. The host cell of any one of 1-14, which is selected from the group consisting of a bacterium, a fungus, a mammalian cell, an insect cell, a plant cell, and a protozoal cell.

16. The host cell of 15, wherein said bacterium is *E. coli, B. subtilis, P. fluorescens*, or *C. glutamicum*; said fungus is a yeast selected from the group consisting of *S. cerevisiae* and *K. pastoris*; said mammalian cell is a CHO cell or a HEK cell; said insect cell is an *S. frugiperda* cell; said plant cell is a tobacco, alfalfa, rice, tomato, or soybean cell; and said protozoal cell is a *L. tarentolae* cell.

17. The host cell of 16, wherein said bacterium is *E. coli*.

18. The *E. coli* host cell of 17, wherein said parent cell from which said *E. coli* host cell is derived is selected from the group consisting of *E. coli* K-12, *E. coli* MG, *E. coli* BL, and *E. coli* DH.

19. The host cell of 16, wherein said bacterium is *B. subtilis*.

20. The *B. subtilis* host cell of 19, wherein said parent cell from which said *B. subtilis* host cell is derived is selected from the group consisting of *B. subtilis* 168 and *B. subtilis* BSn5.

21. The host cell of 16, wherein said *S. cerevisiae* and *K. pastoris* are selected from the group consisting of *S. cerevisiae* S288c and AWRI796, and *K. pastoris* CBS7435 and GS115, respectively.

22. The host cell of 16, wherein said CHO cell is CHO-K1 and said HEK cell is HEK 293.

23. The *E. coli* parent cell of 18, which is selected from the group consisting of *E. coli* K-12, *E. coli* MG1655, *E. coli* BL21 (DE3), and *E. coli* DH10B.

24. *E. coli* strain K-12, MG1655, BL21 (DE3), and DH10B of 23, having a genome comprising the nucleotide sequence disclosed in the reference of Table Entry Number 1, 2, 3, and 4, respectively, in Table 1.

25. *B. subtilis* strain 168 and BSn5 of 20, having a genome comprising the nucleotide sequence disclosed in the reference of Table Entry Number 1 and 2, respectively, in Table 2.

26. *S. cerevisiae* strain S288c and AWRI796 of 21, having a genome comprising the nucleotide sequence disclosed in the reference of Table Entry Number 1 and 2, respectively, in Table 3.

27. *K. pastoris* strain CBS7435 and GS115 of 21, having a genome comprising the nucleotide sequence disclosed in the reference of Table Entry Number 1 and 2, respectively, in Table 4.

28. CHO cell strain CHO-K1 of 22, having a genome comprising the nucleotide sequence disclosed in the reference of Table Entry Number 1 in Table 5.

29. HEK cell strain HEK 293 of 22, having a genome comprising the nucleotide sequence disclosed in the reference of Table Entry Number 1 in Table 6.

30. The *E. coli* host cell of any one of 16-18 or 23-24, wherein said reduced genome compared to the genome in the parent cell from which it is derived is less than 5% smaller, less than about 4.5% smaller, less than about 4% smaller, less than about 3.5% smaller, less than about 3% smaller, less than about 2.5% smaller, less than about 2% smaller, less than about 1.5% smaller, or less than about 1% smaller, than the genome of said parent cell from which it is derived.

31. The *E. coli* host cell of any one of 16-18 or 23-24, wherein said reduced genome compared to the genome in the parent cell from which it is derived is between about 4.17 Mb to about 4.346 Mb.

32. An *E. coli* host cell for expression of a target recombinant peptide, polypeptide, or protein, comprising:
   i) a reduced genome compared to the genome in the parent cell from which it is derived, or
   ii) a modified genome compared to the genome in the parent cell from which it is derived, or
   iii) in which expression of genes is reduced or completely inhibited compared to expression of said genes in the parent cell from which it is derived,
   wherein said parent cell is *E. coli* strain K-12, MG1655, BL21 (DE3), or DH10B, having a genome comprising the nucleotide sequence disclosed in the reference of Table Entry Number 1, 2, 3, and 4, respectively, in Table 1, and
   wherein genes that are deleted, modified, or the expression of which is reduced or completely inhibited in said host cell compared to expression of said genes in said parent cell from which it is derived, code for proteins that impair the chromatographic separation efficiency of said target recombinant peptide, polypeptide, or protein expressed in said host cell in the presence of peptides, polypeptides, or proteins coded for by said genes that are deleted, modified, or the expression of which is reduced or completely inhibited in said host cell, and that elute from a chromatographic affinity column having a ligand, in a buffer comprising a compound that dictates adsorption to its respective ligand during equilibration and elution from said affinity column, in an amount in the range, in a combination selected from the group consisting of the combinations in the following table A:

TABLE A

| Ligand | Compound in Buffer That Dictates Adsorption to Affinity Column During Equilibration and Causes Elution From Column | Concentration or pH Range |
|---|---|---|
| Glutathione S-transferase | Glutathione | from about 0 mM to about 10 mM |
| Amino acid (e.g., lysine) | A common salt | from about 0 mM to about 2M |
| Amino acid | pH | from about pH 2 to about pH 11 |
| Avidin | A chaotropic salt | from about 0M to about 4M |
| Avidin | pH | from about pH 2 to about pH 10.5 |
| Carbohydrate (e.g., Dextrin) | Sugar or isocratic (e.g., maltose) | from about 0 mM to about 10 mM |
| Carbohydrate | pH | from about pH 5 to about pH 8 |
| Organic dye (e.g., Cibacron Blue) | A common salt | from about 0 mM to about 1.5M |
| Organic dye | pH | from about pH 4 to about pH 8 |
| Organic dye | Imidazole or a common salt | from about 5 mM to about 250 mM |
| Divalent metal (e.g., Ni(II)) | pH | from about pH 4 to about pH 12 |
| Divalent metal (e.g., Ni(II)) | Imidazole | from about 5 mM to about 500 mM |
| Heparin | A common salt | from about 0 mM to about 2M |
| Protein A or Protein G | Glycine | from about 0 mM to about 100 mM |
| Protein A or Protein G | pH | from about pH 3 to about pH 7 |
| IgG | Glycine | from about 0 mM to about 100 mM |
| Coenzyme | Competing Protein | from about 1 mM to about 12 mM |

33. An *E. coli* host cell for expression of a target recombinant peptide, polypeptide, or protein, comprising:
   i) a reduced genome compared to the genome in the parent cell from which it is derived, or
   ii) a modified genome compared to the genome in the parent cell from which it is derived, or
   iii) in which expression of genes is reduced or completely inhibited compared to expression of said genes in the parent cell from which it is derived,
   wherein said parent cell is *E. coli* strain K-12, MG1655, BL21 (DE3), or DH10B, having a genome comprising the nucleotide sequence disclosed in the reference of Table Entry Number 1, 2, 3, and 4, respectively, in Table 1,
   wherein genes that are deleted, modified, or the expression of which is reduced or completely inhibited in said host cell, code for host cell peptides, polypeptides, or proteins that impair the chromatographic separation efficiency of said target recombinant peptide, polypeptide, or protein expressed in said host cell, and
   wherein genes that are deleted, modified, or the expression of which is reduced or completely inhibited in said host cell compared to expression of said genes in said parent cell from which it is derived, code for proteins that impair the chromatographic separation efficiency of said target recombinant peptide, polypeptide, or protein expressed in said host cell in the presence of peptides, polypeptides, or proteins coded for by said genes that are deleted, modified, or the expression of which is reduced or completely inhibited in said host cell, and that elute from a chromatographic adsorption, non-affinity column having a ligand, in a buffer comprising a compound that dictates adsorption to its respective ligand during equilibration and elution from said adsorption, non-affinity column, in an amount in the range, in a combination selected from the group consisting of the combinations in the following table B:

TABLE B

| Ligand | Compound in Buffer That Dictates Adsorption to Non- Affinity Column During Equilibration and Causes Elution From Column | Concentration or pH Range |
|---|---|---|
| Ion exchange | Common salt | from about 0M to about 2M |
| Ion exchange | pH | from about pH 2 to about pH 12 |
| Reverse phase | Organic solvent ex. Acetonitrile | from about 0% to about 100% |
| Hydrophobic interaction | Common salt | from about 2M to about 0M |

34. The *E. coli* host cell of 32 or 33, wherein said common salt is selected from the group consisting of a chloride salt, a sulfate salt, an acetate salt, a carbonate salt, and a propionate salt.

35. The *E. coli* host cell of 33, wherein said organic solvent is selected from the group consisting of acetonitrile, methanol, and 2-propanol.

36. The *E. coli* host cell of 33, wherein genes that are deleted, modified, or the expression of which is inhibited, in the genome of said *E. coli* host cell are selected from the group consisting of the genes listed in Table C:

TABLE C

| GeneName |
| --- |
| rpoC |
| rpoB |
| hldD |
| metH |
| entF |
| mukB |
| tgt |
| rnr |
| glgP |
| recC |
| ycaO |
| glnA |
| ptsI |
| metE |
| sucA |
| hrpA |
| groL |
| gatZ |
| speA |
| thiI |
| nusA |
| tufA |
| degP |
| clpB |
| rapA |
| metL |
| ycfD |
| nagD |
| ilvA |
| fusA |
| cyaA |
| gldA |
| dnaK |
| ygiC |
| gyrA |
| glnE |
| carB |
| ppsA |
| degQ |
| usg |
| ilvB |
| thrS |
| recB |
| entB |
| dusA |
| typA |
| prs |
| cysN |
| atpD |
| purL | and combinations thereof.

37. The *E. coli* host cell of 33, wherein said parent cell *E. coli* strain is MG1655 (genotype: Wild Type: F-, λ-, rph-1), and the following combinations of genes are deleted, modified, or the expression of which is inhibited: LTS00 (genotype: ΔthyA); LTS01+ (genotype: ΔmetH); LTS01 (genotype: ΔthyAΔmetH); LTS02+ (genotype: ΔmetHΔentF); LTS02 (genotype: ΔthyAΔmetHΔentF); LTS03+ (genotype: ΔmetHΔentFΔtgt); LTS03 (genotype: ΔthyAΔmetHΔentFΔtgt); LTS04+ (genotype: ΔmetHΔentFΔtgtΔrnr); LTS04 (genotype: ΔthyAΔmetHΔentFΔtgtΔrnr); or LTS05+ (genotype: ΔmetHΔentFΔtgtΔrnrΔycaO).

38. The host cell of any one of 1-37, wherein increased separation efficiency is manifested as increased separation capacity, increased separation selectivity, or both.

39. The host cell of 38, wherein separation capacity is defined as the amount of target recombinant peptide, polypeptide, or protein adsorbed to said column per mass lysate in the case where said target recombinant peptide, polypeptide, or protein is not secreted, or mass culture medium in the case where said target recombinant peptide, polypeptide, or protein is secreted, applied to said column, and separation selectivity is defined as the amount of target recombinant peptide, polypeptide, or protein adsorbed to said column per total peptide, polypeptide, or protein adsorbed to said column.

40. The host cell of 38 or 39, wherein said increased separation capacity is in the range of from about 5% to about 35%.

41. The host cell of any one of 1-40, wherein separation of said target recombinant peptide, polypeptide, or protein from host cell peptides, polypeptides, or proteins is performed by column chromatography employing a solid phase chromatography medium.

42. The host cell of 41, wherein said column chromatography is selected from the group consisting of affinity chromatography employing an affinity ligand bound to said solid phase, and adsorption-based, non-affinity chromatography.

43. The host cell of 42, wherein said affinity ligand is selected from the group consisting of an amino acid, a divalent metal ion, a carbohydrate, an organic dye, a coenzyme; glutathione S-transferase, avidin, heparin, protein A, and protein G.

44. The host cell of 43, wherein said divalent metal ion is selected from the group consisting of $Cu^{++}$, $Ni^{++}$, $Co^{++}$, and $Zn^{++}$; said carbohydrate is selected from the group consisting of maltose, arabinose, and glucose; said organic dye is a dye comprising a triazene moiety; and said coenzyme is selected from the group consisting of NADH and ATP.

45. The host cell of 42, wherein said adsorption-based, non-affinity chromatography is selected from the group consisting of ion exchange chromatography, reverse phase chromatography, and hydrophobic interaction chromatography.

46. The host cell of 45, wherein said adsorption-based, non-affinity chromatography is ion exchange chromatography.

47. The host cell of 46, wherein said ion exchange chromatography employs a ligand selected from the group consisting of diethylaminoethyl cellulose (DEAE), monoQ, and S.

48. The host cell of any one of 41 to 47, wherein said host cell peptides, polypeptides, or proteins that impair separation efficiency of said target recombinant peptide, polypeptide, or protein expressed in said host cell are peptides, polypeptides, or proteins that are strongly retained during column chromatography.

49. The host cell of 48, wherein said host cell peptides, polypeptides, or proteins that are strongly retained during ion exchange chromatography are those that are retained during elution with a mobile phase comprising a common salt in the range of from about 5 mM to about 2,000 mM.

50. The host cell of 49, wherein said host cell peptides, polypeptides, or proteins that are strongly retained during ion exchange chromatography are those that are retained during elution with a mobile phase comprising a common salt in the range of from about 500 mM to about 1,000 mM.

51. The host cell of any one of 41 to 50, wherein said host cell peptides, polypeptides, or proteins that impair the separation efficiency of said target recombinant peptide, polypeptide, or protein expressed in said host cell are peptides, polypeptides, or proteins that are weakly retained during column chromatography.

52. The host cell of 50, wherein said host cell peptides, polypeptides, or proteins that are weakly retained during chromatography are those that are retained during elution with a mobile phase comprising a common salt in the range of from about 5 mM to about 500 mM.

53. The host cell of 52, wherein said host cell peptides, polypeptides, or proteins that are weakly retained during chromatography are those that are retained during elution with a mobile phase comprising a common salt in the range of from about 10 mM to about 350 mM.

54. The host cell of any one of 41 to 53, wherein said host cell peptides, polypeptides, or proteins that impair the separation efficiency of said target recombinant peptide, polypeptide, or protein expressed in said host cell are peptides, polypeptides, or proteins that are both strongly retained and weakly retained during column chromatography.

55. A separatome of chromatographically relevant host cell peptides, polypeptides, and proteins for column affinity chromatography employing an affinity ligand bound to a solid phase or column adsorption-based, non-affinity chromatography, comprising host cell peptides, polypeptides, and proteins based on their capacity recovery potential from said column,
wherein said capacity recovery potential of said host cell peptides, polypeptides, and proteins is quantitatively determined by:
(a) scoring a peptide, polypeptide, or protein (i) with the formulae:

$$\text{importance}_i = \sum_j \left[ b_1 \left( \frac{y_{c_j}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i \quad \text{Equation 3}$$

with values for a series of peptides, polypeptides, and proteins written in descending order (largest value close to unity downwards to the smallest value), followed by
(b) calculating the capacity recovery potential of a relevant peptide, polypeptide, or protein (i) given by:

$$\text{recovery potential}_i = h_{i,total}/h_{total,ms}, \quad \text{Equation 1}$$

wherein the following definitions apply: $y_{c_j}$ and $y_{max}$=concentration of mobile phase eluent in fraction (j) and maximum value, respectively; and $h_{i,j}$ and $h_{i,total}$=the amount of protein (i) in fraction (j) and total bound protein (i), respectively; $h_{j,total}$=total amount of protein in fraction (j); $h_{total,ms}$=total mass of protein bound to column; $b_1$=scaling parameter; $\alpha$=steric factor; $MW_i$ and $MW_{ref}$=molecular weight of protein (i) or reference protein, respectively.

56. The separatome of 55, wherein said affinity ligand in said column affinity chromatography employing an affinity ligand bound to a solid phase is selected from the group consisting of an amino acid, a divalent metal ion, a carbohydrate, an organic dye, a coenzyme, glutathione S-transferase, avidin, heparin, protein A, and protein G.

57. The separatome of 56, wherein peptides, polypeptides, and proteins are eluted from said affinity chromatography column using an elution agent y selected from the group consisting of a common salt, hydronium ion, imidazole, glutathione, a chaotropic salt, heparin, and glycine.

58. The separatome of 55, wherein said column adsorption-based, non-affinity chromatography is selected from the group consisting of ion exchange chromatography, reverse phase chromatography, and hydrophobic interaction chromatography.

59. The separatome of 58, wherein peptides, polypeptides, and proteins are eluted from said adsorption-based, non-affinity chromatography column using an elution agent y selected from the group consisting of a common salt, hydronium ion, and an organic solvent.

60. The separatome of 57 or 59, wherein said common salt is selected from the group consisting of a chloride salt, a sulfate salt, an acetate salt, a carbonate salt, and a propionate salt.

61. The separatome of 59, wherein said organic solvent is selected from the group consisting of methanol, 2-propanol, and acetonitrile.

62. The separatome of 57, wherein said chaotropic salt is guanidine hydrochloride.

63. The separatome of any one of 55-62, wherein the maximum value of said elution agent y is defined by $y_{max}$ in 55.

64. The separatome of any one of 55-63, which is in a form selected from the group consisting of a table, a visual representation such as a figure, and a computer file.

65. The separatome of chromatographically relevant host cell peptides, polypeptides, or proteins for column affinity chromatography employing an affinity ligand bound to a solid phase of any one of 55-57, 60, or 62-64.

66. The separatome of chromatographically relevant host cell peptides, polypeptides, or proteins for column adsorption-based, non-affinity chromatography of any one of 55, 58-61, or 63-64.

67. A method for designing a reduced or modified proteome host cell, or a host cell in which expression of genes is reduced or completely inhibited compared to expression of said genes in the parent cell from which said host cell is derived, for expression of a target recombinant peptide, polypeptide, or protein to improve the chromatographic separation efficiency of said target recombinant peptide, polypeptide, or protein expressed in said host cell, comprising identifying and ranking proteins of chromatographic relevance that adversely affect said separation efficiency of said target recombinant peptide, polypeptide, or protein in a parent cell from which said host cell is derived by:
i) equilibrating an affinity chromatography column employing an affinity ligand bound to a solid phase, or an adsorption-based, non-affinity chromatography column, using a mobile loading or eluting phase, or an operational variable;
ii) in the case where said target recombinant peptide, polypeptide, or protein is not secreted, fractionating a lysate of said host cell, or in the case where said target recombinant peptide, polypeptide, or protein is secreted from said host cell, fractionating the culture medium in which said host cell is grown, on said column by applying an elution gradient to elute peptide, polypeptide, or protein fractions from said column;
iii) identifying, quantifying, and scoring peptides, polypeptides, or proteins in said fractions eluted from said column;
iv) assessing the metabolic role of said peptides, polypeptides, or proteins identified in step iii) that affect column capacity; and
v) designing a reduced or modified genome host cell, or a host cell in which expression of genes is reduced or completely inhibited compared to expression of said genes in the parent cell from which said host cell is derived, to modify the proteome of said parent cell from which said host cell is derived in order to increase chromatographic separation efficiency based on steps iii) and iv).

68. The method of 67, further comprising reducing or modifying the genome of said parent cell from which said host cell is derived, or reducing or completely inhibiting the expression of peptides, polypeptides, or proteins in said parent cell, to increase chromatographic separation efficiency based on step v), thereby producing a host cell comprising a reduced or modified genome compared to the genome in said parent cell from which said host cell is derived, or a host cell in which expression of peptides, polypeptides, or proteins is reduced or completely inhibited.

69. The method of 67 or 68, wherein said reduced or modified proteome host cell, or said host cell host cell in which expression of (n) genes is reduced or completely inhibited compared to expression of said genes in the parent cell from which said host cell is derived, facilitates an overall capacity recovery of said target recombinant peptide, polypeptide, or protein in the range of from about 5%, from about 10%, from about 20%, from about 30%, from about 40%, from about 50%, from about 60%, from about 70%, from about 80%, from about 90%, or from about 95%, to about 100%, wherein capacity recovery is defined by summing (n) values of recovery potential for individual (i) proteins by the following:

$$\text{capacity recovery} = 100\% \times \sum_{i=1}^{n} \text{recovery potential}_i \quad \text{Equation 2}$$

wherein n=total number of proteins that are deleted, inhibited, or modified, and i=an individual protein.

A preferred range for capacity recovery is from about 3% to about 50%, more preferably from about 5% to about 40%, or from about 5% to about 35%, 70. The method of any one of 67-69, wherein step i) is modified by varying the characteristics of said mobile loading or eluting phase or operational variable.
71. The method of any one of 67-70, wherein identification of said peptides, polypeptides, or proteins in step iii) is performed by comparing the LC-MS signature of said peptides, polypeptides, or proteins to publicly available standards.
72. The method of any one of 67-71, wherein quantification of said proteins in step iii) is performed using spectral counting, or a combination of Bradford protein assay, 2-dimensional electrophoresis, and densitometry.
73. The method of any one of 67-72, wherein said scoring in step iii) is calculated as in 55.
74. The method of any one of 67-73, wherein assessing the metabolic role of identified proteins in step iv) is performed by bioinformatics techniques.
75. A method of enriching the amount of a target recombinant peptide, polypeptide, or protein relative to other peptides, polypeptides, or proteins present in an initial protein mixture comprising said target recombinant peptide, polypeptide, or protein, comprising:
    i) selecting a chromatography medium that binds said target recombinant peptide, polypeptide, or protein from the group consisting of an affinity chromatography medium and an adsorption-based, non-affinity chromatography medium;
    ii) in the case where an affinity chromatography medium is selected, expressing said target recombinant peptide, polypeptide, or protein in said host cell of any one of 1-32, 34, 36, 38-44, 48, or 51-54;
    iii) in the case where an adsorption-based, non-affinity chromatography medium is selected, expressing said target recombinant peptide, polypeptide, or protein in said host cell of any one of 1-31, 33-35, 37-42, or 45-54; and
    iv) chromatographing said initial protein mixture comprising said target recombinant peptide, polypeptide, or protein using said chromatography medium of step ii) or step iii), as appropriate, and collecting elution fractions, thereby obtaining one or more fractions containing an enriched amount of said target recombinant peptide, polypeptide, or protein relative to other peptides, polypeptides, or proteins in said fraction compared to the amount of said target recombinant peptide, polypeptide, or protein relative to other peptides, polypeptides, or proteins in said initial protein mixture.
76. The method of 75, further comprising chromatographing an enriched fraction of step iv) to obtain said target recombinant peptide, polypeptide, or protein in a desired degree of purity.
77. The method of 76, further comprising recovering said target recombinant peptide, polypeptide, or protein.
78. A method of preparing a pharmaceutical or veterinary composition comprising a recombinant therapeutic peptide, polypeptide, or protein, comprising:
    i) selecting a chromatography medium that binds said recombinant therapeutic peptide, polypeptide, or protein from the group consisting of an affinity chromatography medium and an adsorption-based, non-affinity chromatography medium;
    ii) in the case where an affinity chromatography medium is selected, expressing said recombinant therapeutic peptide, polypeptide, or protein in said host cell of any one of 1-32, 34, 36, 38-44, 48, or 51-54;
    iii) in the case where an adsorption-based, non-affinity chromatography medium is selected, expressing said recombinant therapeutic peptide, polypeptide, or protein in said host cell of any one of 1-31, 33-35, 37-42, or 45-54;
    iv) in the case where said recombinant therapeutic peptide, polypeptide, or protein is not secreted from said host cell, preparing a lysate of said host cell containing said recombinant therapeutic peptide, polypeptide, or protein, producing an initial recombinant therapeutic peptide-, polypeptide-, or protein-containing mixture; or
    v) in the case where said recombinant therapeutic peptide, polypeptide, or protein is secreted from said host cell, harvesting culture medium in which said host cell is grown, containing said recombinant therapeutic peptide, polypeptide, or protein, thereby obtaining an initial recombinant therapeutic peptide-, polypeptide-, or protein-containing mixture;
    vi) chromatographing said initial recombinant therapeutic peptide-, polypeptide-, or protein-containing mixture of step iv) or step v) using said chromatography medium of step i) or step ii), as appropriate, and collecting elution fractions, thereby obtaining one or more fractions containing an enriched amount of said recombinant therapeutic peptide, polypeptide, or protein relative to other peptides, polypeptides, or proteins in said fraction compared to the amount of said recombinant therapeutic peptide, polypeptide, or protein relative to other peptides, polypeptides, or proteins in said initial protein mixture;

vii) further chromatographing an enriched fraction of step vi) to obtain said recombinant peptide, polypeptide, or protein in a desired degree of purity;

viii) recovering said recombinant therapeutic peptide, polypeptide, or protein; and ix) formulating said recombinant therapeutic peptide, polypeptide, or protein with a pharmaceutically or veterinarily acceptable carrier, diluent, or excipient to produce a pharmaceutical or veterinary composition, respectively.

79. A method of purifying a recombinant enzyme, comprising:

i) selecting a chromatography medium that binds said recombinant enzyme from the group consisting of an affinity chromatography medium and an adsorption-based, non-affinity chromatography medium;

ii) in the case where an affinity chromatography medium is selected, expressing said recombinant enzyme in said host cell of any one of 1-32, 34, 36, 38-44, 48, or 51-54;

iii) in the case where an adsorption-based, non-affinity chromatography medium is selected, expressing said recombinant enzyme in said host cell of any one of 1-31, 33-35, 37-42, or 45-54;

iv) in the case where said recombinant enzyme is not secreted from said host cell, preparing a lysate of said host cell containing said recombinant enzyme, producing an initial recombinant enzyme-containing mixture; or v) in the case where said recombinant enzyme is secreted from said host cell, harvesting culture medium in which said host cell is grown, containing said recombinant enzyme, thereby obtaining an initial recombinant enzyme-containing mixture;

vi) chromatographing said initial recombinant enzyme-containing mixture of step iv) or step v) using said chromatographic medium of step i) or step ii), as appropriate, and collecting elution fractions, thereby obtaining one or more fractions containing an enriched amount of said recombinant enzyme relative to other peptides, polypeptides, or proteins in said fraction compared to the amount of said recombinant enzyme relative to other peptides, polypeptides, or proteins in said initial protein mixture;

vii) further chromatographing an enriched fraction of step vi) to obtain said recombinant enzyme in a desired degree of purity; and viii) recovering purified recombinant enzyme.

80. The method of 79, further comprising placing said purified recombinant enzyme in a buffer solution in which said purified recombinant enzyme is stable and retains enzymatic activity.

81. The method of 80, wherein said purified recombinant enzyme-containing buffer solution is reduced to dryness.

82. The method of 81, wherein said dry purified recombinant enzyme-containing buffer solution is in the form of a powder.

83. A kit, comprising said host cell of any one of 1-54 or 68-69.

84. The kit of 83, further comprising instructions for expressing a target recombinant peptide, polypeptide, or protein in said host cell.

85. The kit of 84, wherein said target recombinant peptide, polypeptide, or protein is an endogenous or heterologous target recombinant peptide, polypeptide, or protein.

86. The kit of any one of 83-85, wherein said instructions further comprise directions for purifying said expressed target recombinant peptide, polypeptide, or protein by affinity chromatography or adsorption-based, non-affinity chromatography.

87. The kit of any one of 83-86, further comprising a chromatographic resin for affinity chromatography or adsorption-based, non-affinity chromatography.

88. A method of enriching a target peptide, polypeptide, or protein from a mixture obtained from a host cell, comprising:

a. chromatographing said mixture via affinity chromatography or adsorption-based, non-affinity chromatography;

b. collecting an elution fraction that contains an enriched amount of said target peptide, polypeptide, or protein in said fraction compared to the amount of said peptide, polypeptide, or protein of interest in said mixture; and c. recovering said target peptide, polypeptide, or protein from said elution fraction, wherein said host cell is derived from a parent cell, and has:

i) a reduced genome compared to the genome in the parent cell from which it is derived, or ii) a modified genome compared to the genome in the parent cell from which it is derived, or iii) in which expression of genes is reduced or completely inhibited compared to expression of said genes in the parent cell from which it is derived, wherein genes that are deleted, modified, or the expression of which is reduced or completely inhibited in said host cell, code for peptides, polypeptides, or proteins that impair the chromatographic separation efficiency of said target peptide, polypeptide, or protein expressed in said host cell in said affinity chromatography or said adsorption-based, non-affinity chromatography.

89. The method of 88, wherein said mixture is a lysate of said host cell in the case where said peptide, polypeptide, or protein accumulates intracellularly, or is medium in which said host cell is grown in the case where said peptide, polypeptide, or protein is secreted by said host cell.

90. The method of 88 or 89, further comprising chromatographing said target peptide, polypeptide, or protein of step c. in order to obtain said target peptide, polypeptide, or protein in a desired degree of purity.

91. The method of 90, further comprising recovering purified target peptide, polypeptide, or protein.

The methods of 88-91 encompass the use of all of the parent cells, host cells, and methods, etc., disclosed herein, and described in 1-87, above.

* * *

In a second set of embodiments, the present invention encompasses the following:

1. An *E. coli* host cell, derived from a parent *E. coli* cell, for expression of a target host cell or target recombinant peptide, polypeptide, or protein, said *E. coli* host cell comprising:

i) a reduced genome compared to the genome in the parent cell from which it is derived, and/or ii) a modified genome compared to the genome in the parent cell from which it is derived, and/or iii) in which expression of genes is reduced or completely inhibited compared to expression of said genes in the parent cell from which it is derived, wherein genes that are deleted, modified, and/or the expression of which is reduced or completely inhibited in said host cell code for peptides, polypeptides, or proteins that impair the chromatographic separation efficiency of said target host cell or target recombinant peptide, polypeptide, or protein expressed in said host cell, wherein said genes are selected from the group consisting of:
the genes listed in Table 8, and combinations thereof;
the genes listed in Table 9, and combinations thereof;
combinations of any of the genes listed in Tables 8 and 9 taken together;
the genes listed in Table 14, and combinations thereof; and
combinations of any of the genes listed in Tables 8, 9, and 14 taken together.

2. The *E. coli* host cell of 1, wherein said parent cell is an *E. coli* strain selected from the group consisting of strain K-12, strain B, strain C, strain W, and a derivative of any of the foregoing strains.

3. The *E. coli* host cell of 2, wherein:
said *E. coli* strain K-12 derivative is selected from the group consisting of W3110, DH10B, DH5alpha, DH1, MG1655, and BW2952; and
said *E. coli* strain B derivative is selected from the group consisting of B REL606, BL21, and BL21-DE3.

4. The *E. coli* host cell of any one of 1-3, wherein said parent *E. coli* cell is selected from the group consisting of:
Alpha-Select Bacteriophage T1-Resistant Gold Efficiency (F− deoR endA1 recA1 relA1 gyrA96 hsdR17(rk_, mk_+) supE44 thi-1 phoA Δ(lacZYA-argF)U169 Φ80lacZΔM15 λ−),
Alpha-Select Bacteriophage T1-Resistant Silver Efficiency (F− deoR endA1 recA1 relA1 gyrA96 hsdR17 (rk_, mk_+) supE44 thi-1 phoA Δ(lacZYA-argF)U169 Φ80lacZΔM15 λ−),
Alpha-Select Bronze Efficiency (F− deoR endA1 recA1 relA1 gyrA96 hsdR17(rk−, mk+) supE44 thi-1 phoA Δ(lacZYA-argF)U169 Φ80lacZΔM15 λ−),
Alpha-Select (F− deoR endA1 recA1 relA1 gyrA96 hsdR17(rk−, mk+) supE44 thi-1 phoA Δ(lacZYA-argF) U169 Φ80lacZΔM15 λ−),
AG1 (endA1 recA1 gyrA96 thi-1 relA1 glnV44 hsdR17 ($r_K^-$ $m_K^+$)),
AB1157 (thr-1, araC14, leuB6(Am), Δ(gpt-proA)62, lacY1, tsx-33, qsr′-0, glnV44(AS), galK2(Oc), LAM-, Rac-0, hisG4(Oc), rfbC1, mgl-51, rpoS396(Am), rpsL31(strR), kdgK51, xylA5, mtl-1, argE3(Oc), thi-1),
B2155 (thrB1004 pro thi strA hsdsS lacZD M15 (F′lacZD M15 lacI$^q$ traD36 proA$^+$proB$^+$) Δ dapA::erm (Erm$^r$) pir::RP4 [::kan (Km$^r$) from SM10]),
B834(DE3) (F−ompT hsdS$_B$($r_B^-$ $m_B^-$) gal dcm met (DE3)),
BIOBlue (recA1 endA1 gyrA96 thi-1 hsdR17(rk−, mk+) supE44 relA1 lac [F′ proAB lacI$^q$ZΔM15 Tn10(Tet$^r$)]),
BL21 (*E. coli* B F− dcm ompT hsdS($r_B^-$ $m_B^-$) gal [malB$^+$]$_{K-12}$(λ$^S$)),
BL21(AI) (F− ompT gal dcm lon hsdS$_B$($r_B^-$ $m_B^-$) araB::T7RNAP-tetA),
BL21(DE3) (F− ompT gal dcm lon hsdS$_B$($r_B^-$ $m_B^-$) λ(DE3 [lacI lacUV5-T7 gene 1 ind1 sam7 nin5])),
BL21 (DE3) pLysS (F− ompT hsdSB(rB−, mB−) gal dcm (DE3) pLysS (CamR)),
BL21-T1R (F− ompT hsdSB(rB− mB−) gal dcm tonA),
BNN93 (F− tonA21 thi-1 thr-1 leuB6 lacY1 glnV44 rfbC1 fhuA1 mcrB e14-(mcrA−) hsdR($r_K^-$$m_K^+$) λ−),
BNN97 (BNN93 (λgt11)),
BW26434 (Δ(araD-araB)567, Δ(lacA-lacZ)514(::kan), lacI$^P$-4000(lacI$^q$, λ−, rpoS396(Am)?, rph-1, Δ(rhaD-rhaB)568, hsdR514),
C600 (F− tonA21 thi-1 thr-1 leuB6 lacY1 glnV44 rfbC1 fhuA1 λ−),
CAG597 (F− lacZ(am) pho(am) tyrT[supC(ts)] trp(am) rpsL(Str$^R$) rpoH(am)165 zhg::Tn10 mal(am)),
CAG626 (F− lacZ(am) pho(am) lon trp(am) tyrT[supC (ts)] rpsL(Str$^R$) mal(am)),
CAG629 (F− lacZ(am) pho(am) lon supC(ts) trp(am) rpsL rpoH(am)165 zhg::Tn10 mal(am)),
CH3-Blue (F− ΔmcrA Δ(mrr-hsdRMS-mcrBC) Φ80lacZΔM15 ΔlacX74 recA1 endA1 ara Δ139 Δ(ara, leu)7697 galU galrpsL(Str$^R$) nupG λ−),
CSH50 (F− λ− ara Δ(lac-pro) rpsL thi fimE::IS1),
D1210 (HB101 lacI$^q$ lacY$^+$),
dam-dcm-Bacteriophage T1-Resistant (F− dam-13:Tn9 (Cam$^R$)dcm-6 ara-14 hisG4 leuB6 thi-1 lacY1 galK2 galT22 glnV44 hsdR2 xylA5 mtl-1 rpsL136(Str$^R$) rtbD1 tonA31 tsx78 mcrA mcrB1),
DB3.1 (F− gyrA462 endA1 glnV44 Δ(srl-recA) mcrB mrr hsdS20($r_B^-$, $m_B^-$) ara14 galK2 lacY1 proA2 rpsL20 (Sm$^r$) xyl5 Δleu mtl1),
DH1 (endA1 recA1 gyrA96 thi-1 glnV44 relA1 hsdR17 ($r_K^-$ $m_K^+$)) λ−),
DH5α Turbo (F′ proA+B+ lacI$^q$ Δ lacZ M15/fhuA2 Δ(lac-proAB) glnV gal R(zgb-210::Tn10)Tet$^S$ endA1 thi-1 Δ(hsdS-mcrB)5),
DH12S (mcrA Δ(mrr-hsdRMS-mcrBC) φ80d lacZΔM15 ΔlacX74 recA1 deoR Δ(ara, leu)7697 araD139 galU galK rpsL F′[proAB$^+$ lacI$^q$ZΔM15]),
DM1 (F−dam-13::Tn9(Cm$^R$) dcm-mcrB hsdR-M+ gal1 gal2 ara-lac-thr-leu-tonR tsxR Su0),
E. CLONI® 5ALPHA (fhuA2Δ(argF-lacZ)U169 phoA glnV44 Φ80 Δ(lacZ)M15 gyrA96 recA1 relA1 endA1 thi-1 hsdR17),
E. CLONI® 10G (F− mcrA Δ(mrr-hsdRMS-mcrBC) endA1 recA1 Φ80dlacZΔM15 ΔlacX74 araD139 Δ(ara,leu)7697 galU galK rpsL nupG λ− tonA (StrR)),
E. CLONI® 10GF′ ([F′ pro A+B+ lacI$^q$ZΔM15::Tn10 (Tet$^R$)]/mcrA Δ(mrr-hsdRMS-mcrBC) endA1 recA1 Φ80dlacZΔM15 ΔlacX74 araD139 Δ(ara, leu)7697 galU galK rpsL nupG λ− tonA (StrR)),
*E. coli* K12 ER2738 (F′proA+B+ lacI$^q$ Δ(lacZ)M15 zzf::Tn10(Tet$^R$)/fhuA2 glnV Δ(lac-proAB) thi-1 Δ(hsdS-mcrB)5),
ElectroMax™ DH10B (F−mcrA Δ(mrr-hsdRMS-mcrBC) Φ80lacZΔM15 ΔlacX74 recA1 endA1 araD139Δ(ara, leu)7697 galU galK λ−rpsL nupG),
ELECTROMAX™ DH5ALPHA-E (F− φ80lacZΔM15 Δ(lacZYA-argF) U169 recA1 endA1 hsdR17 (rk−, mk+) galphoA supE44 λ-thi-1 gyrA96 relA1),
ElectroSHOX (F− mcrA Δ(mrr-hsdRMS-mcrBC) Φ80lacZΔM15 ΔlacX74 recA1 ara Δ139 Δ(ara, leu)7697 galU galKrpsL(Str$^R$) nupG λ−),
EP-MAX™10B F′ (mcrA Δ(mrr-hsdRMS-mcrBC) φ80dlacZΔM15 ΔlacX74 deoR recA1 endA1 araD139 Δ(ara, leu)7697 galU galK rpsL nupG λ−/F′ [lacI$^q$ZΔM15 Tn10 (Tet$^R$)]),
ER1793 (F− fhuA2 Δ(lacZ)r1 glnV44 e14−(McrA−) trp-31 his-1 rpsL104 xyl-7 mtl-2 metB1 Δ(mcrC-mrr)114:: IS10),
ER1821 (F− glnV44 e14−(McrA−) rfbD1? relA1? endA1 spoT1? thi-1 Δ(mcrC-mrr)114::IS10),
ER2738 (F′proA$^+$B$^+$ lacI$^q$ Δ(lacZ)M15 zzf::Tn10(Tet$^R$)/ fhuA2 glnV Δ(lac-proAB) thi-1 Δ(hsdS-mcrB)5), ER2267 (F'proA$^+$B$^+$ lacI$^q$ Δ(lacZ)M15 zzf::mini-Tn10 (Kan$^R$)/Δ(argF-lacZ)U169 glnV44 e14$^-$(McrA$^-$) rfbD1? recA1 relA1? endA1 spoT1? thi-1 Δ(mcrC-mrr)114::IS10), ER2507 (F$^-$ ara-14 leuB6 fhuA2 Δ(argF-lac)U169 lacY1 glnV44 galK2 rpsL20 xyl-5 mtl-5 Δ(malB) zjc::Tn5 (Kan$^R$)Δ(mcrC-mrr)$_{HB101}$), ER2508 (F$^-$ ara-14 leuB6 fhuA2 Δ(argF-lac)U169 lacY1 lon::miniTn10(Tet$^R$) glnV44 galK2 rpsL20(Str$^R$) xyl-5 mtl-5 Δ(malB) zjc::Tn5(Kan$^R$) Δ(mcrC-mrr)$_{HB101}$), ER2738 (F'proA$^+$B$^+$ lacI$^q$ Δ(lacZ)M15 zzf::Tn10(Tet$^R$)/fhuA2 glnV Δ(lac-proAB) thi-1 Δ(hsdS-mcrB)5), ER2925 (ara-14 leuB6 fhuA31 lacY1 tsx78 glnV44 galK2 galT22 mcrA dcm-6 hisG4 rfbD1 R(zgb210::Tn10)Tet$^S$ endA1 rpsL136 dam13::Tn9 xylA-5 mtl-1 thi-1 mcrB1 hsdR2), GC5™ (: F– Φ80lacZ Δ M15 Δ (lacZYA-argF)U169 endA1 recA1 relA1 gyrA96 hsdR17 (r$_k^-$, m$_k^+$) phoA supE44 thi-1 λ-T1R), GC10 (F– mcrA Δ(mrr-hsdRMSmcrBC) Φ80dlacZ Δ M15 Δ lacX74 endA1 recA1 Δ (ara, leu)7697 araD139 galUgalK nupG rpsL λ-T1R), GENEHOGS® (FmcrA Δ(mrr-hsdRMS-mcrBC) φ80dlacZΔM15 ΔlacX74 recA1 araD139 Δ(araleu)7697 galU galK rpsL (StrR) endA1 nupG fhuA::IS2 (confers phage T1 resistance)),

HB101,

HMS174,

HMS174(DE3),

HI-CONTROL™ BL21(DE3) (F$^-$ ompT gal dcm hsdS$_B$ (r$_B^-$ m$_B^-$) (DE3)/Mini-F lacI$^{q1}$(Gent$^r$)), HI-CONTROL™ 10G (F– mcrA Δ(mrr-hsdRMS-mcrBC) endA1 recA1 Φ80dlacZΔM15 ΔlacX74araD139 Δ(ara,leu)7697 galU galK rpsL nupG λ– tonA/Mini-F lacI$^{q1}$(Gent$^r$)), HT96™ NOVABLUE (endA1 hsdR17 (r$_{K12}^-$ m$_{K12}^+$) supE44 thi-1 recA1 gyrA96 relA1 lac F'[proA$^+$B$^+$ lacI$^q$ZΔM15::Tn10] (Tet$^R$)),

IJ1126, IJ1127, INV110, JM83,

JM101 (F' traD36 proA$^+$B$^+$ lacI$^q$ Δ(lacZ)M15/Δ(lac-proAB) glnV thi),

JM103, JM105, JM106, JM107, JM108,

JM109 (F' traD36 proA$^+$B$^+$ lacI$^q$ Δ(lacZ)M15/Δ(lac-proAB) glnV44 e14$^-$ gyrA96 recA1 relA1 endA1 thi hsdR17), JM109(DE3), JM110, JS5, KS1000 (F lacI$^q$ lac$^+$ pro$^+$/ara Δ(lac-pro) Δ(tsp)=Δ(prc)::Kan$^R$ eda51::Tn10(Tet$^R$) gyrA(Nal$^R$) rpoB thi-1 argE(am)), LE392, Lemo21(DE3) (fhuA2 [lon] ompT gal (λ DE3) [dcm] ΔhsdS/pLemo(Cam$^R$) λ DE3=λ BamHIo ΔEcoRI-B int::(lack:PlacUV5::T7 gene1) i21 Δnin5 pLemo=pACYC184-PrhaBAD-lysY), LIBRARY EFFICIENCY® DH5A™ (F–ω80lacZΔM15 Δ(lacZYA-argF)U169 recA1 endA1 hsdR17(r$_k^-$, m$_k^+$) phoA supE44 thi-1 gyrA96 relA1 λ–), MACH1™T1R (F– Φ80lacZΔM15 ΔlacX74 hsdR(rK–, mK+) ΔrecA1398 endA1 tonA), MAX EFFICIENCY® DH10B™ (F-mcrA Δ(mrr-hsdRMS-mcrBC) φ80lacZΔM15 ΔlacX74 recA1 endA1 araD139 Δ(ara, leu)7697 galU galK λ-rpsL nupG/pMON14272/pMON7124), MC1061, MC4100, MDS™ 42(MG1655 fhuACDB(del) endA(del)+deletion of 699 additional genes, including all IS elements and cryptic prophages as listed in Posfai et al. (2006) Science (312):1044-1046), MFDpir, NEB Express I$^q$(MiniF lacI$^q$ (Cam$^R$)/fhuA2 [lon] ompT gal sulA11 R(mcr-73::miniTn10--Tet$^S$)2 [dcm] R(zgb-210::Tn10--Tet$^S$)endA1 Δ(mcrC-mrr)114::IS10), NEB Express, dam$^-$\dcm$^-$, NEB 5-alpha (fhuA2 Δ(argF-lacZ)U169 phoA glnV44 Φ80Δ (lacZ)M15 gyrA96 recA1 relA1 endA1 thi-1 hsdR17), NEB 10-beta (Δ(ara-leu) 7697 araD139 fhuA ΔlacX74 galK16 galE15 e14– φ80dlacZΔM15 recA1 relA1 endA1 nupG rpsL (Str$^R$) rph spoT1 Δ(mrr-hsdRMS-mcrBC)), NiCo21(DE3) (can::CBD fhuA2 [lon] ompT gal (λ DE3) [dcm] arnA::CBD slyD::CBD glmS6Ala ΔhsdS λ DE3=λ sBamHIo ΔEcoRI-B int::(lacI::PlacUV5::T7 gene1) i21 Δnin5), NM522 (F' proA$^+$B$^+$ lacI$^q$ Δ(lacZ)M15/Δ(lac-proAB) glnV thi-1 Δ(hsdS-mcrB)5), NOVABLUE™ (endA1 hsdR17 (r$_{K12}^-$ m$_{K12}^+$) supE44 thi-1 recA1 gyrA96 relA1 lac F'[proA$^+$B$^+$ lacI$^q$ZΔM15::Tn10] (Tet$^R$)), NovaF- (F$^-$endA1 hsdR17 (r$_{K12}^-$ m$_{K12}^+$) supE44 thi-1 recA1 gyrA96 relA1 lac), NOVAXGF' ZAPPERS™ (mcrA Δ(mcrC mrr) endA1 recA1 φ80dlacZΔM15 ΔlacX74araD139 Δ(ara-leu) 7697 galUgalKrpsLnupGλ$^-$tonA F'[lacI$^q$Tn10] (Tet$^R$)), OMNIMAX™2T1® (F' {proAB+ lacIq lacZΔM15 Tn10 (TetR) Δ(ccdAB)} mcrA Δ(mrr-hsdRMS-mcrBC) Φ80lacZΔM15 Δ(lacZY A-argF) U169 endA1 recA1 supE44 thi-1 gyrA96 relA1 tonA panD), ONE SHOT® BL21 STAR™ (DE3) (F–ompT hsdSB (rB–, mB–) galdcmrne131 (DE3)), ONESHOT® TOP10 (F– mcrA Δ(mrr-hsdRMS-mcrBC) Φ80lacZΔM15 Δ lacX74 recA1 araD139 Δ(araleu) 7697 galU galK rpsL (StrR) endA1 nupG), ORIGAMI™ (Δ(ara-leu)7697 ΔlacX74 ΔphoA PvuII phoR araD139 ahpC galE galK rpsLF'[lac$^+$ lacI$^q$ pro] (DE3)gor522::Tn10 trxB (Kan$^R$, Str$^R$, Tet$^R$)), ORAGAMI™ 2 (Δ(ara-leu)7697 ΔlacX74 ΔphoA PvuII phoR araD139 ahpC galE galK rpsL F'[lac$^+$ lacI$^q$ pro] gor522::Tn10 trxB (Str$^R$, Tet$^R$)), OVEREXPRESS™ C41(DE3) (F–ompT hsdSB (rB– mB–) gal dcm (DE3)), OVEREXPRESS™ C41(DE3)PLYSS (F–ompT hsdSB (rB– mB–) gal dcm (DE3) pLysS (Cm$^R$)), OVEREXPRESS™ C43(DE3) (F–ompT hsdSB (rB– mB–) gal dcm (DE3)), OVEREXPRESS™ C43(DE3)PLYSS (F–ompT hsdSB (rB– mB–) gal dcm (DE3) pLysS (Cm$^R$)), POP2136/pFOS1 (F$^-$ glnV44 hsdR17 endA1 thi-1 aroB mal$^-$ cI857 lambdaPR), PR1031 (F$^-$ thr:Tn10(Tet$^R$) dnaJ259 leu fhuA2 lacZ90 (oc) lacY glnV44 thi), ROSETTA™ (F$^-$ompT hsdS$_B$(r$_B^-$ m$_B^-$) gal dcm pRARE (Cam$^R$)), ROSETTA™(DE3)PLYSS (F$^-$ompT hsdS$_B$(r$_B^-$ m$_B^-$) gal dcm (DE3) pLysSRARE2 (Cam$^R$)), ROSETTA-GAMI™ (Δ(ara-leu)7697 ΔlacX74 ΔphoA PvuII phoR araD139 ahpC galE galK rpsL F'[lac$^+$ lacI$^q$ pro] gor522::Tn10 trxB pRARE2 (Cam$^R$, Str$^R$, Tet$^R$)), ROSETTA-GAMI™(DE3)PLYSS (Δ(ara-leu)7697 ΔlacX74 ΔphoA PvuII phoR araD139 ahpC galE galK rpsL (DE3) F'[lac$^+$ lacI$^q$ pro]gor522::Tn10 trxB pLys-SRARE2 (Cam$^R$, Str$^R$, Tet$^R$)), RR1, RV308, SCARABXPRESS® T7LAC (MDS™42 multiple-deletion strain (1) with a chromosomal copy of the T7 RNA Polymerase gene), SS320 (F'[proAB+lacIqlacZΔM15 Tn10 (tet')]hsdR mcrB araD139 Δ(araABC-leu)7679 ΔlacX74 galUgalK rpsL thi), SHUFFLE® (F' lac pro lacI$^q$/Δ(ara-leu)7697 araD13 fhuA2 Δ(lac)X74 Δ(phoA)PvuII phoR ahpC* galE (or U) galK Δλatt::pNEB3-r1-cDsbC (SpecR, lacI$^q$) ΔtrxB rpsL150(StrR) Δgor Δ(malF)3), SHUFFLE® T7 (F' lac, pro, lacI$^q$/Δ(ara-leu)7697 araD139 fhuA2 lacZ::T7 gene1 Δ(phoA)PvuII phoR ahpC* galE (or U) galK λatt:pNEB3-r1-cDsbC (Spec$^R$, lacI$^q$) ΔtrxB rpsL150(Str$^R$) Δgor Δ(malF)3), SHUFFLE® T7 EXPRESS (huA2 lacZ::T7 gene1 [lon] ompT ahpC gal λatt::pNEB3-r1-cDsbC (Spec$^R$, lacI$^q$) ΔtrxB sulA11 R(mcr-73::miniTn10--Tet$^S$)2 [dcm] R(zgb-210::Tn10--Tet$^S$) endA1 Δgor Δ(mcrC-mrr) 114::IS10), SOLR (e14-(McrA-) Δ(mcrCB-hsdSMR-mrr)171 sbcC recB recJ uvrC umuC::Tn5 (Kan$^r$) lac gyrA96 relA1 thi-1 endA1 λ$^R$ [F' proAB lacI$^q$Z ΔM15]$^C$ Su-), SCS110, STBL2™ (F– endA1 glnV44 thi-1 recA1 gyrA96 relA1 Δ(lac-proAB) mcrA Δ(mcrBC-hsdRMS-mrr)λ$^-$), STBL3™ (F– glnV44 recA13 mcrB mrr hsdS20(rB–, mB–) ara-14 galK2 lacY1 proA2 rpsL20 xyl-5 leu mtl-1), STBL4™ (endA1 glnV44 thi-1 recA1 gyrA96 relA1 Δ(lac-proAB)mcrA Δ(mcrBC-hsdRMS-mrr) λ$^-$ gal F'[proAB$^+$ lacI$^q$ lacZΔM15 Tn10]), STELLAR™ (F–, endA1, supE44, thi-1, recA1, relA1, gyrA96, phoA, Φ80d lac7Δ M15, Δ(lacZYA-argF) U169, Δ(mrr-hsdRMS-mcrBC), ΔmcrA, λ-).

SURE (endA1 glnV44 thi-1 gyrA96 relA1 lac recB recJ sbcC umuC::Tn5 uvrC e14-Δ(mcrCB-hsdSMR-mrr) 171 F'[proAB$^+$lacI$^q$ lacZΔM15 Tn10]), SURE2 (endA1 glnV44 thi-1 gyrA96 relA1 lac recB recJ sbcC umuC::Tn5 uvrC e14-Δ(mcrCB-hsdSMR-mrr) 171 F'[proAB$^+$ lacI$^q$ lacZΔM15 Tn10 Amy Cm$^R$]), T7 Express Crystal (fhuA2 lacZ::T7 gene1 [lon] ompT gal sulA11 R(mcr-73::miniTn10--Tet$^S$)2 [dcm] R(zgb-210::Tn10--Tet$^S$) endA1 metB1 Δ(mcrC-mrr)114::IS10), T7 Express lysY\I$^q$ (MiniF lysY lacI$^q$(Cam$^R$)/fhuA2 lacZ::T7 gene1 [lon] ompT gal sulA11 R(mcr-73::miniTn10--Tet$^S$)2 [dcm] R(zgb-210::Tn10--Tet$^S$) endA1 Δ(mcrC-mrr)114::IS10), T7 Express lysY (MiniF lysY (Cam$^R$)/fhuA2 lacZ::T7 gene1 [lon] ompT gal sulA11 R(mcr-73::miniTn10--Tet$^S$)2 [dcm] R(zgb-210::Tn10--Tet$^S$)endA1 Δ(mcrC-mrr)114::IS10), T7 Express I$^q$ (MiniF lacI$^q$(Cam$^R$)/fhuA2 lacZ::T7 gene1 [lon] ompT gal sulA11 R(mcr-73::miniTn10--Tet$^S$)2 [dcm] R(zgb-210::Tn10--Tet$^S$) endA1 Δ(mcrC-mrr) 114::IS10), T7 Express (fhuA2 lacZ::T7 gene1 [lon] ompT gal sulA11 R(mcr-73::miniTn10--Tet$^S$)2 [dcm] R(zgb-210::Tn10--Tet$^S$) endA1 Δ(mcrC-mrr)114::IS10), TB1 (F$^-$ ara Δ(lac-proAB) [Φ80dlac Δ(lacZ)M15] rpsL (Str$^R$) thi hsdR), TG1 (F' [traD36 proAB$^+$ lacI$^q$ lacZΔM15]supE thi-1 Δ(lac-proAB) Δ(mcrB-hsdSM)5, (r$_K^-$m$_K^-$)), THUNDERBOLT™ GC10 (F– mcrA Δ(mrr-hsdRMSmcrBC) Φ80dlacZ Δ M15 DlacX74 endA1recA1 Δ(ara, leu)7697 araD139 galU galK nupG rpsL 1λ-T1R), UT5600 (F$^-$ ara-14 leuB6 secA6 lacY1 proC14 tsx-67 Δ(ompT-fepC)266 entA403 trpE38 rfbD1 rpsL109 xyl-5 mtl-1 thi-1), VEGGIE™ BL21(DE3) (F$^-$ompT hsdS$_B$(r$_B^-$ m$_B^-$) gal dcm(DE3)), W3110 (λ857S7), WM3064, XL1-Blue (endA1 gyrA96(nal$^R$) thi-1 recA1 relA1 lac glnV44::Tn10 proAB$^+$ lacI$^q$Δ(lacZ)laM15 hsdR17(r$_K^-$ m$_K^+$)), XL1-Blue MRF'(Δ(mcrA)183 Δ(mcrCB-hsdSMR-mrr) 173 endA1 supE44 thi-1 recA1 gyrA96 relA1 lac [F' proAB lacI$^q$ZΔM15 Tn10 (Tet')]), XL2-Blue (endA1 gyrA96(nal$^R$) thi-1 recA1 relA1 lac glnV44 F'[::Tn10 proAB$^+$ lacI$^q$Δ(lacZ)M15 Amy Cm$^R$] hsdR17(r$_K^-$ m$_K^-$)), XL2-Blue MRF'(endA1 gyrA96(nal$^R$) thi-1 recA1 relA1 lac glnV44 e14- Δ(mcrCB-hsdSMR-mrr)171 recB recJ sbcC umuC::Tn5 uvrC F'[::Tn10 proAB$^+$ lacI$^q$Δ(lacZ) M15 Amy Cm$^R$]), XL1-Red (F– endA1 gyrA96(nal$^R$) thi-1 relA1 lac glnV44 hsdR17(r$_K^-$ m$_K^-$) mutS mutT mutD5 Tn10), XL10-Gold (endA1 glnV44 recA1 thi-1 gyrA96 relA1 lac Hte Δ(mcrA)183 Δ(mcrCB-hsdSMR-mrr)173 tet$^R$ F'[proAB lacI$^q$ZΔM15 Tn10(Tet$^R$ Amy Cm$^R$)]), and XL10-Gold KanR (endA1 glnV44 recA1 thi-1 gyrA96 relA1 lac Hte Δ(mcrA)183 Δ(mcrCB-hsdSMR-mrr) 173 tet$^R$ F'[proAB lacI$^q$ZΔM15 Tn10(Tet$^R$ Amy Tn5 (Kan$^R$)]).

5. The *E. coli* host cell of any one of 1-4, wherein the number of said combinations of said genes either for Table 8 alone, Table 9 alone, Tables 8 and 9 together, Table 14, or for Tables 8, 9, and 14 together is determined by combination Equation 6:

$$\frac{n!}{r!(n-r)!} \qquad \text{Equation 6}$$

wherein n is the set of genes out of which selection occurs, and r is the number of genes selected for deletion, modification, and/or inhibition.

6. The *E. coli* host cell of any one of 1-5, wherein said combinations of said genes are selected from the group consisting of:

LTSB01 (genotype: ΔhldD);
LTSB02 (genotype: ΔhldDΔusg);
LTSB03 (genotype: ΔhldDΔusgΔrraA);
LTSB04 (genotype: ΔhldDΔusgΔrraAΔcutA);
LTSB05 (genotype: ΔhldDΔusgΔrraAΔcutAΔnagD);
LTSB06 (genotype: ΔhldDΔusgΔrraAΔcutAΔnagDΔspeA);
LTSB07 (genotype: ΔhldDΔusgΔrraAΔcutAΔnagDΔspeAΔgldA);
LTSB08 (genotype: ΔhldDΔusgΔrraAΔcutAΔnagDΔspeAΔgldAΔglnA);
LTSB09 (genotype: ΔhldDΔusgΔrraAΔcutAΔnagDΔspeAΔgldAΔglnAΔmetE);
LTSB010 (genotype: ΔhldDΔusgΔrraAΔcutAΔnagDΔspeAΔgldAΔglnAΔmetEΔtgt);
LTSB011 (genotype: ΔhldDΔusgΔrraAΔcutAΔnagDΔspeAΔgldAΔglnAΔmetEΔtgtΔargG);
LTSB012 (genotype: ΔhldDΔusgΔrraAΔcutAΔnagDΔspeAΔgldAΔglnAΔmetEΔtgtΔargGΔtypA);
LTSB013 (genotype: ΔhldDΔusgΔrraAΔcutAΔnagDΔspeAΔgldAΔglnAΔmetEΔtgtΔargGΔtypAΔentF);

LTSB014 (genotype: ΔhldDΔusgΔrraAΔcutAΔnagDΔspeAΔgldAΔglnAΔmetEΔtgtΔargGΔtypAΔentFΔycaO);
LTSB015 (genotype: ΔhldDΔusgΔrraAΔcutAΔnagDΔspeAΔgldAΔglnAΔmetEΔtgtΔargGΔtypAΔentFΔycaOΔslyD);
LTSB016 (genotype: ΔhldDΔusgΔrraAΔcutAΔnagDΔspeAΔgldAΔglnAΔmetEΔtgtΔargGΔtypAΔentFΔycaOΔslyDΔgatZ);
LTSB017 (genotype: ΔhldDΔusgΔrraAΔcutAΔnagDΔspeAΔgldAΔglnAΔmetEΔtgtΔargGΔtypAΔentFΔycaOΔslyDΔgatZΔilvB);
LTSB018 (genotype: ΔhldDΔusgΔrraAΔcutAΔnagDΔspeAΔgldAΔglnAΔmetEΔtgtΔargGΔtypAΔentFΔycaOΔslyDΔgatZΔilvBΔglgP);
LTSB019 (genotype: ΔhldDΔusgΔrraAΔcutAΔnagDΔspeAΔgldAΔglnAΔmetEΔtgtΔargGΔtypAΔentFΔycaOΔslyDΔgatZΔilvBΔglgPΔnusA); and
LTSB020 (genotype: ΔhldDΔusgΔrraAΔcutAΔnagDΔspeAΔgldAΔglnAΔmet ΔtgtΔargGΔtypAΔentFΔycaOΔslyDΔgatZΔilvBΔglgPΔnusAΔmetH).

In any of the gene combinations in 6 comprising multiple genes, one or more of these genes can be omitted as long as the resulting *E. coli* host cells exhibit growth rates and/or viability and/or capacity for expression of target molecules in the range of from about 60% to about 100%, or more; or from about 70% to about 100%, or more; or from about 75% to about 100%, or more, of that of the parent cells from which they are derived, and as long as chromatographic separation capacity is improved in an amount in the range of from about 5% to about 35%, or more; from about 5% to about 40%, or more; from about 5% to about 45%, or more; from about 5% to about 50%; or more, and so on similarly, compared to that of parent cells from which they are derived, depending on the number and particular combination of genes deleted, modified, or inhibited.

In addition to these various gene omissions, these *E. coli* host cells can also further comprise (or combine in addition to these omissions) deletion, modification, and/or inhibition/reduction of expression of one or more essential genes selected from among rpoB, rpoC, tufa, ycfD, groL, prs, fusA, hemL, slyD, infB, mukB, and mt as long as the resulting *E. coli* host cells exhibit growth rates and/or viability and/or capacity for expression of target molecules in the range of from about 60% to about 100%, or more; or from about 70% to about 100%, or more; or from about 75% to about 100%, or more, of that of the parent cells from which they are derived, and as long as chromatographic separation capacity is improved in an amount in the range of from about 5% to about 35%, or more; from about 5% to about 40%, or more; from about 5% to about 45%, or more; from about 5% to about 50%; or more, and so on similarly, compared to that of parent cells from which they are derived, depending on the number and particular combination of genes modified or inhibited. Modification of these essential genes can be performed, for example, by the methods described below in the description of this disclosure, and/or could be circumvented by the feeding strategies also discussed below, depending on which essential gene(s) is(are) deleted, modified, and/or the expression of which is inhibited or reduced.

7. The *E. coli* host cell of any one of 1-6, wherein said chromatographic separation efficiency of said target host cell or target recombinant peptide, polypeptide, or protein is improved compared to the chromatographic separation efficiency of said target host cell or target recombinant peptide, polypeptide, or protein in the presence of peptides, polypeptides, or proteins coded for by said genes that are deleted, modified, and/or the expression of which is reduced or completely inhibited in said *E. coli* host cell upon affinity or adsorption, non-affinity column chromatography of said target host cell or target recombinant peptide, polypeptide, or protein.

8. The *E. coli* host cell of 7, wherein improvement of said chromatographic separation efficiency of said target host cell or target recombinant peptide, polypeptide, or protein is in the range of from about from about 5% to about 35%, or more; from about 5% to about 40%, or more; from about 5% to about 45%, or more; from about 5% to about 50%; or more, or from about 10% to about 20%, compared to chromatographic separation efficiency of said target host cell or target recombinant peptide, polypeptide, or protein in the presence of peptides, polypeptides, or proteins coded for by said genes that are deleted, modified, and/or the expression of which is reduced or completely inhibited in said *E. coli* host cell upon affinity or adsorption, non-affinity column chromatography of said target host cell or target recombinant peptide, polypeptide, or protein.

9. The *E. coli* host cell of any one of 1-8, wherein said chromatographic separation efficiency is independent of elution conditions under which said target host cell or target recombinant peptide, polypeptide, or protein emerges from an affinity or adsorption, non-affinity chromatography column as an enriched fraction.

10. The *E. coli* host cell of any one of 1-9, wherein deletion of said genes is performed by homologous recombination or frame shift mutation.

11. The *E. coli* host cell of any one of 1-9, wherein modification of said genes is performed by a method selected from the group consisting of point mutation; isozyme substitution; transposon mutagenesis; RNA-guided nucleases employing CRISPR-cas technology; and replacement by a gene from another organism that performs the same or similar function and that does not significantly adversely affect chromatographic separation efficiency and separation capacity, or growth, viability, or capacity for expression of said host cell, selected from among heterologs, homologs, analogs, paralogs, orthologs, and xenologs.

12. The *E. coli* host cell of any one of 1-9, wherein expression of said genes is reduced or completely inhibited by a method selected from the group consisting of RNA silencing, antisense oligonucleotide inhibition, and replacement of a native promoter with a weaker promoter.

13. The *E. coli* host cell of any one of 1-12, which exhibits about 5%, or more, to about 100%, or more; or from about 60% to about 100%, or more; or from about 70% to about 100%, or more; or from about 75% to about 100%, or more of the viability, growth rate, or capacity for expression of said target host cell or target recombinant peptide, polypeptide, or protein expressed in said *E. coli* host cell compared to that of said parent cell from which it is derived, or which exhibits viability, growth rate, or capacity for expression of said target host cell or target recombinant peptide, polypeptide, or protein expressed in said *E. coli* host cell greater than that of said parent cell from which it is derived.

14. The *E. coli* host cell of any one of 1-13, wherein said target host cell or target recombinant peptide, polypeptide, or protein is present in a lysate of said *E. coli* host cell, or is secreted by said *E. coli* host cell.

15. The *E. coli* host cell of any one of 1-14, wherein said target host cell or target recombinant peptide, polypeptide, or protein is an endogenous peptide, polypeptide, or protein.
16. The *E. coli* host cell of 15, wherein said endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.
17. The *E. coli* host cell of any one of 1-14, wherein said target recombinant peptide, polypeptide, or protein is a heterologous peptide, polypeptide, or protein.
18. The *E. coli* host cell of 17, wherein said heterologous peptide, polypeptide, or protein is selected from the group consisting of an enzyme and a therapeutic peptide, polypeptide, or protein.
19. The *E. coli* host cell of 18, wherein said enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and said therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, tissue plasminogen activator, and insulin.
20. The *E. coli* host cell of any one of 1-19, wherein said reduced genome compared to the genome in the parent cell from which it is derived is less than 5% smaller, less than about 4.5% smaller, less than about 4% smaller, less than about 3.5% smaller, less than about 3% smaller, less than about 2.5% smaller, less than about 2% smaller, less than about 1.5% smaller, or less than about 1% smaller, than the genome of said parent cell from which it is derived.
21. The *E. coli* host cell of any one of 1-19, wherein said reduced genome compared to the genome in the parent cell from which it is derived is between about 4.17 Mb to about 4.346 Mb.
22. The *E. coli* host cell of any one of 1-21, wherein genes that are deleted, modified, and/or the expression of which is reduced or completely inhibited in said host cell compared to expression of said genes in said parent cell from which it is derived code for proteins that impair the chromatographic separation efficiency of said target recombinant peptide, polypeptide, or protein expressed in said host cell in the presence of peptides, polypeptides, or proteins coded for by said genes that are deleted, modified, and/or the expression of which is reduced or completely inhibited in said host cell, and that elute from a chromatographic affinity column having a ligand, in a buffer comprising a compound that dictates adsorption to its respective ligand during equilibration and elution from said affinity column, in an amount in the range, in a combination selected from the group consisting of the combinations in the following table D:

TABLE D

| Ligand | Compound in Buffer That Dictates Adsorption to Affinity Column During Equilibration and Causes Elution From Column | Concentration or pH Range |
|---|---|---|
| Glutathione S-transferase | Glutathione | from about 0 mM to about 10 mM |
| Amino acid (e.g., lysine) | A common salt | from about 0 mM to about 2M |
| Amino acid | pH | from about pH 2 to about pH 11 |
| Avidin | A chaotropic salt | from about 0M to about 4M |
| Avidin | pH | from about pH 2 to about pH 10.5 |
| Carbohydrate (e.g., Dextrin) | Sugar or isocratic (e.g., maltose) | from about 0 mM to about 10 mM |
| Carbohydrate | pH | from about pH 5 to about pH 8 |
| Organic dye (e.g., Cibacron Blue) | A common salt | from about 0 mM to about 1.5M |
| Organic dye | pH | from about pH 4 to about pH 8 |
| Organic dye | Imidazole or a common salt | from about 5 mM to about 250 mM |
| Divalent metal (e.g., Ni(II)) | pH | from about pH 4 to about pH 12 |
| Divalent metal (e.g., Ni(II)) | Imidazole | from about 5 mM to about 500 mM |
| Heparin | A common salt | from about 0 mM to about 2M |
| Protein A or Protein G | Glycine | from about 0 mM to about 100 mM |
| Protein A or Protein G | pH | from about pH 3 to about pH 7 |
| IgG | Glycine | from about 0 mM to about 100 mM |
| Coenzyme | Competing Protein | from about 1 mM to about 12 mM. |

23. The *E. coli* host cell of any one of 1-21, wherein genes that are deleted, modified, and/or the expression of which is reduced or completely inhibited in said host cell compared to expression of said genes in said parent cell from which it is derived, code for proteins that impair the chromatographic separation efficiency of said target host cell or target recombinant peptide, polypeptide, or protein expressed in said host cell in the presence of peptides, polypeptides, or proteins coded for by said genes that are deleted, modified, and/or the expression of which is reduced or completely inhibited in said host cell, and that elute from a chromatographic adsorption, non-affinity column having a ligand, in a buffer comprising a compound that dictates adsorption to its respective ligand during equilibration and elution from said adsorption, non-affinity column, in an amount in the range, in a combination selected from the group consisting of the combinations in the following table:

| Ligand | Compound in Buffer That Dictates Adsorption to Non- Affinity Column During Equilibration and Causes Elution From Column | Concentration or pH Range |
|---|---|---|
| Ion exchange | Common salt | from about 0M to about 2M |
| Ion exchange | pH | from about pH 2 to about pH 12 |
| Reverse phase | Organic solvent | from about 0% to about 100% |
| Hydrophobic interaction | Common salt | from about 2M to about 0M |

24. The *E. coli* host cell of 22 or 23, wherein said common salt is selected from the group consisting of a chloride salt, a sulfate salt, an acetate salt, a carbonate salt, and a propionate salt.

25. The *E. coli* host cell of 23, wherein said organic solvent is selected from the group consisting of acetonitrile, methanol, and 2-propanol.

26. The *E. coli* host cell of any one of 1-25, wherein increased separation efficiency is manifested as increased separation capacity, increased separation selectivity, or both.

27. The *E. coli* host cell of 26, wherein separation capacity is defined as:
   i) the amount of target host cell or target recombinant peptide, polypeptide, or protein adsorbed to said column per mass lysate in the case where said target host cell or target recombinant peptide, polypeptide, or protein is not secreted, or mass culture medium in the case where said target host cell or target recombinant peptide, polypeptide, or protein is secreted, applied to said column, and separation selectivity is defined as the amount of target host cell or target recombinant peptide, polypeptide, or protein adsorbed to said column per total peptide, polypeptide, or protein adsorbed to said column, or
   ii) the amount of host cell peptides, polypeptides, or proteins adsorbed by a column per mass lysate fed to the column in the absence of expression of a target recombinant peptide, polypeptide, or protein.

28. The *E. coli* host cell of 26 or 27, wherein said increased separation capacity is in the range of from about 5% to about 35%, or more; from about 5% to about 40%, or more; from about 5% to about 45%, or more; or from about 5% to about 50%, or more.

29. The *E. coli* host cell of any one of 1-28, wherein separation of said target host cell or target recombinant peptide, polypeptide, or protein from host cell peptides, polypeptides, or proteins is performed by column chromatography employing a solid phase chromatography medium.

30. The *E. coli* host cell of 29, wherein said column chromatography is selected from the group consisting of affinity chromatography employing an affinity ligand bound to said solid phase, and adsorption-based, non-affinity chromatography.

31. The host cell of 30, wherein said affinity ligand is selected from the group consisting of an amino acid, a divalent metal ion, a carbohydrate, an organic dye, a coenzyme, glutathione S-transferase, avidin, heparin, protein A, and protein G.

32. The host cell of 31, wherein said divalent metal ion is selected from the group consisting of $Cu^{++}$, $Ni^{++}$, $Co^{++}$, and $Zn^{++}$; said carbohydrate is selected from the group consisting of maltose, arabinose, and glucose; said organic dye is a dye comprising a triazene moiety; and said coenzyme is selected from the group consisting of NADH and ATP.

33. The *E. coli* host cell of 30, wherein said adsorption-based, non-affinity chromatography is selected from the group consisting of ion exchange chromatography, reverse phase chromatography, and hydrophobic interaction chromatography.

34. The *E. coli* host cell of 33, wherein said adsorption-based, non-affinity chromatography is ion exchange chromatography.

35. The *E. coli* host cell of 34, wherein said ion exchange chromatography employs a ligand selected from the group consisting of diethylaminoethyl cellulose (DEAE), monoQ or other Q resin, and S.

36. The *E. coli* host cell of any one of 1-35, wherein said host cell peptides, polypeptides, or proteins that impair separation efficiency of said target host cell or target recombinant peptide, polypeptide, or protein expressed in said host cell are peptides, polypeptides, or proteins that are strongly retained during column chromatography.

37. The *E. coli* host cell of 36, wherein said host cell peptides, polypeptides, or proteins that are strongly retained during ion exchange chromatography are those that are retained during elution with a mobile phase comprising a common salt in the range of from about 5 mM to about 2,000 mM.

38. The *E. coli* host cell of 36, wherein said host cell peptides, polypeptides, or proteins that are strongly retained during ion exchange chromatography are those that are retained during elution with a mobile phase comprising a common salt in the range of from about 500 mM to about 1,000 mM.

39. The *E. coli* host cell of any one of 1-35, wherein said host cell peptides, polypeptides, or proteins that impair the separation efficiency of said target host cell or target recombinant peptide, polypeptide, or protein expressed in said host cell are peptides, polypeptides, or proteins that are weakly retained during column chromatography.

40. The *E. coli* host cell of 39, wherein said host cell peptides, polypeptides, or proteins that are weakly retained during chromatography are those that are retained during elution with a mobile phase comprising a common salt in the range of from about 5 mM to about 500 mM.

41. The *E. coli* host cell of 39, wherein said host cell peptides, polypeptides, or proteins that are weakly retained during chromatography are those that are retained during elution with a mobile phase comprising a common salt in the range of from about 10 mM to about 350 mM.

42. The *E. coli* host cell of any one of 1-35, wherein said host cell peptides, polypeptides, or proteins that impair the separation efficiency of said target host cell or target recombinant peptide, polypeptide, or protein expressed in said host cell are peptides, polypeptides, or proteins that are both strongly retained and weakly retained during column chromatography.

43. A method of enriching the amount of a target host cell or target recombinant peptide, polypeptide, or protein relative to other peptides, polypeptides, or proteins present in an initial protein mixture comprising said target host cell or target recombinant peptide, polypeptide, or protein, comprising the steps of:
   i) selecting a chromatography medium that binds said target host cell or target recombinant peptide, polypeptide, or protein from the group consisting of an affinity chromatography medium and an adsorption-based, non-affinity chromatography medium;
   ii) in the case where an affinity chromatography medium is selected, expressing said target host cell or target recombinant peptide, polypeptide, or protein in said *E. coli* host cell of any one of 1-22, 24, 26-32, or 36-42;
   iii) in the case where an adsorption-based, non-affinity chromatography medium is selected, expressing said target host cell or recombinant peptide, polypeptide, or protein in said *E. coli* host cell of any one of 1-21, 23-30, or 33-42; and
   iv) chromatographing said initial protein mixture comprising said target host cell or target recombinant peptide, polypeptide, or protein using said chromatography medium of step i) or step ii), as appropriate, and collecting elution fractions, thereby obtaining one or more fractions containing an enriched amount of said target host cell or target recombinant peptide, polypeptide, or protein relative to other peptides, polypeptides, or proteins in said fraction compared to the amount of said target host cell or target recombinant peptide, polypeptide, or protein relative to other peptides, polypeptides, or proteins in said initial protein mixture.

44. The method of 43, further comprising chromatographing an enriched fraction of step iv) to obtain said target host cell or target recombinant peptide, polypeptide, or protein in a desired degree of purity.

45. The method of 44, further comprising recovering said target host cell or target recombinant peptide, polypeptide, or protein.

46. A method of preparing a pharmaceutical or veterinary composition comprising a therapeutic peptide, polypeptide, or protein, comprising the steps of:
   i) selecting a chromatography medium that binds said therapeutic peptide, polypeptide, or protein from the group consisting of an affinity chromatography medium and an adsorption-based, non-affinity chromatography medium;
   ii) in the case where an affinity chromatography medium is selected, expressing said therapeutic peptide, polypeptide, or protein in said *E. coli* host cell of any one of 1-22, 24, 26-32, or 36-42;
   iii) in the case where an adsorption-based, non-affinity chromatography medium is selected, expressing said therapeutic peptide, polypeptide, or protein in said *E. coli* host cell of any one of 1-21, 23-30, or 33-42; and
   iv) in the case where said therapeutic peptide, polypeptide, or protein is not secreted from said *E. coli* host cell, preparing a lysate of said host cell containing said therapeutic peptide, polypeptide, or protein, producing an initial therapeutic peptide-, polypeptide-, or protein-containing mixture; or
   v) in the case where said therapeutic peptide, polypeptide, or protein is secreted from said *E. coli* host cell, harvesting culture medium in which said host cell is grown, containing said therapeutic peptide, polypeptide, or protein, thereby obtaining an initial therapeutic peptide-, polypeptide-, or protein-containing mixture;
   vi) chromatographing said initial therapeutic peptide-, polypeptide-, or protein-containing mixture of step iv) or step v) using said chromatography medium of step i) or step ii), as appropriate, and collecting elution fractions, thereby obtaining one or more fractions containing an enriched amount of said therapeutic peptide, polypeptide, or protein relative to other peptides, polypeptides, or proteins in said fraction compared to the amount of said therapeutic peptide, polypeptide, or protein relative to other peptides, polypeptides, or proteins in said initial protein mixture;
   vii) optionally, further chromatographing an enriched fraction of step vi) to obtain said therapeutic peptide, polypeptide, or protein in a desired degree of purity; and
   viii) recovering said therapeutic peptide, polypeptide, or protein.

Step vii) is optional, depending on the intended use of the therapeutic and regulatory agency requirements for that use, as not all treatment regimens in which therapeutics are employed require high degrees of purity, i.e., less pure preparations may suffice.

47. The method of 46, further comprising formulating said therapeutic peptide, polypeptide, or protein with a pharmaceutically or veterinarily acceptable carrier, diluent, or excipient to produce a pharmaceutical or veterinary composition, respectively.

48. The method of 46 or 47, wherein said therapeutic peptide, polypeptide, or protein is produced recombinantly in said *E. coli* host cell.

49. A method of purifying an enzyme, comprising the steps of:
   i) selecting a chromatography medium that binds said enzyme from the group consisting of an affinity chromatography medium and an adsorption-based, non-affinity chromatography medium;
   ii) in the case where an affinity chromatography medium is selected, expressing said enzyme in said *E. coli* host cell of any one of 1-22, 24, 26-32, or 36-42;
   iii) in the case where an adsorption-based, non-affinity chromatography medium is selected, expressing said enzyme in said *E. coli* host cell of any one of 1-21, 23-30, or 33-42;
   iv) in the case where said enzyme is not secreted from said *E. coli* host cell, preparing a lysate of said host cell containing said enzyme, producing an initial enzyme-containing mixture; or
   v) in the case where said enzyme is secreted from said *E. coli* host cell, harvesting culture medium in which said host cell is grown, containing said enzyme, thereby obtaining an initial enzyme-containing mixture;
   vi) chromatographing said initial enzyme-containing mixture of step iv) or step v) using said chromatographic medium of step i) or step ii), as appropriate, and collecting elution fractions, thereby obtaining one or more fractions containing an enriched amount of said enzyme relative to other peptides, polypeptides, or proteins in said fraction compared to the amount of said enzyme relative to other peptides, polypeptides, or proteins in said initial protein mixture;
   vii) optionally, further chromatographing an enriched fraction of step vi) to obtain said enzyme in a desired degree of purity; and
   viii) recovering purified enzyme.

Step vii) is optional, depending on the intended use of the enzyme, as not all processes in which enzymes are employed require high degrees of purity, i.e., "crude" enzyme preparations may suffice.

50. The method of 49, further comprising placing said purified enzyme in a buffer solution in which said purified enzyme is stable and retains enzymatic activity.

51. The method of 50, wherein said purified enzyme-containing buffer solution is reduced to dryness.

52. The method of 51, wherein said dry purified enzyme-containing buffer solution is in the form of a powder.

53. The method of any one of 49-52, wherein said enzyme is produced recombinantly in said *E. coli* host cell.

54. A kit, comprising said *E. coli* host cell of any one of 1-42.

55. The kit of 54, further comprising instructions for expressing a target host cell or target recombinant peptide, polypeptide, or protein in said *E. coli* host cell.

56. The kit of 55, wherein said target recombinant peptide, polypeptide, or protein is an endogenous or heterologous peptide, polypeptide, or protein.

57. The kit of any one of 54-56, wherein said instructions further comprise directions for purifying said expressed target host cell or recombinant peptide, polypeptide, or protein by affinity chromatography or adsorption-based, non-affinity chromatography.

58. The kit of any one of 54-57, further comprising a chromatographic resin for affinity chromatography or adsorption-based, non-affinity chromatography.
59. A method of enriching a target peptide, polypeptide, or protein from a mixture of peptides, polypeptides, or proteins obtained from an *E. coli* host cell of any one of 1-42, comprising the steps of:
   a. chromatographing said mixture via affinity chromatography or adsorption-based, non-affinity chromatography;
   b. collecting an elution fraction that contains an enriched amount of said target peptide, polypeptide, or protein in said fraction compared to the amount of said target peptide, polypeptide, or protein in said mixture; and
   c. recovering said target peptide, polypeptide, or protein from said elution fraction.
   Step c. can be optional.
60. The method of 59, wherein said mixture is a lysate of said *E. coli* host cell in the case where said target peptide, polypeptide, or protein accumulates intracellularly, or is medium in which said *E. coli* host cell is grown in the case where said target peptide, polypeptide, or protein is secreted by said host cell.
61. The method of 59 or 60, further comprising chromatographing said target peptide, polypeptide, or protein of step c. in order to obtain said target peptide, polypeptide, or protein in a desired degree of purity.
62. The method of 61, further comprising recovering purified target peptide, polypeptide, or protein.
63. The method of any one of 59-62, wherein said target peptide, polypeptide, or protein is an endogenous host cell peptide, polypeptide, or protein.
64. The method of any one of 59-62, wherein said target peptide, polypeptide, or protein is an endogenous or heterologous peptide, polypeptide, or protein that is recombinantly expressed in said *E. coli* host cell.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed descriptions taken in conjunction with the accompanying drawing(s), all of which are given by way of illustration only, and are not limitative of the present invention, in which:

FIG. 1 relates to the detailed description of the invention.

FIGS. 2, 5, and 6 relate to Example 2, Construction of the Ion Exchange Separatome of *E. coli* and Its Use to Design and Build Novel Host Strains for a Common Chromatography Resin. FIGS. 3 and 4 refer to Example 1, Identification of Host Cell Proteins Associated With a Specific Product, Histidine-Tagged Green Fluorescent Protein, as a Comparative Example.

DETAILED DESCRIPTION

Figure 1:
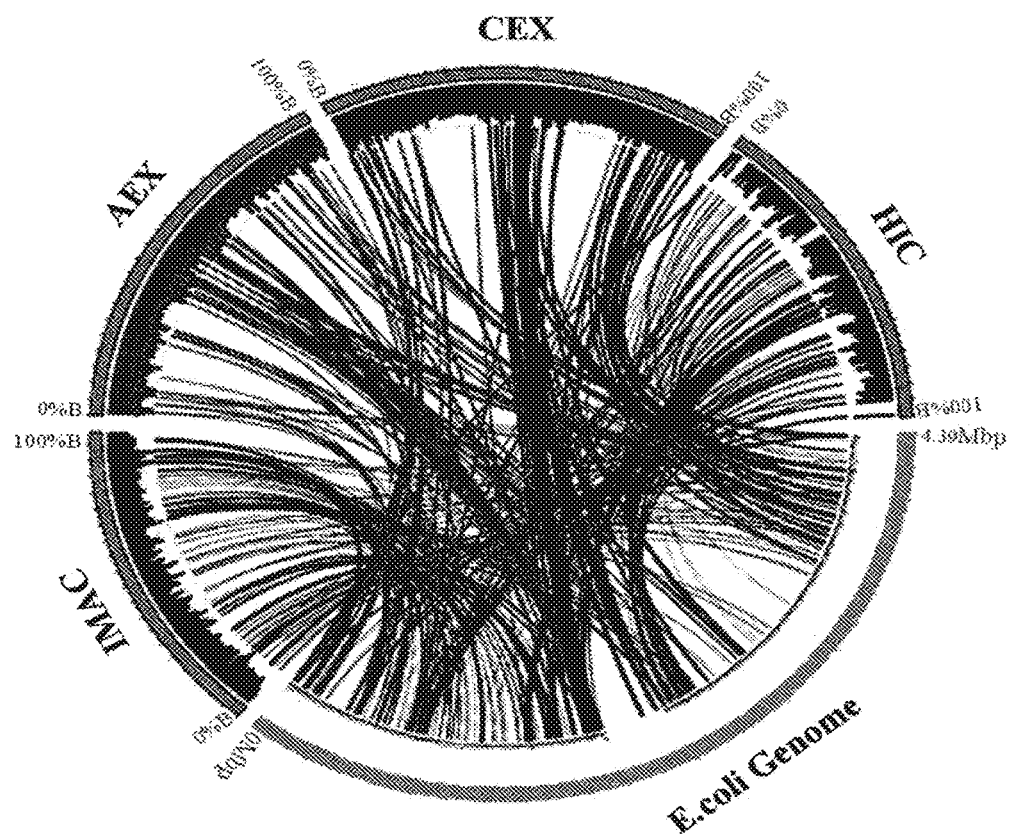
FIG. 1 shows a Circos® rendering of model data used to describe multiple separatomes. In the figure, the ring is comprised of segments that represent either gene positions or % B. Four different separatomes associated with popular methods of chromatography (IMAC, immobilized metal affinity chromatography; AEX, anion exchange chromatography; CEX, cation exchange chromatography; and HIC, hydrophobic interaction chromatography) are represented. Connecting lines map individual proteins contained within a separatome to their gene (located on the outer ring), with the concentric (inner gray) ring describing the concentration of the protein found in the fractions as they elute from a column as indicated by the length of the black bar segments. Other data that could be depicted in a Circos® rendering include gene designation, essentiality of gene product, metabolic category, or other parameter, placed on a series of concentric rings or attached to the connecting lines, for example as shown by the other concentric ring fragment.

The following detailed description is provided to aid those skilled in the art in practicing the various embodiments of the present invention. Even so, the following detailed description should not be construed to unduly limit the present invention, as modifications and variations in the embodiments herein discussed may be made by those of ordinary skill in the art without departing from the spirit or scope of the present inventive discovery.

The present disclosure is explained in greater detail below. This disclosure is not intended to be a detailed catalog of all the different ways in which embodiments of this disclosure can be implemented, or all the features that can be added to the instant embodiments. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which variations and additions do not depart from the scope of the instant disclosure. Hence, the following specification is intended to illustrate some particular embodiments of the disclosure, and not to exhaustively specify all permutations, combinations, and variations thereof encompassed by the present invention.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

By way of example, and not limitation, calculation and identification of combinations of genes useful in the E. coli host cells and methods disclosed herein, as mathematically described in Example 2, are equally applicable to the list of genes disclosed in Table 14 in Example 3.

The contents of each of the references cited herein, including journal literature and trade publications, patent applications, patents, etc., are herein incorporated by reference in their entirety. In case of conflict, the present specification, including explanations of terms, will control.

As noted above, Asenjo et al. (2004), "Is there a rational method to purify proteins? From expert systems to proteomics", *Journal of Molecular Recognition* 17:236-247, points out that, "Until now, it has been virtually impossible to select separation and purification operations for proteins either for therapeutic or analytical application in a rational manner due to lack of fundamental knowledge on the molecular properties of the materials to be separated and the lack of an efficient system to organize such information." The present methods and host cells provide solutions to this problem.

A principal consideration in the production of recombinant products, be they therapeutic molecules, enzymes for industrial or diagnostic purposes, or for other commercial applications, is the time and cost involved in purification of the biological. Downstream (post cell culture) bottlenecks present as either reduced capacity (mg target molecule captured/volume unit operation), low purification efficiency (mg target molecule captured/total mg), or combination thereof, and when they are encountered, limit the ability to screen material(s) under development or to manufacture candidate molecules. As demonstrated herein, the inventors have developed efficient alternatives to affinity chromatography via strategic changes to the E. coli host cell genome that reduce the burden imposed by the presence of host cell proteins.

The embodiments disclosed herein include a separatome-based protein expression and purification platform based on the juxtaposition of the chromatographic binding properties of genomic peptides, polypeptides, and proteins with the characteristic and location of genes on the target chromosome, such as those of E. coli, Bacillus subtilis, yeasts, and other host cells. The separatome-based protein expression and purification platform maps the separatome of target chromosomes based on relationships between the loci of genes associated with nuisance peptides, polypeptides, and proteins. In addition, the separatome-based protein expression and purification platform reduces the genome of host cells through precisely targeted modifications to create custom, robust target host strains with reduced nuisance peptides, polypeptides, and proteins. Moreover, the present separatome-based protein expression and purification platform provides a computerized knowledge tool that, given separatome data regarding a target peptide, polypeptide, or protein, intuitively suggests strategies leading to efficient purification. The separatome-based protein expression and purification platform is an efficient bioseparation system that intertwines host cell strain and chromatography.

As disclosed below in Examples 2 and 3, the inventors have identified the genes listed in Tables 8, 9, and 14 as preferred, high priority candidates for improving the chromatographic separation efficiency of target host cell or target recombinant peptides, polypeptides, or proteins expressed in the E. coli host cells disclosed herein via affinity or non-affinity, adsorption chromatography.

As exemplified by the genes listed in descending rank order of importance in Tables 8, 9, and 14 in Examples 2 and 3, importance score equation 3 identifies highly impactful E. coli parent cell HCPs that adversely affect chromatographic separation capacity. As high priority candidates for deletion, modification, or inhibition to construct improved E. coli host cell strains for target peptide, polypeptide, and protein expression and purification, it is highly likely that most, if not all, combinations of these genes will be effective in improving separation efficiency, including separation capacity, of target biomolecules from host cells in which these biomolecules are expressed and in which combinations of these nuisance genes are deleted, modified, and/or inhibited.

Preferred gene combinations for deletion, etc., are those that improve chromatographic separation capacity in the range of from about 5% to about 35%, or more; from about 5% to about 40%, or more; from about 5% to about 45%, or more; from about 5% to about 50%, or more, and so on similarly depending on the number and particular combination of genes deleted, etc., and that still permit cells to exhibit growth rates and/or viability and/or capacity for expression of target molecules in the range of from about 60% to about 100%, or more; or from about 70% to about 100%, or more; or from about 75% to about 100%, or more, compared to that of the parent cells from which they are derived. The presently disclosed methods and highly ranked genes identified out of the thousands of genes present in the E. coli genome therefore guide construction of improved E. coli host cells exhibiting improved separation capacity and satisfactory growth, viability, and capacity for expression and purification of target peptides, polypeptides, and proteins without the need for hit or miss undue experimentation within the astronomically large numbers of possible gene combinations within the E. coli genome.

The effectiveness of any of the various possible combinations of high ranking genes targeted for deletion, modification, or inhibition selected from either Table 8 alone, Table 9 alone, Table 14 alone, or any combination of these tables, in improving chromatographic separation efficiency of target host cell or target recombinant peptides, polypeptides, and proteins can easily be determined by the methods disclosed herein.

As exemplified in Example 3, collecting and interpreting data on the E. coli proteome facilitates the design and construction of an improved host cell strain that when lysed and passed over an anion exchange column displays a significant reduction in adsorption of host cell proteins (ca. 15% depending on conditions). Further development of this and other strains by the methods disclosed herein will facilitate affinity chromatography-like efficiencies with common and less expensive chromatographic matrices.

The data presented in Examples 2 and 3 demonstrate that the present separatome concept, including importance equation 3, facilitates reduction in host cell proteins (HCPs) encountered during bioprocessing, improving column capacity and overall chromatographic separation efficiency, without adversely impacting host cell growth, viability, or capacity for expression, and that this can be achieved in a rational, stepwise predictable manner Results obtained with the E. coli knockout strain LTSF06 in example 3 demonstrate that with strategic deletions, significant improvement in column efficiency can occur. Identification and ordering of several dozen high ranking genes as determined from the importance equation disclosed herein out of the thousands of genes in the E. coli genome facilitates maximum improvements in E. coli host cells used for expression of a wide range of recombinant products without having to engineer individual host cells for specific recombinant targets. While other investigations have considered knockout or mutation to improve the purity of a single recombinant product, the mathematical framework disclosed herein guides minimal changes that can be made to the E. coli genome that are useful regardless of target recombinant product. These minimal, but strategic, changes positively affect the initial chromatographic capture step, identified as a key bottleneck by biotherapeutic and enzyme manufacturers. Improved separation capacity extends the run time of the column over an increased volume of the feedstock run through the column, and improves the binding efficiency/binding selectivity of the target recombinant molecule, improving separation of the target molecule from contaminating host cell proteins.

Definitions

The following definitions are provided to aid the reader in understanding the various aspects of the present invention. Unless defined otherwise, all technical and scientific terms used herein have the same meaning as commonly understood by those of ordinary skill in the art to which the invention pertains.

As used herein and in the appended claims, the singular forms "a", "an", and "the" include plural referents unless the context clearly dictates otherwise. Thus, for example, reference to "a cell" includes one or more cells and equivalents thereof known to those skilled in the art. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary.

Regarding disclosed ranges, the endpoints of all ranges directed to the same component or property are inclusive and independently combinable (e.g., ranges of "up to about 25%, or, more specifically, about 5% to about 20%," is inclusive of the endpoints and all intermediate values of the ranges of "about 5% to about 25%," etc.). Numeric ranges recited in the specification and claims are inclusive of the numbers defining the range and include each integer within the defined range, as well as all subranges within the overall range.

"An affinity ligand" for affinity chromatography refers to a chemical moiety, coupled to a stationary phase, that serves as a biospecific sorptive group.

"Host cell" refers to a cell used to express an endogenous or heterologous nucleic acid sequence encoding a target peptide, polypeptide, or protein of interest.

"Parent cell from which it is derived" refers to a cell that is modified to then serve as a host cell of the present invention. As a non-limiting example, an E. coli parent cell can be a conventional E. coli K-12 cell. Further E. coli parent cells are disclosed below.

A host cell of the present invention can be "derived" from a parent cell by reducing the genome of the host cell compared to the genome of the parent cell from which the host cell is derived by: (a) deleting genes of the parent cell, for example by knockout mutation, or (b) modifying the genome of the host cell compared to the genome of the parent cell from which the host cell is derived, or (c) reducing or completely inhibiting expression of genes of the host cell compared to expression of these genes in the parent cell from which the host cell is derived, wherein genes that are deleted, modified, and/or the expression of which is reduced or completely inhibited in the host cell code for peptides, polypeptides, or proteins that impair the chromatographic separation efficiency of a target recombinant (or non-recombinant) peptide, polypeptide, or protein expressed in the host cell. This improves the chromatographic separation efficiency, including separation capacity, of target recombinant or non-recombinant molecules expressed in the host cell compared to that when such target molecules are expressed in the parent cell, i.e., wherein genes that are deleted, modified, and/or the expression of which is reduced or completely inhibited in the host cell are not deleted, not modified, or the expression of which is not reduced or completely inhibited in the host cell. As discussed below, identification of genes to be deleted, etc., from parent cells to produce host cells can be accomplished by employing importance equation 3. Host cells of the present invention exhibit growth rates and/or viability and/or capacity for expression of target molecules in the range of from about 60% to about 100%, or more; or from about 70% to about 100%, or more; or from about 75% to about 100%, or more, of that of the parent cells from which they are derived, and improvement in separation efficiency, including separation capacity, of target molecules in the range of from about 5% to about 35%, or more; from about 5% to about 40%, or more; from about 5% to about 45%, or more; or from about 5% to about 50%, or more compared to that of the parent cells from which they are derived. Host cells of the present invention can comprise, consist essentially of, or consist of the gene deletions, gene modifications, and/or inhibited genes disclosed herein.

The phrase "a target recombinant therapeutic peptide, polypeptide, or protein" and the like refers to a peptide, polypeptide, or protein exhibiting human or veterinary medicinal properties, expressed using recombinant nucleic acid methodology. As used herein, "medicinal properties" broadly includes not only medical therapeutic applications, but use for nutritional purposes and personal care as well.

The phrases "target host cell peptide, polypeptide or protein" or "endogenous target peptide, polypeptide or protein" and the like refer to a peptide, polypeptide, or protein native to a host cell. In various embodiments disclosed herein, such peptides, polypeptides, and proteins can be expressed in host cells either naturally, e.g., under the control of endogenous regulatory elements such as naturally occurring promoters, etc., without genetic manipulation, or by using recombinant nucleic acid methodology to improve expression levels, e.g., by replacing natural promoters with stronger ones.

Thus, it should be noted that embodiments of the present invention, including all the parent cells, host cells, methods, etc., disclosed herein, are applicable not only to the expression and purification of target host cell or endogenous target peptides, polypeptides, or proteins via recombinant methods, but also to the expression and purification of such peptides, polypeptides, and proteins that are naturally expressed within host cells, i.e., without the application of recombinant methodology.

The phrase "heterologous target recombinant peptide, polypeptide or protein" and the like refers to a peptide, polypeptide, or protein not native to a host cell, which is expressed in such cell using recombinant nucleic acid methodology.

Heterologous nucleic acid fragments encoding such peptides, etc., such as coding sequences that have been inserted into a host cell, are not normally found in the genetic complement of the host cell. As used herein, the term "heterologous" also refers to a nucleic acid fragment derived from the same host cell, but which is located in a different, e.g., non-native, location within the genome of this cell. Thus, the cell can have more than the usual number of copy(ies) of such fragment located in its(their) normal position within the genome. Heterologous nucleic acid fragments encoding recombinant peptides, polypeptides, or proteins of interest in plant cells can be expressed within different genomes within such cells, for example in the nuclear genome and within a plastid or mitochondrial genome. A nucleic acid fragment that is heterologous with respect to a cell into which it has been inserted or transferred is sometimes referred to as a "transgene."

"Essential genes" are defined by Gerdes et al. (2003) *J. Bacteria* 185(19):5673-84 as genes that are needed for cell viability when grown in LB broth. For example the enzymes in the first half of core metabolism are all considered essential; however, if the growth medium is fortified with citrate, which can directly enter the Krebs cycle, the genes coding for the enzymes preceeding the Krebs cycle can be safely deleted without detrimental effects on cell viability. When gene essentiality is defined as the genes that are needed for cell viability when grown in minimal M9+glucose as in Patrick et al. (December, 2007) *Mol Biol Evol.* 24(12):2716-22. Epub 2007 Sep. 19, all of the genes that code for enzymes in amino acid synthesis are considered essential; however, if the growth medium is fortified with these amino acids, these genes can also safely be deleted. These feeding strategies can be used in the present host cells and methods to circumvent potentially deleterious effects due to deletion, modification, and/or reduction/inhibition of expression of essential genes that would otherwise adversely impact chromatographic separation efficiency if present.

The phrase "a modified genome compared to the genome in the parent cell from which it is derived" refers to modification of genes to abate the undesirable effect(s) of the gene products on separation efficiency performed by, for example, point mutation, amino acid substitution, isozyme substitution, transposon mutagenesis, etc. As indicated, modification includes gene substitution. One example of gene modification to improve IMAC chromatography is to delete histidine residues on the surface of interfering proteins when possible. In ion exchange chromatography, one could reduce the binding affinity of nuisance proteins by altering amino acids to change protein surface charges. Modification also includes changes to essential genes that interfere with chromatographic separation efficiency by, for example, reducing their expression by replacing their naturally occurring promoters with weaker promoters, introducing strategic point mutations to replace amino acids involved in resin binding while still maintaining satisfactory levels of gene/protein activity, or replacing endogenous *E. coli* genes with genes from other organisms that perform the same or similar functions and that do not significantly adversely affect chromatographic separation efficiency and separation capacity, and cell growth, viability, and capacity for expression, rather than deleting them entirely. Such replacement genes include heterologs, homologs, analogs, paralogs, orthologs, and xenologs. These strategies facilitate improvements in chromatographic separation efficiency even when interfering host cell proteins include essential genes.

"Proteome" refers to a collection of identifiable proteins expressed by a host cell.

"Chromatotome" refers to a proteome defined by a set of host cell proteins that bind a chromatographic stationary phase.

"Separatome" refers to a proteome defined by a set of host cell proteins that are associated with a separation technique (not limited to packed bed chromatography).

"Metalloproteome" refers to a proteome with the identifying characteristic of interaction with metals or metal ions.

"Metabolome" refers to a collection of small-molecule metabolites like glucose-6-phosphate and other molecules of similar molecular weight.

"Separation efficiency" is manifested as separation capacity, separation selectivity, or both. In many cases, separation capacity is a more important parameter for the practice of the present invention.

"Separation capacity" refers to the amount of peptides, polypeptides, and/or proteins that can be captured during the loading cycle of a chromatographic separation. Separation capacity is defined as the amount of target recombinant peptide, polypeptide, or protein adsorbed by a column per mass lysate fed to the column. The present invention encompasses increases in separation capacity in the range of from about 5% to about 35%, or more, for example from about 5% to about 40%, or more; from about 5% to about 45%, or more; from about 5% to about 50%; or more, and so on similarly, depending on the number and particular combination of genes deleted, etc. Such increases reflect an advantage of the present separatome invention concept over the separation capacities achievable using standard host cells and extraction and purification methods, i.e., compared to chromatographic separation capacity of standard host cells that retain the presence of all naturally occurring peptides, polypeptides, or proteins coded for by genes that are deleted, modified, or the expression of which is reduced or completely inhibited in host cells of the present disclosure upon affinity or adsorption, non-affinity column chromatography of target recombinant peptides, polypeptides, or proteins.

While "separation capacity" is discussed above with reference to a target recombinant peptide, polypeptide, or protein, those of ordinary skill in the art will recognize that this term also more generally refers to potential improvements in chromatographic separation efficiency, including separation capacity, by the deletion, etc., of host cell peptides, polypeptides, and proteins that would interfere with the chromatographic purification of target peptides, etc., in the absence of expression of any particular target. Therefore, "separation capacity" can also be defined in terms of the amount of host cell peptides, polypeptides, or proteins adsorbed by a column per mass lysate fed to the column. Viewed from this perspective, it is clear that reducing interfering host cell peptides, polypeptides, or proteins that bind the column results in an increase in separation capacity. In the absence of expression of a particular target molecule, the potential improvement in chromatographic separation capacity is in the range of from about 5% to about 35%, or more, for example from about 5% to about 40%, or more; from about 5% to about 45%, or more; from about 5% to about 50%, or more, and so on similarly, depending on the number and particular combination of genes deleted, etc., upon affinity or adsorption, non-affinity column chromatography of the target molecule. Example 3 below demonstrates this principle by showing improved separation capacity in a modified E. coli host cell in the absence of expression of a target recombinant molecule. This example reflects the universal nature and applicability of the present host cells and methods in peptide, polypeptide, or protein purification by affinity or adsorption, non-affinity column chromatography.

In both cases, separation efficiency, including "separation capacity", is improved by the deletion, etc., of interfering host cell peptides, polypeptides, and proteins having a binding strength similar to that of the target recombinant or non-recombinant peptide, polypeptide, or protein and/or that broadly elute as % B increases.

"Separation selectivity" refers to the amount of target protein/total protein captured by a chromatographic adsorbent. Separation selectivity is defined as the amount of target recombinant peptide, polypeptide, or protein adsorbed by the column per total protein adsorbed to the column.

"Total Contaminant Pool (TCP)" refers to proteins that are known to bind to a given chromatography resin at a given pH. These proteins take up column capacity. Elimination or reduction of such proteins results in column capacity improvement.

"Eluting Contaminant Pool (ECP)" refers to proteins that are part of the TCP, but which are further grouped by their elution conditions. For example, the proteins that would co-elute with the target protein in it's specific elution window. Elimination or reduction of such proteins simplifies purification and improves target protein purity.

"HCPs" refers to host cell proteins.

"Percent B" refers to a proportion or amount, expressed as a number between 0 and 100%, of a mixture fed to a chromatography column comprised of a blend of two fluids of different compositions, i.e., composition A and composition B. A is the loading buffer, while B is the elution buffer. Percent B=100%−% A. As % B increases, the change in mobile phase composition causes proteins to be eluted in a differential fashion, beginning with those of low affinity.

"Strongly retained" refers to peptides, polypeptides, and proteins that elute from a chromatography column upon desorption due to stringent changes in mobile phase composition identified by "percent B".

"Weakly retained" refers to peptides, polypeptides, and proteins that elute from a chromatography column upon desorption due to small changes in mobile phase composition identified by "percent B".

"Common salt" refers to a compound that dissociates in water to form a cation and an anion, such as a chloride salt, a sulfate salt, an acetate salt, a carbonate salt, a propionate salt, etc., as would be apparent to one of ordinary skill in the art. Common cations in such salts are, for example, sodium, potassium, and ammonium cations.

The phrase "chromatographically relevant host cell peptides, polypeptides, or proteins for column affinity chromatography or column adsorption-based, non-affinity chromatography" refers to proteins of a separatome or chromatotome.

"Importance" or "importance score" refers to the degree to which, should a host cell peptide, polypeptide, or protein be deleted, modified, or inhibited, capacity recovery is impacted. Proteins of chromatographic relevance are considered important should large gains in capacity recovery be achieved through deletion, modification, and/or inhibition. "Important" proteins are therefore a subset of relevant proteins.

"Reduced" in the context of the level of expression of peptides, polypeptides, or proteins from host cell genes (HCPs) refers to diminution in the amount of such expression products in the range of from about 5% reduction to about 95% reduction, or more; from about 10% reduction to about 95% reduction, or more; or from about 25% reduction to about 95% reduction, or more, compared to the level of such products normally present in parent cells from which such host cells are derived.

"Scoring" or "importance scoring" refers to rank ordering members of a separatome to identify host cell peptides, polypeptides, or proteins that impair the chromatographic separation efficiency of a target recombinant peptide, polypeptide, or protein expressed in the host cell, and to establish quantitative improvements gained through their elimination.

"Operational variable" refers to a condition or operating parameter that leads to different Damkohler, Biot, or Peclet numbers used to describe a separation technique.

"Purify, purifying, purified" and the like refer to the process by which a peptide, polypeptide, or protein in a mixture is enriched so as to contain lesser amounts of materials derived from the host cell in which it is expressed, and the enriched product, respectively.

"Plant cells" includes cells of flowering and non-flowering plants, as well as algal cells, for example *Chlamydomonas, Chlorella*, etc.

Certain claims have unique formulae to mathematically define the non-metabolic aspects of the separatome, with specific regard to the overall impact a peptide, polypeptide, or protein has on column efficiency. A peptide, polypeptide, or protein elutes or emerges from a column as a peak of material, first at low concentration increasing to a maximum value, then decreasing back to zero, in the characteristic shape of a bell-like curve. The peak adopts a shape that may be described as sharp/narrow, with the majority of material of interest contained in a few fractions; broad/shallow, with the majority of material present in multiple fractions; or something in between. The time (retention time) at which the peak emerges is governed by binding strength. Peptides, polypeptides, and proteins with high affinity towards a ligand require more stringent conditions for desorption to occur, whereas those with low affinity pass through the column unretained. The ability to capture both phenomena, namely peak shape and retention time, is important to quantitatively establish the chromatographic relevance of a peptide, polypeptide, or protein. Once the relevance for a set of peptides, polypeptides, or proteins is established, molecular biology techniques are then used to delete, modify, inhibit the expression of, or substitute genes associated with these interfering molecules to directly increase column capacity and indirectly enhance purity.

Defining "recovery potential" for protein (i) first involves determining the fractional capacity occupied by this particular host cell protein by:

$$\text{recovery potential}_i = h_{i,total}/h_{total,ms} \qquad \text{Equation 1}$$

with $h_{total,ms}$=total amount of host cell proteins bound to column, and $h_{i,total}$=the bound amount attributed to (i). The value of recovery potential is bound by zero and one, with a value of one indicative of a single host cell protein, if removed from the separatome, would achieve complete recovery of the column capacity. Extending this argument to the removal of (n) proteins, the term "capacity recovery" is defined in general as:

$$\text{capacity recovery} = 100\% \times \sum_{i=1}^{n} \text{recovery potential}_i \qquad \text{Equation 2}$$

where the sigma operator allows one to sum the individual contributions for the set of (n) proteins. In the equation, n refers to number of proteins, and i is an individual protein.

These two simple relationships provide the starting point to define how much capacity can be gained as genes are deleted, modified, inhibited, or substituted. The relationships do not, however, establish order or priority within the context of peak shape and retention time. The latter is important to the disclosed invention because as mentioned previously, it is desired to focus efforts on common, problematic host cell proteins rather than those that are specific to a target recombinant product. Strongly retained or high affinity host cell proteins that are bound and that subsequently reduce column capacity would be generally problematic due to their persistent presence. Other qualifiers generally regarded as problematic would include high molecular weight (steric effects at high loading), sensitivity to proteolysis (multiple peaks or broad peak for a single protein), and propensity for subunit adsorption (multiple peaks or broad peak for a single protein). A criterion has been developed to score and rank the "importance" of a protein (i) within a separatome, i.e., the "importance score" (IS), namely:

$$\text{importance}_i = \sum_j \left[ b_1 \left(\frac{y_{c_j}}{y_{max}}\right) \left(\frac{h_{i,j}}{h_{i,total}}\right) \left(\frac{h_{i,j}}{h_{j,total}}\right) \left(\frac{MW_i}{MW_{ref}}\right)^\alpha \right]_i \qquad \text{Equation 3}$$

with the following definitions: $b_1$=scaling parameter; $y_{c_j}$ and $y_{max}$=concentration of mobile phase eluent in fraction (j) and maximum value, respectively; $h_{i,j}$ and $h_{i,total}$=the amount of protein (i) in fraction (j) and total bound protein (i), respectively; $h_{j,total}$=total amount of protein in fraction (j); $MW_i$=molecular weight of protein (i); $MW_{ref}$=molecular weight of a reference protein within the separatome; $\alpha$=steric factor; and i=protein. These ratio terms—the y's and h's—adopt values between 0 and 1, yet hold different significances. A protein that remains bound and requires stringent conditions for elution reflects a y ratio to be close to, if not equal to, unity. A protein that emerges as a tight peak presents with a ratio for h close to unity, and finally, should that emerging peak constitute the majority of fraction (j), the third ratio would be close to unity. Multiplying each ratio, and summing the product of these ratios for each fraction (j) where (i) is present provides a quantitative ranking. For example, a protein that is retained at high NaCl concentration and emerges as a sharp peak would be deemed chromatographically relevant and will be scored as high with this formula. A second example would be a protein that broadly elutes. It would also receive a high score or relevancy because its score would be high by virtue of its presence in multiple fractions.

Lastly, there requires a consideration of steric effects. As a chromatography column becomes loaded, larger proteins interact with multiple ligands either directly through adsorption, or indirectly through hindrance of binding. When steric effects require consideration, the basic equation contains a molecular weight ratio raised to a power that is descriptive of these phenomena. A unitless, non-zero alpha in the above equation, with a preferred value between 0 and 1, would indicate some degree of steric effects. Note that the general form of the importance equation also permits scale-parameters ($b_1$) to adjust the weighting of a particular score. For example, $b_1$ may be used to indicate metabolic necessity ($b_1$=0), meaning a zero value will force a low score because it likely will not be deleted from the genome. $b_1$ is unitless, and adopts a value between 0 and 1. Upon ranking the proteins in a separatome, the essentiality of a protein is determined by reference to the *E. coli* literature, e.g., Gerdes et al. (2003) *J. Bacteriol.* 185(19):5673-84. Strategies for circumventing deletion of essential proteins are described herein.

The importance score is defined in this fashion because this empirically derived equation captures the characteristics of both binding and elution data without solving numerical models of multi-component liquid chromatography to define the association and dissociation rate constants. Molecular weight is included in the importance score since it plays a role when the column is under fully loaded or breakthrough loading conditions. This ratio is raised to $\alpha$, where the $\alpha$ term accounts for column saturation, wherein when the column is fully saturated $\alpha=1$ and when the column is unsaturated $\alpha<1$. This causes the MW term to be dropped in cases where the column is not fully saturated, and thus molecular weight, or the approximate size, of the protein do not factor into overall column capacity. In the equation, the ratios of y's and h's adopt values between 0 and 1. A protein that remains bound and requires stringent conditions for elution exhibits a ratio $$\left(\frac{y_{c_j}}{y_{max}}\right)$$

close to, or equal to, unity, whereas a protein that emerges as a tight peak has $$\left(\frac{h_{i,j}}{h_{i,total}}\right)$$

ratio close to unity. Finally, a $$\left(\frac{h_{i,j}}{h_{j,total}}\right)$$

ratio is close to unity if it constitutes the majority of fraction (j).

Importance score values are between 0 and 1. "Rank" of proteins determined according to Equation 3 are relative values compared to one another.

To summarize, the basic form of the equation favors the elimination or deletion of peptides, polypeptides, or proteins that have high affinity toward the adsorbent and/or broadly elute as % B increases, with some degree of freedom to permit the tailoring of the modifications should the host cell be expressly used for a single recombinant DNA product and not a variety of products.

Commercially Important Protein Products

Exemplary, non-limiting, commercially important peptide, polypeptide, and protein products that can be expressed, recovered, and purified using the host cells, methods, and separatome information disclosed herein include, but are not limited to, the following.

Therapeutic Proteins

Examples of therapeutic human proteins that have been synthesized from genes cloned in bacteria and/or eukaryotic cells, or by expression in plants or animals, include antibodies and antigen-binding fragments; vaccines; $\alpha_1$-Antitrypsin (emphysema); deoxyribonuclease (cystic fibrosis); epidermal growth factor (ulcers); erythropoietin (anemia); Factor VIII (hemophilia); Factor IX (Christmas disease); fibroblast growth factor (ulcers); follicle stimulating hormone (infertility treatment); granulocyte colony stimulating factor (cancers); insulin (diabetes); insulin-like growth factor 1 (growth disorders); interferon-$\alpha$ (leukemia and other cancers); interferon-$\beta$ (cancers, AIDS); interferon-$\gamma$ (cancers, rheumatoid arthritis); interleukins (cancers, immune disorders); lung surfactant protein (respiratory distress); relaxin (aid in childbirth); serum albumin (plasma supplement); somatostatin (growth disorders); somatotrophin (growth disorders); superoxide dismutase (free radical damage in kidney transplants); tissue plasminogen activator (heart attack); tumor necrosis factor (cancers).

Proteins and Enzymes Used in Analytical Applications

In addition to the use of antibodies and enzymes as therapeutic agents, they are also used in the diagnosis of diseases as the components of some confirmatory tests of certain diagnostic procedures. Hexokinase and glucose oxidase are used in the quantification of glucose in the serum and urine. Glucose-oxidase is used in glucose electrodes. Uricase is used for the estimation of uric acid present in urine. Alkaline phosphatase, horseradish peroxidase, and antibodies are used in ELISA (Enzyme Linked Immunosorbent Assay).

Industrial Enzymes and Proteins

Industrially useful enzymes include carbohydrate-hydrolyzing enzymes such as amylases, cellulase, invertases, etc.; proteolytic enzymes such as papain, trypsin, chymotrypsin, etc.; and other bacterial and fungal-derived proteolytic enzymes and lipases that can hydrolyze various types of lipids and fats. All these enzymes are important in the food and beverage industries, the textile industry, paper industry, and detergent industry. Proteases have a special use in the beverage industry, meat and leather industries, cheese production, detergent industry, bread, and confectionary industry. Various types of lipases are used for the modifications of various types of lipids and fats, production of various organic acids including fatty acids, in detergents, and production of cocoa butter. In addition to all these, enzymes are used in chemical industries as reagents in organic synthesis for carrying out stereospecific reactions.

Depending on the intended use, proteins and enzymes can be employed in varying degrees of purity, i.e., highly purified preparations approaching nearly 100% purity are not always required, and therefore extensive "polishing" chromatographic steps may not be required after initial purification. Such additional steps can therefore be considered optional for particular applications.

Non-Catalytic Functional Proteins

These commercially important proteins are used in the food industry as emulsifiers, for inducing gelation, water binding, foaming, whipping, etc. These non-catalytic functional proteins are classified as whey proteins. The proteins that remain in solution after the removal of casein are by definition called whey proteins.

Commercially available whey protein concentrates contain 35% to 95% protein. If they are added to food on a solid's basis, there will be large differences in functionality due to the differences in protein content. Most food formulations call for a certain protein content and thus whey-protein concentrates are generally utilized as a constant protein base. In this case, the differences due to protein content as such should be eliminated. As the protein content increases, the composition of other components in the whey-protein concentrate must also change and these changes in composition have an effect on functionality.

Nutraceutical Proteins

Nutraceutical proteins represent a class of nutritionally-important proteins having therapeutic activity. The whey-protein concentrates and some of the milk proteins of infant foods contain certain pharmaceutical proteins having high nutritive quality. Infants get the required proteins from the mother's milk, which also contains certain therapeutic proteins that protect the baby from infection and other problems. There are other infant foods, which also have more or less the same composition as that of mother's milk, made up of cow's and buffalo's milk. All these food proteins provide the infants the raw building materials in the form of essential amino acids and at the same time protect them from microbial infections and other diseases.

Large Scale Enzyme Applications

Detergents

Bacterial proteinases are still the most important detergent enzymes. Lipases decompose fats into more water-soluble compounds. Amylases are used in detergents to remove starch based stains.

Starch Hydrolysis and Fructose Production

The use of starch degrading enzymes was the first large scale application of microbial enzymes in food industry. Mainly two enzymes carry out conversion of starch to glucose: alpha-amylase and fungal enzymes. Fructose is produced from sucrose as a starting material. Sucrose is split by invertase into glucose and fructose, and fructose is separated and crystallized.

Beverages

Enzymes have many applications in the beverage industry. Lactase splits milk-sugar lactose into glucose and galactose. This process is used for milk products that are consumed by lactose intolerant consumers. Addition of pectinase, xylanase, and cellulase improve the liberation of the juice from pulp. Similarly, enzymes are widely used in wine production.

Textiles

The use of enzymes in the textile industry is one of the most rapidly growing fields in industrial enzymology. The enzymes used in the textile field are amylases, catalase, and lactases, which are used to remove starch, degrade excess hydrogen peroxide, bleach textiles, and degrade lignin.

Animal Feed

Addition of xylanase to wheat-based broiler feed has increased the available metabolizable energy 7-10% in various studies. Enzyme addition reduces viscosity, which increases absorption of nutrients, liberates nutrients either by hydrolysis of non-degradable fibers or by liberating nutrients blocked by these fibers, and reduces the amount of feces.

Baking

Alpha-amylases have been most widely studied in connection with improved bread quality and increased shelf life. Use of xylanases decreases the water absorption, and thus reduces the amount of added water needed, in baking. This leads to more stable dough. Proteinases can be added to improve dough-handling properties; glucose oxidase has been used to replace chemical oxidants and lipases to strengthen gluten, which leads to more stable dough and better bread quality.

Pulp and Paper

The major application in the pulp and paper industry is the use of xylanases in pulp bleaching. This considerably reduces the need for chlorine based bleaching chemicals. In paper making, amylase enzymes are used especially in modification of starch. Pitch is a sticky substance present mainly in softwoods. Pitch causes problems in paper machines and can be removed by lipases.

Leather

The leather industry uses proteolytic and lipolytic enzymes in leather processing. Enzymes are used to remove unwanted parts. In dehairing and dewooling phases, bacterial proteases are used to assist the alkaline chemical process. This results in a more environmentally friendly process and improves the quality of the leather. Bacterial and fungal enzymes are used to make leather soft and easier to dye.

Specialty Enzymes

There are a large number of specialty applications for enzymes. These include the use of enzymes in analytical applications, flavor production, protein modification, personal care products, DNA-technology, and in fine chemical production.

Enzymes in Analytics

Enzymes are widely used in clinical analytical methodology. Contrary to bulk industrial enzymes, these enzymes need to be free from side activities. This means that elaborate purification processes are needed.

An important development in analytical chemistry is biosensors. The most widely used application is a glucose biosensor involving glucose oxidase catalyzed reaction. Several commercial instruments are available which apply this principle for measurement of molecules like glucose, lactate, lactose, sucrose, ethanol, methanol, cholesterol, and some amino acids.

Enzymes in Personal Care Products

Personal care products are a relatively new area for enzymes. Proteinase and lipase containing enzyme solutions are used for contact lens cleaning. Hydrogen peroxide is used in disinfections of contact lenses. The residual hydrogen peroxide after disinfections can be removed by catalase. Some toothpaste contains glucoamylase and glucose oxidase. Enzymes are also being studied for applications in skin and hair care products.

Enzymes Used in DNA-Technology

DNA-technology is an important tool in the enzyme industry. Most traditional enzymes are produced by organisms that have been genetically modified to overproduce desired enzymes. Recombinant DNA methodology has been used to engineer overproducing microorganisms, and employs enzymes such as nucleases (especially restriction endonucleases), ligases, polymerases, and DNA-modifying enzymes to modify genes and construct necessary expression cassettes and vectors.

Enzymes in Fine Chemical Production

In spite of some successes, commercial production of chemicals by living cells via pathway engineering is still in many cases the best alternative to apply biocatalysis. Isolated enzymes have, however, been successfully used in fine chemical synthesis. Some of the most important examples are:

Chirally Pure Amino Acids and Aspartame

Natural amino acids are usually produced by microbial fermentation. Novel enzymatic resolution methods have been developed for the production of L- and D-amino acids. Aspartame, the intensive non-calorie sweetener, is synthesized in non-aqueous conditions by thermolysin, a proteolytic enzyme.

Rare Sugars

Recently, enzymatic methods have been developed to manufacture practically all D- and L-forms of simple sugars. Glucose isomerase is one of the important industrial enzymes used in fructose manufacturing.

Semisynthetic Penicillins

Penicillin is produced by genetically modified strains of *Penicillium* strains. Most of the penicillin is converted by immobilized acylases to 6-aminopenicillanic acid, which serves as a backbone for many semisynthetic penicillins.

Lipase-Based Reactions

In addition to detergent applications, lipases can be used in versatile chemical reactions since they are active in organic solvents. Lipases are used in transesterification, for enantiomeric separation of alcohols, and for the separation of racemic mixtures. Lipases have also been used to form aromatic and aliphatic polymers.

Enzymatic Oligosaccharide Synthesis

The chemical synthesis of oligosaccharides is a complicated multi-step effort. Biocatalytic syntheses with isolated enzymes like glycosyltransferases and glycosidases or engineered whole cells are powerful alternatives to chemical methods. Oligosaccharides have found applications in cosmetics, medicines and as functional foods.

Overview

Disclosed herein is a separatome-based host cell peptide, polypeptide, and protein expression and purification platform focusing on the proteomes of various chromatographic methods to provide a single host cell line, or set of host cell lines, that can be used for expression of a wide variety of recombinant peptides, polypeptides, and proteins, thereby eliminating the need to develop individual host cell lines for each purification process.

The "separatome" of the present separatome-based protein expression and purification platform involves the juxtaposition of the binding properties of host cell peptides, polypeptides, and proteins in common chromatographic techniques (e.g., IMAC, IEX, and/or HIC) with the characteristics and location of the corresponding encoding genes on the target host cell chromosome(s). While the examples of the separatome-based protein expression and purification platform disclosed herein focus on *Escherichia coli* as the host cell, and its chromatotome, the invention is not limited thereto as the separatome-based peptide, polypeptide, and protein expression and purification platform can extend to any suitable host conventionally used for recombinant expression, such as *Lactococcus lactis*, *Bacillus* species such as *B. licheniformis*, *B. amyloliquefaciens*, and *B. subtilis*, *Corynebacterium glutamicum*, *Pseudomonas fluorescens*, or other prokaryotes; fungi, including various yeasts such as *Saccharomyces cerevisiae*, *Pichia* (now K.) *pastoris*, and *Pichia methanolica*; insect cells; mammalian cells; plant cells, including for example, tobacco (e.g., cultivars BY-2 and NT-1), alfalfa, rice, tomato, soybean, as well as algal cells; and protozoal cells such as the non-pathogenic strain of *Leishmania tarentolae*, etc.

The present separatome-based peptide, polypeptide, and protein expression and purification platform is an efficient bioseparation system that intertwines host cell strain and chromatography. Since the high cost of product purification often limits the availability of therapeutic proteins of interest to immunology, vaccine development, pharmaceutical production, and diagnostic reagents, as well as the availability of enzymes for various applications, the present separatome-based peptide, polypeptide, and protein expression and purification platform provides alternative pathways towards efficient purification based on the utilization of proteome data. In particular, the separatome-based protein expression and purification platform provides for: (i) a system of chromatographic data based on identified, conserved genomic regions that span resin- and gradient-specific chromatographies, or chromatotomes, for example, a database of *E. coli* proteins that span the chromatography total contaminant pool (TCP)/elution contaminant pool (ECP) and bind under various conditions to a variety of chromatographic resins; (ii) a process to minimize contaminant pools of nuisance or coeluting proteins associated with specific chromatographies, for example, gradients that substantially decrease the number of coeluting proteins encountered during bioseparation, and the specific, targeted deletion of nuisance host cell peptide-, polypeptide-, and protein-encoding genes to minimize contaminant pools associated with affinity adsorption and non-affinity adsorption chromatographies, including IMAC, cation IEX, anion IEX, HIC, and combinations thereof.

The separatome-based peptide, polypeptide, and protein expression and purification platform is constructed based upon a computer system of identified, conserved genomic regions that span resin- and gradient specific-chromatographies, or chromatotomes. The computer system includes a data visualization program/application resident on a standard computer device, such as a mainframe, desktop, or other computer. For example, the computer may have a central processor that controls the overall operation of the computer and a system bus that connects the central processor to one or more conventional components, such as a network card or modem. The computer may also include a variety of interface ports and drives for reading and writing data or files. A user of the separatome-based protein expression and purification platform can interact with the computer with a keyboard, pointing device, microphone, pen device, or other input device. The computer may be connected via a suitable network connection, such as a Ti line, a common local area network ("LAN"), via the worldwide web, or via other mechanism for connecting computer devices.

Figure 2:
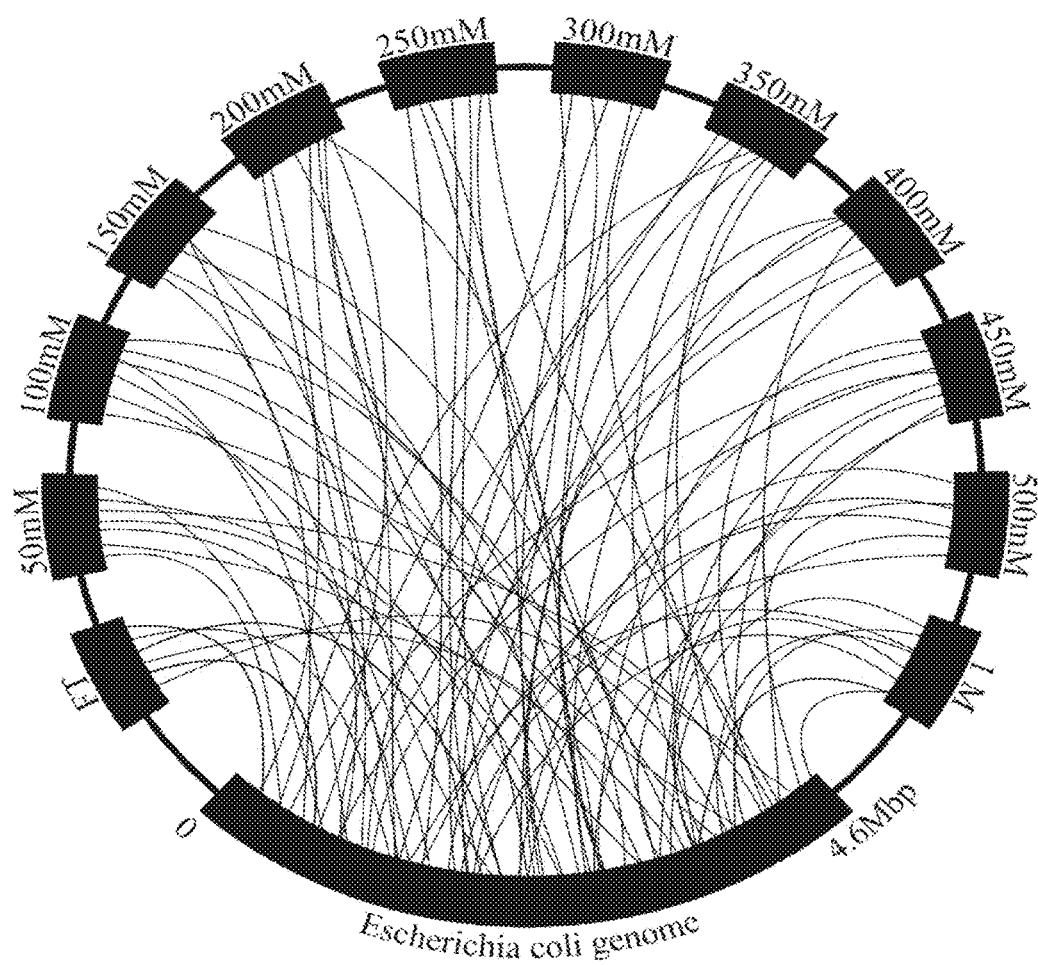
FIG. 2 shows a Circos® rendering of model data describing the separatome of *E. coli* for ion exchange chromatography. Similar to FIG. 1 is the use of connecting lines that indicate genes associated with proteins found in the separatome of *E. coli* for a particular resin/equilibrating condition. However, this rendering provides detail as to the elution fraction by connecting a gene to a particular box on the ring that represents a salt concentration. The lower black fragment of the circle entitled "*Escherichia coli* genome" can contain the location of genes present on the *E. coli* chromosome. Each box represents a different cut from a column.

The separatome-based peptide, polypeptide, and protein expression and purification platform will utilize large amounts of data compiled on the metalloproteome and metabolome of the selected host cell, such as *E. coli*. The data visualization program/application, such as Circos®, a software package for visualizing data and information in a circular layout (available from Canada's Michael Smith Genome Sciences Center), enables the user to visualize the large amounts of data and information for exploring relationships between objects or positions. FIGS. 1 and 2 illustrates examples of how the data visualization program/application could illustrate the *E. coli* chromosome mapped with the chromatotome of multiple chromatographic techniques, thus showing where the different chromatotomes lie within the greater genome. Each line in FIG. 1 represents a single contaminating protein, and the graph at its base shows the total concentration of the protein as a percent of the TCP or ECP. If each TCP is subdivided into its respective ECPs, then further corollaries can be drawn between proteins and genomic location. Further, segments of the ring represent the *E. coli* genome or the proteome associated with a particular isolation technique. With respect to *E. coli*, inner rings can represent additional information like essentiality, successful deletion, metabolic function, etc. For a given chromatographic technique, inner ring data can represent conditions that trigger adsorption or elution, concentration in the extract, and if this protein is differentially expressed during stress.

In addition, the separatome-based peptide, polypeptide, and protein expression and purification platform may utilize and/or incorporate data about the target genome and proteome sequences, such as from Ecogene® (Institute for Advanced Biosciences, Keio University and Integrated Genomics, Chicago, Ill.). The data visualization program/application of the separatome-based protein expression and purification platform provides the user a feasible means of utilizing the data by melding it into a productive format, and in particular, the data visualization program/application provides the ability to visually summarize large collections of data covering peptides, polypeptides, and proteins encountered in the chromatotome and their essentiality.

The mapping and plotting of the IMAC, IEX and HIC data by the separatome-based peptide, polypeptide, and protein expression and purification platform allows for the identification of large contiguous regions of contaminants from several chromatography techniques that may be targeted for modification if necessary.

Since the overall structure of a target recombinant peptide, polypeptide, or protein and the column resin are usually fixed constraints, a reduction in contaminant species has the ability to improve chromatographic recovery and purification via elimination of undesirable binding events. Overall reduction of contaminant species, including undesired host cell peptides, polypeptides, and proteins, can be achieved by removal, modification, or inhibition of the expression of the genomic regions coding for the contaminants.

General Methods

Practice of the various embodiments of the present invention employs, unless otherwise indicated, conventional techniques of molecular biology, recombinant DNA technology, microbiology, chemistry, etc., which are well known in the art and within the capabilities of those of ordinary skill in the art. Such techniques include the following non-limiting examples: preparation of cellular, plasmid, and bacteriophage DNA; manipulation of purified DNA using nucleases, ligases, polymerases, and DNA-modifying enzymes; introduction of DNA into living cells; cloning vectors for various organisms; PCR; gene deletion, modification, replacement, or inhibition; production of recombinant peptides, polypeptides, and proteins in host cells; chromatographic methods; etc.

Such methods are well known in the art and are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; Amberg et al. (2005) *Methods in Yeast Genetics: A* Cold Spring Harbor Laboratory Course Manual, 2005 Edition, Cold Spring Harbor Laboratory Press; Roe et al. (1996) *DNA Isolation and Sequencing: Essential Techniques*, John Wiley & Sons; J. M. Polak and James O'D. McGee (1990) *In Situ Hybridization: Principles and Practice*; Oxford University Press; M. J. Gait (Editor) (1984) *Oligonucleotide Synthesis: A Practical Approach*, IRL Press; D. M. J. Lilley and J. E. Dahlberg (1992) *Methods in Enzymology: DNA Structure Part A: Synthesis and Physical Analysis of DNA*, Academic Press; and *Lab Ref: A Handbook of Recipes, Reagents, and Other Reference Tools for Use at the Bench*, Edited by Jane Roskams and Linda Rodgers (2002) Cold Spring Harbor Laboratory Press; Burgess and Deutscher (2009) *Guide to Protein Purification*, Second Edition (*Methods in Enzymology*, Vol. 463), Academic Press. Note also U.S. Pat. Nos. 8,178,339; 8,119,365; 8,043,842; 8,039,243; 7,303,906; 6,989,265; US20120219994A1; and EP1483367B1. The entire contents of each of these texts and patent documents is herein incorporated by reference.

Designations of *E. coli* genes change from time to time or are referred to by different names in different laboratories. For example, hldD is also known as rfaD. Any discrepancies between the *E. coli* gene designations disclosed herein and updated designations can be ascertained from EcoCyc ([EcoCyc13] Keseler et al. (2013) EcoCyc: fusing model organism databases with systems biology. *Nucleic Acids Research* 41:D605-612 and EcoGene (Zhou et al. (2013) EcoGene 3.0 *Nucleic Acids Research*, 41 (D1): D613-D624.), which are curated *E. coli* databases well known in the art.

Methods for Deleting, Modifying, and Inhibiting the Expression of Genes in *E. coli*

Baba et al. (2006) *Mol. Syst. Biol.* 2:2006.0008, doi: 10.1038/msb4100050, discloses methods for making precisely defined single gene deletions in *E. coli*.

Datsenko et al. (2000) *Proc. Natl. Acad. Sci. USA*. 97(12): 6640-5 discloses methods for inactivating chromosomal genes in *E. coli* using PCR products.

Stringer et al. (2012) *PLoS ONE* 7(9): e44841. doi: 10.1371/journal.pone.0044841 discloses a rapid, efficient, PCR-based recombineering method that can be used to introduce scar-free point mutations, deletions, epitope tags, and promoters into the genomes of multiple species of enteric bacteria.

Le Cong et al. (2013) *Science* 339:819-823; Jiang et al. (2013) *Nature Biotechnology* 31(3):233-239; Mali et al. (2013) *Nature Methods* 10(10):957-963; Sander et al. (2014) *Nature Biotechnology* 32(4):347-355; and U.S. Pat. No. 8,697,359 disclose CRISPR-Cas systems for editing, regulating, and targeting genomes.

Methods for RNA silencing and antisense oligonucleotide inhibition of gene expression are well known in the art. Note, for example, the reviews in *Nature* (2009) 457, No. 7228, pp. 395-433 and *Molecular Cancer Therapeutics* (2002) 1:347-355, respectively.

*E. coli* gene essentiality data can be retrieved from Gerdes et al. (2003) *J. Bacteriol.* 185(19):5673-84) which compiles gene essentiality from their own research as well as the Profiling of *E. coli* Chromosome (PEC) database (Hashimoto et al. (2005) *Molecular Microbiology* 55(1): 137-49; Kato and Hashimoto (2007) *Molecular Systems Biology* 3(132):132; and Kang Y et. al. (2004) *J. Bacteriol.* 186(15):4921-30). Such data can also be determined empirically.

Frequently Used Expression Systems for Foreign Genes

Yin et al. (2007) *Journal of Biotechnology* 127(3):335-347 reviews the most frequently used expression systems for foreign genes.

Baneyx (1999) *Curr. Opin. Biotechnol.* 10(5): 411-2ldescribes protein production in frequently used host cell systems.

Examples of specific *E. coli* parent and host cells useful in the present invention include the following. These listings should not be construed to be limiting as other *E. coli* host cells known in the art are also useful in embodiments of the present methods, and are encompassed herein.

TABLE 1

References Disclosing *E. coli* Strain Genomic Sequences

| Table Entry Number | *E. coli* Strain Number | Reference (Source of Genomic Sequence) | Genome Size (Mb) |
|---|---|---|---|
| 1 | *E. coli* K-12 | Blattner F R, et al. *Science* 1997 Sep. 5; 277(5331):1453-62. | 4.639 |
| 2 | *E. coli* MG1655 | Blattner F R, et al. *Science* 1997 Sep. 5; 277(5331): 1453-62. | 4.639 |

TABLE 1-continued

References Disclosing *E. coli* Strain Genomic Sequences

| Table Entry Number | *E. coli* Strain Number | Reference (Source of Genomic Sequence) | Genome Size (Mb) |
|---|---|---|---|
| 3 | *E. coli* BL21 (DE3) | Jeong H m et al. *J Mol Biol* 2009 Dec. 11; 394(4): 644-52 | 4.56 |
| 4 | *E. coli* DH10B | Durfee et al. *J Bacteriol*. 2008 April; 190(7): 2597-606 | 4.69 |

As indicated in Table 1, *E. coli* strains useful in various embodiments of the present invention include K-12 and B strains. C and W strains are also useful. Derivatives and substrains of all of these strains, as are known to those of ordinary skill in the art, are also useful.

Useful K-12 derivatives include, but are not limited to, strains such as W3110, DH10B, DH5alpha, DH1, MG1655, BW2952, and their derivatives.

Useful B strain derivatives include, but are not limited to, B REL606, BL21, BL21-DE3, and their derivatives.

Other useful *E. coli* strains include, but are not limited to, the following, including their derivatives and substrains:

Alpha-Select Bacteriophage T1-Resistant Gold Efficiency (F– deoR endA1 recA1 relA1 gyrA96 hsdR17(rk_, mk_+) supE44 thi-1 phoA Δ(lacZYA-argF)U169 Φ80lacZΔM15 λ–), Alpha-Select Bacteriophage T1-Resistant Silver Efficiency (F– deoR endA1 recA1 relA1 gyrA96 hsdR17 (rk_, mk_+) supE44 thi-1 phoA Δ(lacZYA-argF)U169 Φ80lacZΔM15 λ–), Alpha-Select Bronze Efficiency (F– deoR endA1 recA1 relA1 gyrA96 hsdR17(rk–, mk+) supE44 thi-1 phoA Δ(lacZYA-argF)U169 Φ80lacZΔM15 λ–), Alpha-Select (F– deoR endA1 recA1 relA1 gyrA96 hsdR17(rk–, mk+) supE44 thi-1 phoA Δ(lacZYA-argF) U169 Φ80lacZΔM15 λ–), AG1 (endA1 recA1 gyrA96 thi-1 relA1 glnV44 hsdR17 ($r_K^-$ $m_K^+$)), AB1157 (thr-1, araC14, leuB6(Am), Δ(gpt-proA)62, lacY1, tsx-33, qsr'-0, glnV44(AS), galK2(Oc), LAM-, Rac-0, hisG4(Oc), rfbC1, mgl-51, rpoS396(Am), rpsL31(strR), kdgK51, xylA5, mtl-1, argE3(Oc), thi-1), B2155 (thrB1004 pro thi strA hsdsS lacZD M15 (F'lacZD M15 lacI$^q$ traD36 proA$^+$proB$^+$) Δ dapA::erm (Erm$^r$) pir::RP4 [::kan (Km$^r$) from SM10]), B834(DE3) (F$^-$ompT hsdS$_B$($r_B^-$ $m_B^-$) gal dcm met (DE3)), BIOBlue (recA1 endA1 gyrA96 thi-1 hsdR17(rk–, mk+) supE44 relA1 lac [F' proAB lacI$^q$ZΔM15 Tn10(Tet$^r$)]), BL21 (*E. coli* B F– dcm ompT hsdS($r_B^-$ $m_B^-$) gal [malB$^+$]$_{K-12}$(λ$^S$)), BL21(AI) (F$^-$ ompT gal dcm lon hsdS$_B$($r_B^-$ $m_B^-$) araB:: T7RNAP-tetA), BL21(DE3) (F$^-$ ompT gal dcm lon hsdS$_B$($r_B^-$ $m_B^-$) λ(DE3 [lacI lacUV5-T7 gene 1 ind1 sam7 nin5])), BL21 (DE3) pLysS (F– ompT hsdS$_B$(rB—, mB—) gal dcm (DE3) pLysS (CamR)), BL21-T1R (F– ompT hsdSB(rB– mB–) gal dcm tonA), BNN93 (F$^-$ tonA21 thi-1 thr-1 leuB6 lacY1 glnV44 rfbC1 fhuA1 mcrB e14-(mcrA$^-$) hsdR($r_K^-$ $m_K^+$) λ$^-$), BNN97 (BNN93 (λgt11)), BW26434 (Δ(araD-araB)567, Δ(lacA-lacZ)514(::kan), lacI$^P$-4000(lacI$^q$), λ$^-$, rpoS396(Am)?, rph-1, Δ(rhaD-rhaB)568, hsdR514), C600 (F$^-$ tonA21 thi-1 thr-1 leuB6 lacY1 glnV44 rfbC1 fhuA1 λ$^-$), CAG597 (F$^-$ lacZ(am) pho(am) tyrT[supC(ts)] trp(am) rpsL(Str$^R$) rpoH(am)165 zhg::Tn10 mal(am)), CAG626 (F$^-$ lacZ(am) pho(am) lon trp(am) tyrT[supC (ts)] rpsL(Str$^R$) mal(am)), CAG629 (F$^-$ lacZ(am) pho(am) lon supC(ts) trp(am) rpsL rpoH(am)165 zhg::Tn10 mal(am)), CH3-Blue (F– ΔmcrA Δ(mrr-hsdRMS-mcrBC) Φ80lacZΔM15 ΔlacX74 recA1 endA1 ara Δ139 Δ(ara, leu)7697 galU galrpsL(Str$^R$) nupG) λ$^-$), CSH50 (F$^-$ λ$^-$ ara Δ(lac-pro) rpsL thi fimE::IS1), D1210 (HB101 lacI$^q$ lacY$^+$), dam-dcm-Bacteriophage T1-Resistant (F– dam-13:Tn9 (Cam$^R$)dcm-6 ara-14 hisG4 leuB6 thi-1 lacY1 galK2 galT22 glnV44 hsdR2 xylA5 rpsL136(Str$^R$) rtbD1 tonA31 tsx78 mcrA mcrB1), DB3.1 (F– gyrA462 endA1 glnV44 Δ(srl-recA) mcrB mrr hsdS20($r_B^-$, $m_B^-$) ara14 galK2 lacY1 proA2 rpsL20 (Sm$^r$) xyl5 Δleu mtl1), DH1 (endA1 recA1 gyrA96 thi-1 glnV44 relA1 hsdR17 ($r_K^-$ $m_K^+$)) λ$^-$), DH5α Turbo (F' proA+B+lacI$^q$ Δ lacZ M15/fhuA2 Δ(lac-proAB) glnV gal R(zgb-210::Tn10)Tet$^S$ endA1 thi-1 Δ(hsdS-mcrB)5), DH12S (mcrA Δ(mrr-hsdRMS-mcrBC) φ80d lacZΔM15 ΔlacX74 recA1 deoR Δ(ara, leu)7697 araD139 galU galK rpsL F' [proAB$^+$ lacI$^q$ZΔM15]), DM1 (F– dam-13::Tn9(Cm$^R$) dcm-mcrB hsdR-M+gal1 gal2 ara-lac-thr-leu-tonR tsxR Su0), E. CLONI® 5ALPHA (fhuA2Δ(argF-lacZ)U169 phoA glnV44 D80 Δ(lacZ)M15 gyrA96 recA1 relA1 endA1 thi-1 hsdR17), E. CLONI® 10G (F– mcrA Δ(mrr-hsdRMS-mcrBC) endA1 recA1 Φ80dlacZΔM15 ΔlacX74 araD139 Δ(ara,leu)7697galU galK rpsL nupG λ– tonA (Str$^R$)), E. CLONI® 10GF' ([F'pro A+B+lacI$^q$ZΔM15::Tn10 (Tet$^R$)]/mcrA Δ(mrr-hsdRMS-mcrBC) endA1 recA1 Φ80dlacZΔM15 ΔlacX74 araD139 Δ(ara, leu)7697 galU galK rpsL nupG λ– tonA (Str$^R$)),

*E. coli* K12 ER2738 (F'proA+B+lacI$^q$ Δ(lacZ)M15 zzf:: Tn10(Tet$^R$)/fhuA2 glnV Δ(lac-proAB) thi-1 Δ(hsdS-mcrB)5), ElectroMax™ DH10B (F$^-$ mcrA Δ(mrr-hsdRMS-mcrBC) Φ80lacZΔM15 ΔlacX74 recA1 endA1 araD139Δ(ara, leu)7697 galU galK λ$^-$rpsL nupG), ELECTROMAX™ DH5ALPHA-E (F– φ80lacZΔM15 Δ(lacZYA-argF) U169 recA1 endA1 hsdR17 (rk–, mk+) galphoA supE44 λ-thi-1 gyrA96 relA1), ElectroSHOX (F– mcrA Δ(mrr-hsdRMS-mcrBC) Φ80lacZΔM15 ΔlacX74 recA1 endA1 ara Δ139 Δ(ara, leu)7697 galU galKrpsL(Str$^R$) nupG λ$^-$), EP-MAX™10B F' (mcrA Δ(mrr-hsdRMS-mcrBC) φ80dlacZΔM15 ΔlacX74 deoR recA1 endA1 araD139 Δ(ara, leu)7697 galU galK rpsL nupG λ–/F [lacI$^q$ZΔM15 Tn10 (Tet$^R$)]), ER1793 (F$^-$ fhuA2 Δ(lacZ)r1 glnV44 e14$^-$(McrA$^-$) trp-31 his-1 rpsL104 xyl-7 mtl-2 metB1 Δ(mcrC-mrr)114:: IS10), ER1821 (F$^-$ glnV44 e14$^-$(McrA$^-$) rfbD1? relA1 ? endA1 spoT1? thi-1 Δ(mcrC-mrr)114::IS10), ER2738 (F' proA$^+$B$^+$ lacI$^q$ Δ(lacZ)M15 zzf::Tn10(Tet$^R$)/ fhuA2 glnV Δ(lac-proAB) thi-1 Δ(hsdS-mcrB)5), ER2267 (F'proA$^+$B$^+$ lacI$^q$ Δ(lacZ)M15 zzf::mini-Tn10 (Kan$^R$)/Δ(argF-lacZ)U169 glnV44 e14$^-$(McrA$^-$) rfbD1? recA1 relA1? endA1 spoT1? thi-1 Δ(mcrC-mrr) 114::IS10), ER2507 (F⁻ ara-14 leuB6 fhuA2 Δ(argF-lac)U169 lacY1 glnV44 galK2 rpsL20 xyl-5 mtl-5 Δ(malB) zjc::Tn5 (Kan$^R$)Δ(mcrC-mrr)$_{HB101}$), ER2508 (F⁻ ara-14 leuB6 fhuA2 Δ(argF-lac)U169 lacY1 lon::miniTn10(Tet$^R$) glnV44 galK2 rpsL20(Str$^R$) xyl-5 mtl-5 Δ(malB) zjc::Tn5(Kan$^R$) Δ(mcrC-mrr)$_{HB101}$), ER2738 (F'proA⁺B⁺ lacI$^q$ Δ(lacZ)M15 zzf::Tn10(Tet$^R$)/ fhuA2 glnV Δ(lac-proAB) thi-1 Δ(hsdS-mcrB)5), ER2925 (ara-14 leuB6 fhuA31 lacY1 tsx78 glnV44 galK2 galT22 mcrA dcm-6 hisG4 rfbD1 R(zgb210::Tn10)Tet$^S$ endA1 rpsL136 dam13::Tn9 xylA-5 mtl-1 thi-1 mcrB1 hsdR2), GC5™ (: F− Φ80lacZ Δ M15 Δ(lacZYA-argF)U169 endA1 recA1 relA1 gyrA96 hsdR17 (r$_k^-$, m$_k^+$) phoA supE44 thi-1 λ-T1R), GC10 (F− mcrA Δ(mrr-hsdRMSmcrBC) Φ80dlacZ Δ M15 Δ lacX74 endA1 recA1 Δ (ara, leu)7697 araD139 galUgalK nupG rpsL λ-T1R), GENEHOGS® (FmcrA Δ(mrr-hsdRMS-mcrBC) φ80lacZΔM15 ΔlacX74 recA1 araD139 Δ(araleu)7697 galU galK rpsL (StrR) endA1 nupG fhuA::IS2 (confers phage T1 resistance)),

HB101,

HMS174,

HMS174(DE3),

HI-CONTROL™ BL21(DE3) (F⁻ ompT gal dcm hsdS$_B$ (r$_B^-$ m$_B^-$) (DE3)/Mini-F lacI$^{q1}$(Gent$^r$)), HI-CONTROL™ 10G (F−mcrA Δ(mrr-hsdRMS-mcrBC) endA1 recA1 Φ80dlacZΔM15 ΔlacX74araD139 Δ(ara, leu)7697 galU galK rpsL nupG λ− tonA/Mini-F lacI$^{q1}$ (Gent$^r$)), HT96™ NOVABLUE (endA1 hsdR17 (r$_{K12}^-$ m$_{K12}^+$) supE44 thi-1 recA1 gyrA96 relA1 lac F'[proA⁺B⁺ lacI$^q$ZΔM15::Tn10] (Tet$^R$)),

IJ1126, IJ1127, INV110, JM83,

JM101 (F' traD36 proA⁺B⁺ lacI$^q$ Δ(lacZ)M15/Δ(lac-proAB) glnV thi),

JM103, JM105, JM106, JM107, JM108,

JM109 (F' traD36 proA⁺B⁺ lacI$^q$ Δ(lacZ)M15/Δ(lac-proAB) glnV44 e14⁻ gyrA96 recA1 relA1 endA1 thi hsdR17), JM109(DE3), JM110, JS5, KS1000 (F lacI$^q$ lac⁺ pro⁺/ara Δ(lac-pro) Δ(tsp)=Δ(prc)::Kan$^R$ eda51::Tn10(Tet$^R$) gyrA(Nal$^R$) rpoB thi-1 argE(am)), LE392, Lemo21(DE3) (fhuA2 [lon] ompT gal (λ DE3) [dcm] ΔhsdS/pLemo(Cam$^R$) λ DE3=λ sBamHIo ΔEcoRI-B int::(lacI::PlacUV5::T7 gene1) i21 Δnin5 pLemo=pACYC184-PrhaBAD-lysY), LIBRARY EFFICIENCY® DH5A™ (F-φ80lacZΔM15 Δ(lacZYA-argF)U169 recA1 endA1 hsdR17(r$_k^-$, m$_k^+$) phoA supE44 thi-1 gyrA96 relA1 λ-), MACH1™T1R (F− Φ80lacZΔM15 ΔlacX74 hsdR(rK−, mK+) ΔrecA1398 endA1 tonA), MAX EFFICIENCY® DH10B™ (F-mcrA Δ(mrr-hsdRMS-mcrBC) φ80lacZΔM15 ΔlacX74 recA1 endA1 araD139 Δ(ara, leu)7697 galU galK λ-rpsL nupG/ pMON14272/pMON7124), MC1061, MC4100, MDS™ 42(MG1655 fhuACDB(del) endA(del)+deletion of 699 additional genes, including all IS elements and cryptic prophages as listed in Posfai et al. (2006) Science (312):1044-1046), MFDpir, NEB Express l$^q$(MiniF lacI$^q$ (Cam$^R$)/fhuA2 [lon] ompT gal sulA11 R(mcr-73::miniTn10--Tet$^S$)2 [dcm] R(zgb-210::Tn10--Tet$^S$)endA1 Δ(mcrC-mrr)114::IS10), NEB Express, dam⁻\dcm⁻, NEB 5-alpha (fhuA2 Δ(argF-lacZ)U169 phoA glnV44 Φ80Δ (lacZ)M15 gyrA96 recA1 relA1 endA1 thi-1 hsdR17), NEB 10-beta (Δ(ara-leu) 7697 araD139 fhuA ΔlacX74 galK16 galE15 e14-φ80dlacZΔM15 recA1 relA1 endA1 nupG rpsL (Str$^R$) rph spoT1 Δ(mrr-hsdRMS-mcrBC)), NiCo21(DE3) (can::CBD fhuA2 [lon] ompT gal (λ DE3) [dcm] arnA::CBD slyD::CBD glmS6Ala ΔhsdS λ DE3=λ sBamHIo ΔEcoRI-B int::(lacI::PlacUV5::T7 gene1) i21 Δnin5), NM522 (F' proA⁺B⁺ lacI$^q$ Δ(lacZ)M15/Δ(lac-proAB) glnV thi-1 Δ(hsdS-mcrB)5), NOVABLUE™ (endA1 hsdR17 (r$_{K12}^-$ m$_{K12}^+$) supE44 thi-1 recA1 gyrA96 relA1 lac F'[proA⁺B⁺ lacI$^q$ZΔM15::Tn10](Tet$^R$)), NovaF- (F⁻endA1 hsdR17 (r$_{K12}^-$ m$_{K12}^+$) supE44 thi-1 recA1 gyrA96 relA1 lac), NOVAXGF' ZAPPERS™ (mcrA Δ(mcrC mrr) endA1 recA1 φ80dlacZΔM15 ΔlacX74araD139 Δ(ara-leu) 7697 galUgalKrpsLnupGλ⁻tonA F'[lacI$^q$Tn10] (Tet$^R$)), OMNIMAX™2T1® (F' {proAB+ lacIq lacZΔM15 Tn10 (TetR) Δ(ccdAB)} mcrA Δ(mrr-hsdRMS-mcrBC) Φ80lacZΔM15 Δ(lacZY A-argF) U169 endA1 recA1 supE44 thi-1 gyrA96 relA1 tonA panD), ONE SHOT® BL21 STAR™ (DE3) (F−ompT hsdSB (rB−, mB−) galdcmme131 (DE3)), ONESHOT® TOP10 (F− mcrA Δ(mrr-hsdRMS-mcrBC) Φ80lacZΔM15 Δ lacX74 recA1 araD139 Δ(araleu) 7697galU galK rpsL (StrR) endA1 nupG), ORIGAMI™ (Δ(ara-leu)7697 ΔlacX74 ΔphoA PvuII phoR araD139 ahpC galE galK rpsLF'[lac⁺ lacI$^q$ pro] (DE3)gor522::Tn10 trxB (Kan$^R$, Str$^R$, Tet$^R$)), ORAGAMI™ 2 (Δ(ara-leu)7697 ΔlacX74 ΔphoA PvuII phoR araD139 ahpC galE galK rpsL F'[lac⁺ lacI$^q$ pro] gor522::Tn10 trxB (Str$^R$, Tet$^R$)), OVEREXPRESS™ C41(DE3) (F-ompT hsdSB (rB−mB−) gal dcm (DE3)), OVEREXPRESS™ C41(DE3)PLYSS (F-ompT hsdSB (rB−mB−) gal dcm (DE3) pLysS (Cm$^R$)), OVEREXPRESS™ C43(DE3) (F-ompT hsdSB (rB−mB−) gal dcm (DE3)), OVEREXPRESS™ C43(DE3)PLYSS (F-ompT hsdSB (rB−mB−) gal dcm (DE3) pLysS (Cm$^R$)), POP2136/pFOS1 (F⁻ glnV44 hsdR17 endA1 thi-1 aroB mal⁻ cI857 lambdaPR), PR1031 (F⁻ thr:Tn10(Tet$^R$) dnaJ259 leu fhuA2 lacZ90 (oc) lacY glnV44 thi), ROSETTA™ (F⁻ompT hsdS$_B$(r$_B^-$ m$_B^-$) gal dcm pRARE (Cam$^R$)), ROSETTA™(DE3)PLYSS (F⁻ompT hsdS$_B$(r$_B^-$ m$_B^-$) gal dcm (DE3) pLysSRARE2 (Cam$^R$)), ROSETTA-GAMI™ (Δ(ara-leu)7697 ΔlacX74 ΔphoA PvuII phoR araD139 ahpC galE galK rpsL F'[lac⁺ lacI$^q$ pro] gor522::Tn10 trxB pRARE2 (Cam$^R$, Str$^R$, Tet$^R$)), ROSETTA-GAMI™(DE3)PLYSS (Δ(ara-leu)7697 ΔlacX74 ΔphoA PvuII phoR araD139 ahpC galE galK rpsL (DE3) F'[lac⁺lacI$^q$ pro]gor522::Tn10 trxB pLysS-RARE2 (Cam$^R$, Str$^R$, Tet$^R$)), RR1, RV308, SCARABXPRESS® T7LAC (MDS™42 multiple-deletion strain (1) with a chromosomal copy of the T7 RNA Polymerase gene), SS320 (F'[proAB+lacIqlacZΔM15 Tn10 (tet$^r$)]hsdR mcrB araD139 Δ(araABC-leu)7679 ΔlacX74 galUgalK rpsL thi), SHUFFLE® (F' lac pro lacI$^q$/Δ(ara-leu)7697 araD13 fhuA2 Δ(lac)X74 Δ(phoA)PvuII phoR ahpC* galE (or U) galK Δκatt::pNEB3-r1-cDsbC (SpecR, lacI<sup>q</sup>) ΔtrxB rpsL150(StrR) Δgor Δ(malF)3), SHUFFLE® T7 (F' lac, pro, lacI<sup>q</sup>/Δ(ara-leu)7697 araD139 fhuA2 lacZ::T7 gene1 Δ(phoA)PvuII phoR ahpC* galE (or U) galK λatt:pNEB3-r1-cDsbC (Spec<sup>R</sup>, lacI<sup>q</sup>) ΔtrxB rpsL150(Str<sup>R</sup>) Δgor Δ(malF)3), SHUFFLE® T7 EXPRESS (huA2 lacZ::T7 gene1 [lon] ompT ahpC gal λatt::pNEB3-r1-cDsbC (Spec<sup>R</sup>, lacI<sup>q</sup>) ΔtrxB sulA11 R(mcr-73::miniTn10--Tet<sup>S</sup>)2 [dcm] R(zgb-210::Tn10--Tet<sup>S</sup>) endA1 Δgor Δ(mcrC-mrr) 114::IS10), SOLR (e14-(McrA-) Δ(mcrCB-hsdSMR-mrr)171 sbcC recB recJ uvrC umuC::Tn5 (Kan<sup>r</sup>) lac gyrA96 relA1 thi-1 endA1 λ<sup>R</sup> [F' proAB lacI<sup>q</sup>Z ΔM15]<sup>C</sup> Su-), SCS110, STBL2™ (F–endA1 glnV44 thi-1 recA1 gyrA96 relA1 Δ(lac-proAB) mcrA Δ(mcrBC-hsdRMS-mrr)), STBL3™ (F–glnV44 recA13 mcrB mrr hsdS20(rB–, mB–) ara-14 galK2 lacY1 proA2 rpsL20 xyl-5 leu mtl-1), STBL4™ (endA1 glnV44 thi-1 recA1 gyrA96 relA1 Δ(lac-proAB)mcrA Δ(mcrBC-hsdRMS-mrr) λ<sup>-</sup> gal F'[proAB<sup>+</sup> lacI<sup>q</sup> lacZΔM15 Tn10]), STELLAR™ (F–, endA1, supE44, thi-1, recA1, relA1, gyrA96, phoA, Φ80d lacZΔ M15, Δ(lacZYA-argF) U169, Δ(mrr-hsdRMS-mcrBC), ΔmcrA, λ–).

SURE (endA1 glnV44 thi-1 gyrA96 relA1 lac recB recJ sbcC umuC::Tn5 uvrC e14-Δ(mcrCB-hsdSMR-mrr) 171 F'[proAB<sup>+</sup> lacI<sup>q</sup> lacZΔM15 Tn10]), SURE2 (endA1 glnV44 thi-1 gyrA96 relA1 lac recB recJ sbcC umuC::Tn5 uvrC e14-Δ(mcrCB-hsdSMR-mrr) 171 F'[proAB<sup>+</sup> lacI<sup>q</sup> lacZΔM15 Tn10 Amy Cm<sup>R</sup>]), T7 Express Crystal (fhuA2 lacZ::T7 gene1 [lon] ompT gal sulA11 R(mcr-73::miniTn10--Tet<sup>S</sup>)2 [dcm] R(zgb-210::Tn10--Tet<sup>S</sup>)endA1 metB1 Δ(mcrC-mrr)114::IS10), T7 Express lysY\I<sup>q</sup> (MiniF lysY lacI<sup>q</sup>(Cam<sup>R</sup>)/fhuA2 lacZ::T7 gene1 [lon] ompT gal sulA11 R(mcr-73::miniTn10--Tet<sup>S</sup>)2 [dcm] R(zgb-210::Tn10--Tet<sup>S</sup>) endA1 Δ(mcrC-mrr) 114::IS10), T7 Express lysY (MiniF lysY (Cam<sup>R</sup>)/fhuA2 lacZ::T7 gene1 [lon] ompT gal sulA11 R(mcr-73::miniTn10--Tet<sup>S</sup>)2 [dcm] R(zgb-210::Tn10--Tet<sup>S</sup>)endA1 Δ(mcrC-mrr)114::IS10), T7 Express I<sup>q</sup> (MiniF lacI<sup>q</sup>(Cam<sup>R</sup>)/fhuA2 lacZ::T7 gene1 [lon] ompT gal sulA11 R(mcr-73::miniTn10--Tet<sup>S</sup>)2 [dcm] R(zgb-210::Tn10--Tet<sup>S</sup>)endA1 Δ(mcrC-mrr) 114::IS10), T7 Express (fhuA2 lacZ::T7 gene1 [lon] ompT gal sulA11 R(mcr-73::miniTn10--Tet<sup>S</sup>)2 [dcm] R(zgb-210::Tn10--Tet<sup>S</sup>) endA1 Δ(mcrC-mrr)114::IS10), TB1 (F<sup>-</sup> ara Δ(lac-proAB) [Φ80dlac Δ(lacZ)M15] rpsL (Str<sup>R</sup>) thi hsdR), TG1 (F' [traD36 proAB<sup>+</sup> lacI<sup>q</sup> lacZΔM15]supE thi-1 Δ(lac-proAB) A(mcrB-hsdSM)5, ($r_K^- m_K^-$)), THUNDERBOLT™ GC10 (F– mcrA Δ (mrr-hsdRMSmcrBC) Φ80dlacZ Δ M15 DlacX74 endA1 recA1 Δ (ara, leu)7697 araD139 galU galK nupG rpsL 1 λ-T1R), UT5600 (F<sup>-</sup> ara-14 leuB6 secA6 lacY1 proC14 tsx-67 A(ompT-fepC)266 entA403 trpE38 rfbD1 rpsL109 xyl-5 mtl-1 thi-1), VEGGIE™ BL21(DE3) (F<sup>-</sup>ompT hsdS<sub>B</sub>($r_B^- m_B^-$) gal dcm(DE3)), W3110 (λ857S7),

WM3064,

XL1-Blue (endA1 gyrA96(nal<sup>R</sup>) thi-1 recA1 relA1 lac glnV44 F'[::Tn10 proAB<sup>+</sup> lacI<sup>q</sup>Δ(lacZ)laM15] hsdR17 ($r_K^- m_K^+$)), XL1-Blue MRF'(Δ(mcrA)183 Δ(mcrCB-hsdSMR-mrr) 173 endA1 supE44 thi-1 recA1 gyrA96 relA1 lac [F' proAB lacI<sup>q</sup>ZΔM15 Tn10 (Tet<sup>r</sup>)]), XL2-Blue (endA1 gyrA96(nal<sup>R</sup>) thi-1 recA1 relA1 lac glnV44 F'[::Tn10 proAB<sup>+</sup>lacI<sup>q</sup>Δ(lacZ)M15 Amy Cm<sup>R</sup>] hsdR17($r_K^- m_K^+$)), XL2-Blue MRF'(endA1 gyrA96(nal<sup>R</sup>) thi-1 recA1 relA1 lac glnV44 e14-Δ(mcrCB-hsdSMR-mrr)171 recB recJ sbcC umuC::Tn5 uvrC F'[::Tn10 proAB<sup>+</sup> lacI<sup>q</sup>Δ(lacZ) M15 Amy Cm<sup>R</sup>]), XL1-Red (F– endA1 gyrA96(nal<sup>R</sup>) thi-1 relA1 lac glnV44 hsdR17($r_K^- m_K^+$) mutS mutT mutD5 Tn10), XL10-Gold (endA1 glnV44 recA1 thi-1 gyrA96 relA1 lac Hte A(mcrA)183 Δ(mcrCB-hsdSMR-mrr)173 tet<sup>R</sup> F'[proAB lacI<sup>q</sup>ZΔM15 Tn10(Tet<sup>R</sup> Amy Cm<sup>R</sup>)]), and XL10-Gold KanR (endA1 glnV44 recA1 thi-1 gyrA96 relA1 lac Hte A(mcrA)183 Δ(mcrCB-hsdSMR-mrr) 173 tet<sup>R</sup> F'[proAB lacI<sup>q</sup>ZΔM15 Tn10(Tet<sup>R</sup> Amy Tn5 (Kan<sup>R</sup>)]).

The following examples are provided to illustrate various aspects of the present invention, and should not be construed as limiting the invention only to these particularly disclosed embodiments. The materials and methods employed in the examples below are for illustrative purposes, and are not intended to limit the practice of the present invention thereto. Any materials and methods similar or equivalent to those described herein can be used in the practice or testing of the present invention.

EXAMPLE 1

Identification of Host Cell Proteins Associated with a Specific Product, Histidine-Tagged Green Fluorescent Protein, as a Comparative Example This comparative example demonstrates the identification of proteins of the 120 mM imidazole fraction (Ni(II) IMAC) and subsequent gene deletions. It demonstrates how to eliminate host cell contaminants for a specific target recombinant product, Green Fluorescent Protein (GFPuv), extended by a histidine-rich affinity tag (His<sub>6</sub>-GFP). His<sub>6</sub>-GFP elutes similarly to other histidine-tagged proteins found in the literature. While this example discloses three gene deletions that, in principle, would enhance the purity of the desired product, the knockouts of cyoA, adhP, and yfbG and their subsequent lack of expression does not favorably impact column capacity. These three proteins are insignificant in the metalloproteome of *E. coli*. Thus, no changes to the separatome are disclosed that lead to an overall increase in separation efficiency. The text of this example is an annotated version of the inventors' work described in Liu et al. (2009) *J. Chromatog. A* 1216:2433-2438.

Strains, Plasmids, and Growth Conditions

*Escherichia coli* BL21 DE3 expressing GFPuv tagged with HHHHHH (His<sub>6</sub>) (SEQ ID NO:1) were constructed using basic molecular biology techniques. PCR primers F (5'-GCC<u>AAGCTT</u>GTGGCATCATCATCCGCATATGAG TAAAG<u>GAGAAG</u>AACTTTTC-3') (SEQ ID NO:2) and R (5'-TTG<u>GAATTC</u>ATTATTTGTAG AGCT-3') (SEQ ID NO:3) containing Hind III and EcoRI sites (underlined correspondingly), were used to amplify and extend GFPuv. These enzymes were used to digest the PCR fragment and the parent plasmid. T4 DNA ligase was then used to construct a new vector that was built from the PCR-extended gene and the major part of the pGFPuv plasmid. Transformants were selected in LB agar containing 50 μg/ml ampicillin. *E. coli* cells were grown in Luria-Bertani (LB) overnight and inoculated in a 2-liter flask containing 500 ml M9 supplemented with 10 g/L glucose such that the initial A<sub>660</sub> was 0.1. To express His$_6$-GFPuv, 4% inoculations of overnight cultures were made in 500 mL LB and induced with 1 mM of IPTG after 1-2 hours. Fermentations were carried out at 37° C. and the agitation speed of the shaker was set at 200 rpm. Cell pellets were collected by centrifugation at 5000 g and frozen at −80° C. before cell lysis.

Sample Preparation and Chromatography

Cell pellets were suspended in 20 ml 1× native purification buffer (50 mM NaH$_2$PO$_4$, pH 8.0; 500 mM NaCl) combined with 100 µl Triton X-100, 80 µl 100 mM MgCl$_2$, 20 µl phenylmethylsulphonyl fluoride (PMSF) and 100 µl 100 mg/mL lysozyme. The mixture was sonicated on ice at 4 W for 30 min using a Vibra cell ultrasonifier (Fisher Scientific, Pittsburgh, Pa., USA), and centrifuged at 5000 rpm for 20 min. The supernatants were collected and passed through a 0.45 µm filter before column loading.

For experiments identifying natural contaminants or to follow the adsorption and elution of His$_6$-GFP, the cleared lysate was applied to 4 ml ProBond nickel-chelating resin in an open column followed by equilibration using 1× native purification buffer (5× native purification buffer, as supplied with the resin, is comprised of 250 mM NaH2PO4, pH 8.0. 2.5 M NaCl). Step elutions were carried out with native purification buffer with the following imidazole concentrations: 60 mM, 80 mM, 100 mM, 120 mM, and 200 mM. This was followed by a 500 mM EDTA elution. The elution volumes for each step were 24 ml, or 6 column volumes (CVs), and applied at an approximate flow rate of 0.5 ml/min. Fractions were collected and measured for protein concentration with a BCA Protein Assay Kit (Pierce, Rockford, Ill., USA) and/or assayed for GFPuv in triplicate with a Tecan Infinite M200 96-well plate reader with excitation/emission spectra set to 395/509 nm.

SDS-PAGE and Mass Spectrometry

Sodium dodecyl sulfate polyacrylamide gel electrophoresis (SDS-PAGE) was performed for 6 hours at 100 V. Gels were stained with Coomassie Blue. The Genomics and Proteomics Core Laboratories at the University of Pittsburgh performed the protein identification. To account for the experimental accuracy of the measurement, three spots were excised from each band and each digested with trypsin. Peptides were separated by liquid chromatography (LC), then identified by tandem mass spectrometry (MS/MS) fragmented by collision-induced dissociation. MASCOT v2.1 (Matrix Science, Boston Mass. USA) was used to match LC/MS data with *E. coli* proteins. For positive identification, spectral data from each of the three spots matched.

Functional Prediction of Identified Proteins in 120 mM Elution Fraction

Functional classification of all identified proteins was based on the Profiling of *Escherichia coli* chromosome (PEC) database (Hashimoto et al. (2005) *Molecular Microbiology* 55: 137-149).

Construction of Knockout Mutants

All the knockout mutants of this Example were generated with the same deletion system according to the manual accompanying the Quick and Easy *E. coli* Gene Deletion Kit (Gene Bridges, Heidelberg, Germany). This kit uses plasmid pRedET to facilitate homologous recombination events. During the progression of the work, a triple mutant of BL21 (ΔcyoAΔyfbGΔadhP) was constructed through a series operation consisting of recombination, selection with kanamycin, confirmation, and removal of the selection marker using flipase recognition site (FRT flanked kanamycin gene).

Southern Blot Analysis

DNA probes used for Southern hybridization were prepared from PCR-amplified fragments. Probes were labeled according to the manual of Amersham Gene Images Random Prime Labeling Kit (GE Healthcare). Genomic DNA was isolated from knockout mutants using standard protocols. DNA samples were digested with Bam HI, separated by electrophoresis on 1% agarose gels, transferred to Amersham Hybond-N+ membranes (GE Healthcare), and then baked at 80° C. for 2 hours. The probes were hybridized to these blots and detected according to the protocol of the Gene Images ECL Detection Kit (GE Healthcare).

SDS-PAGE Evaluation of CyoA, YfbG and AdhP Knockout in Mutant Strains

Cell preparations of BL21, mutants, and chromatography fractions were evaluated by SDS-PAGE. Approximately 15 µg sample/well were loaded into a 12% acrylamide gel.

Identification of Knockout Candidates and Confirmation of their Deletion

Figure 3:
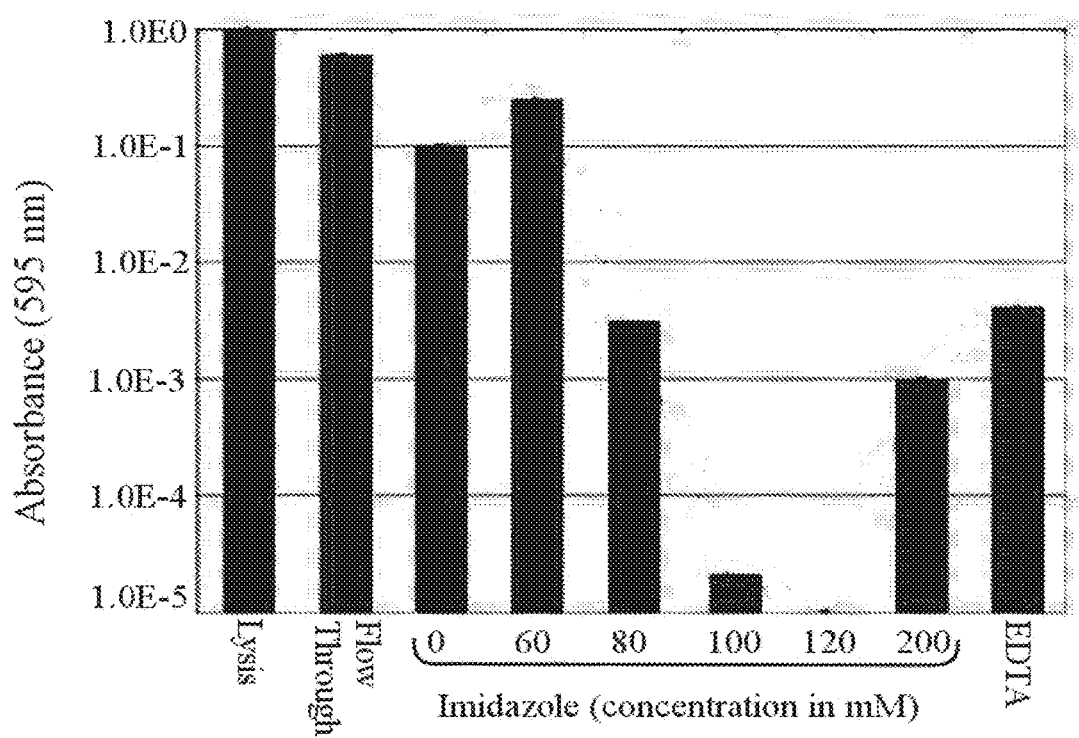
FIG. 3 shows the distribution of proteins contained within various IMAC fractions that elute from a Ni(II) column. In particular, note the low concentration of host cell proteins within the 120 mM fraction.

A total extract of *E. coli* protein was loaded to the ProBond nickel-chelating column using 1× native purification buffer (5× native purification buffer, as supplied with the resin, is comprised of 250 mM NaH2PO4, pH 8.0. 2.5 M NaCl). Step elutions were carried out with native purification buffer with the following imidazole concentrations: 60 mM, 80 mM, 100 mM, 120 mM, and 200 mM. FIG. 3 shows the protein concentrations in each fraction normalized to the total protein used for column loading. The bar graph indicates order of magnitude changes in the total protein encountered with each imidazole challenge. Note that the elution fraction containing the 120 mM imidazole fraction contained the least amount of protein. Coincidentally, this fraction that contains low host cell protein is also the fraction where His$_6$-GFPuv elutes.

Figure 4A:
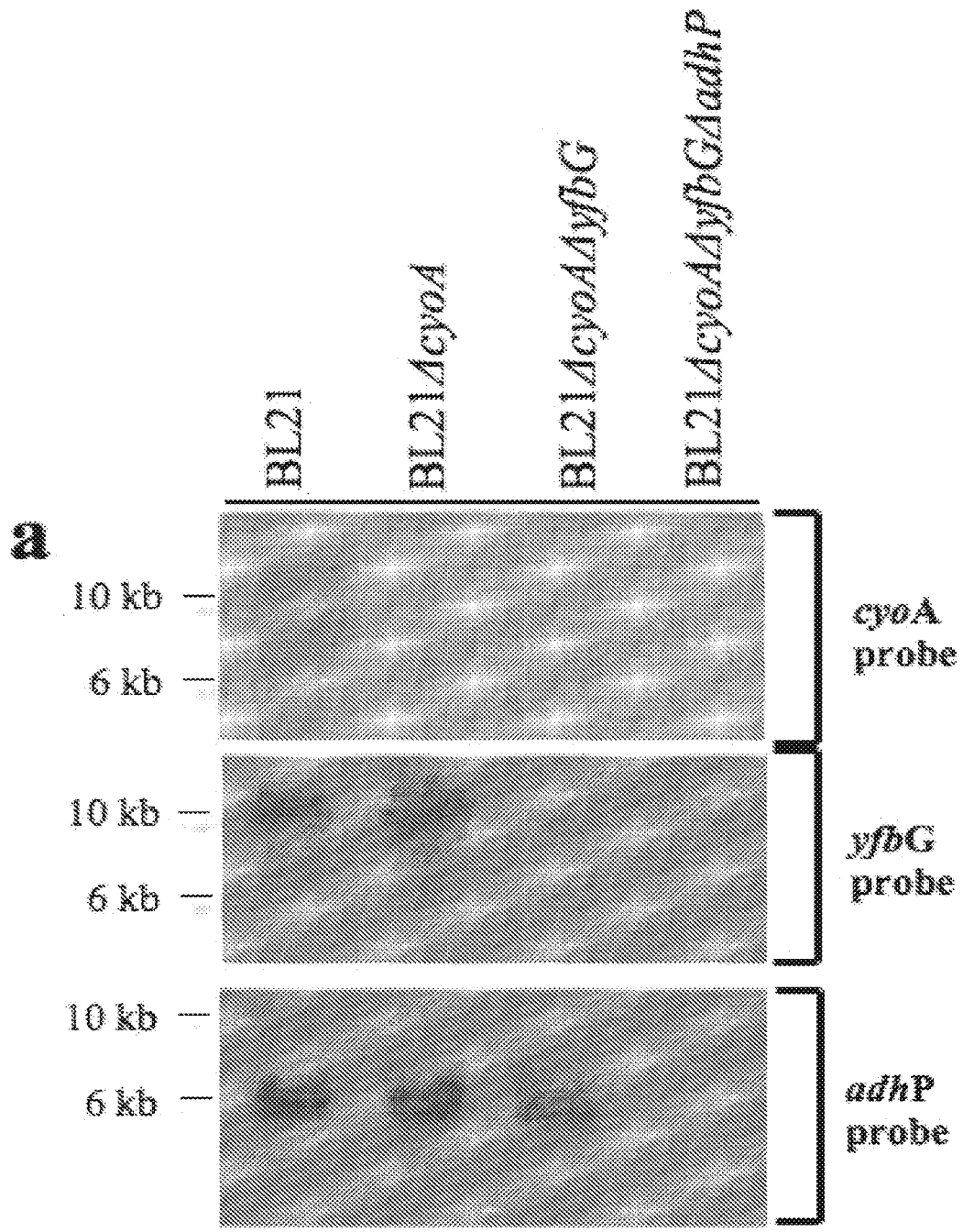
FIG. 4A shows a Western blot and FIG. 4B shows a protein gel that indicate lack of expression of gene products of yfbG, adhP, and cyoA. Lack of expression is indicated by absence of spot or band.
Figure 4B:
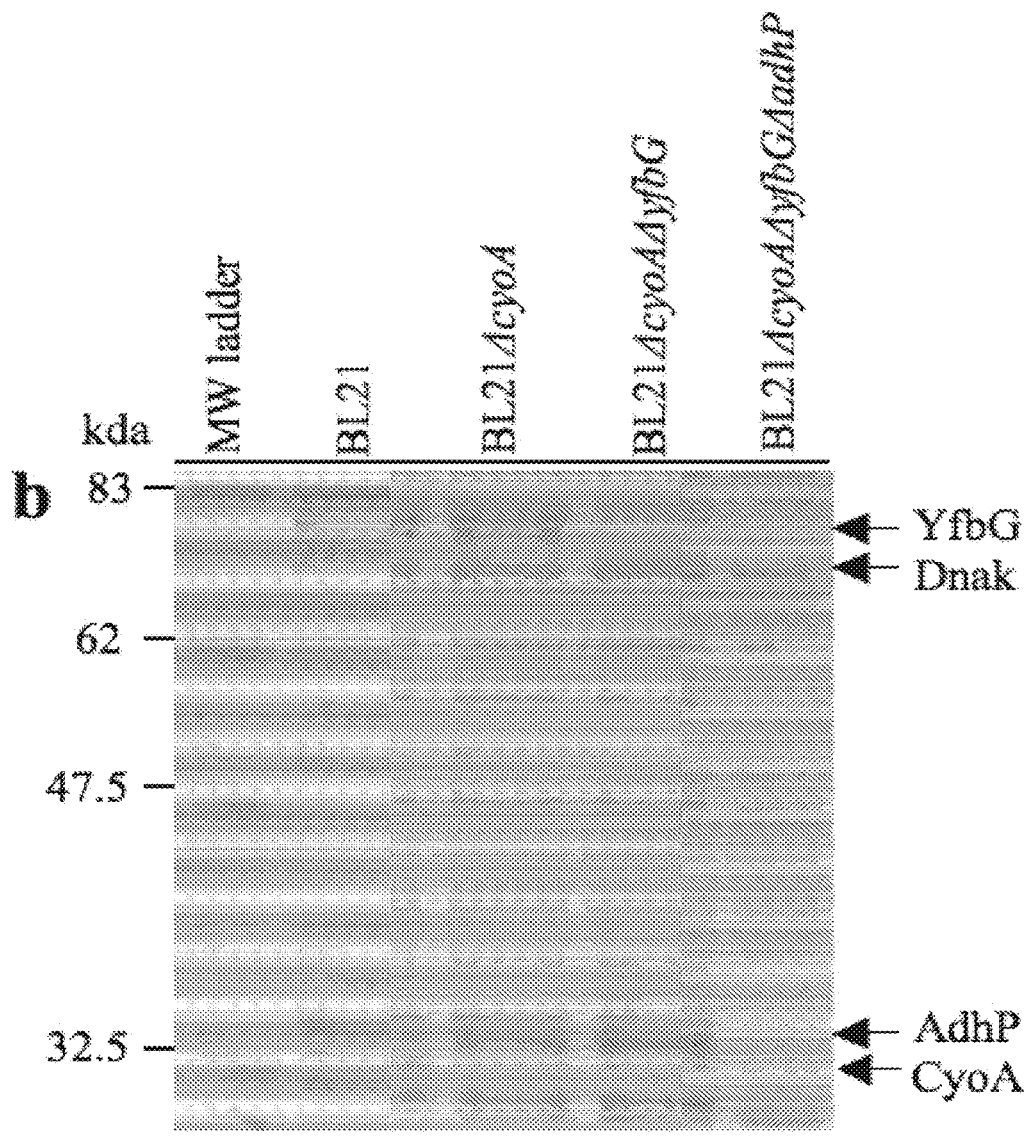

SDS-PAGE and LC-MS/MS were used to identify the cellular proteins present in the concentrated sample of pooled 120 mM imidazole elution fractions. A total of 18 proteins were identified (Table 2), with cyoA, yfbG, and adhP selected for deletion due to lack of essentiality. Southern blot analysis and gel electrophoresis indicated lack of expression of the three gene products cyoA, yfbG, and adhP. FIG. 4 shows this confirmation due to lack of spots associated with positive hybridization and bands of the molecular weights of these products, respectively.

TABLE 2

| Proteins eluted at 120 mM from a Ni(II)-NTA column |
|---|
| dnaK |
| yfbG |
| adhP |
| cyoA |
| rplB |
| slyD |
| nagD |
| ahpC |
| rpsG |
| rplO |
| rpsE |
| rplM |
| Fur |
| Hypothetical protein ECs2542 |
| rplJ |
| rpsL |
| Hns |
| rplL |

These results demonstrate that it is possible to apply a limited set of data and to produce a knockout strain that might be capable of enhancing the purity of a recombinant peptide, polypeptide, or protein. It is used as a comparative example to illustrate the lack of a rigorous methodology to identify specific changes to the host cell that lead to an altered separatome capable of broadly improving separation efficiency, and column capacity in particular, regardless of desired recombinant product. By focusing on the contaminants of a single specific his-tagged protein in a particular column fraction, Liu et al. (2009) *J. Chromatog. A* 1216: 2433-2438 fails to even consider the principle of prioritizing host cell contaminant proteins that, if deleted, modified, or inhibited, would significantly improve column capacity and/or selectivity ("chromatographic separation efficiency") for a wide variety of different recombinant peptides, polypeptides, and proteins as disclosed and claimed herein.

EXAMPLE 2

Construction of an Ion Exchange Separatome of *E. coli* and its Use to Design and Build Novel Host Strains for a Common Chromatography Resin This example describes the process by which a separatome is constructed for a chromatography resin and subsequently used to guide modifications to *E. coli* to increase chromatographic efficiency. It begins by describing how data are acquired by fractionating an extract derived from fed batch growth over a DEAE ion exchange bed, and continues by constructing the separatome—a data structure that includes information on the genes responsible for identified proteins coupled to a quantitative scoring to rank order molecular biology efforts that lead to a reduced separatome. Finally, construction of example strains is described, concluding with information regarding high priority strain modifications necessary for significant gains in separation efficiency through their deletion, modification, or inhibition.

Section I.
Cloning Strains and Vectors

*E. coli* strain MG1655 (K-12 derivative) was selected as the base strain for cell line modification because of its widespread use and lack of commercial license. Its genotype is F$^-$ lambda$^-$ rph$^{-1}$, meaning that it lacks an F pilus, the phage lambda, and has a15 codon frame-shift as result of the rph 1 bp deletion (Yale University. *E. coli* Genetic Stock Center Database. 2013). This frame-shift interrupts the pyrE gene and reduces pyrimidine levels (Jensen et al. (1993) *Journal of Bacteriology* 175(11):3401-7).

Plasmid pKD46 was used as part of the λ-red recombination system. This plasmid is ampicillin resistant and replication is temperature sensitive. For plasmid maintenance, growth is at 30° C. and the plasmid can be removed by growth at 37° C. without antibiotic pressure. The plasmid encodes for lambda Red genes exo, bet, and gam, and includes an arabinose-inducible promoter for expression (Datsenko et al. (2000) *PNAS* 97(12):6640-5). The plasmid was provided in conjunction with MG1655 from the Yale *E. Coli* Genetic Stock Center (New Haven, Conn.).

Expression Strains and Vectors

*E. coli* strain BL21 (DE3) was used for initial cell culture and cell lysate preparation. Its genotype is F– ompT hsdSB (rB–, mB–) gal dcm (DE3). The strain and genotype was provided by Novagen (EMD-Millipore/Merck). The cell line was transformed with a recombinant pGEX plasmid provided by Dr. Joshua Sakon (Department of Chemistry, University of Arkansas). This plasmid, pCHC305, contains the genetic information for the recombinant fusion protein, glutathione-S-transferase—parathyroid hormone—collagen binding domain (GST-PTH-CBD, 383 amino acids).

Storage Strains and Vectors

For storage of DNA constructs, *E. coli* strain DH5α was selected. Its genotype is F–, Δ(argF-lac)169 φ80dlacZ58 (M15) ΔphoA glnV44(AS)8 λ– deoR481 rfbC gyrA96 (NalR)1 recA1 endA1 thiE1 hsdR17. DH5 is a non-mutagenized derivative of DH1, which transforms more efficiently due to a deoR mutation. The recA mutation eliminates homologous recombination and minimizes undesired modification to stored plasmids. pUC19 was used as a DNA storage vector. It is a high copy number plasmid that carriers ampicillin resistance. This plasmid was provided in conjunction with DH5α from the Yale *E. Coli* Genetic Stock Center (New Haven, Conn.).

Liquid Growth Media

M9 medium was used where a minimal defined medium was required. M9 Medium was made in 3 separate stock solutions: glucose solution (500 g/L), trace elements (2.8 g of FeSo4-7H2O, 2 g of MnCl2-4H2O, 2.8 g off CoCl2-7H2O, 1.5 g of CaCl2-2H2O, 0.2 g CuCl2-2H2O, 0.3 g of ZnSO4-7H2O), and 5× M9 (75 g of K2HPO4, 37.5 g of KH2PO4, 10 g of citric acid, 12.5 g of (NH4)2SO4, 10 g of MgSO4-7H2O). Each of these components must be autoclaved individually to minimize salt precipitation. To prepare 1 L of M9, 20 ml of the glucose solution is mixed with 1 ml trace element solution, 200 ml of 5× M9, and enough water to bring the final volume up to 1 L (approximately 780 ml).

Where rich medium was required, Luria-Burtani (LB) Medium was used. LB powder was purchased from Difco and was prepared per the manufacturer's instructions: 20 g LB powder per 1 L of milliQ water.

Solid Growth Media

Solid M9 medium was prepared as previously described for liquid M9 with the addition of agar to the water and concentrated M9 solution prior to autoclaving. To prepare 500 ml of M9 agar, 7.5 g agar, 100 ml of 5× M9 solution, and 300 ml of water are mixed and autoclaved. Added to this is 10 ml sterile glucose solution (500 g/L), 500 μl trace elements, and enough sterile water to bring the final volume up to 500 ml. The other solid medium used was LB agar, which was prepared the same as the LB liquid medium described earlier plus the addition of 7.5 g agar per liter.

Fed-Batch Cultivation

Fed-batch cultivation was used to prepare the cell lysate for use in downstream protein purification and identification of natively expressed proteins. The cell line used was BL21(DE3):pCHC305. To begin fermentation, a single colony was isolated from a LB ampicillin agar plate and transferred to a 5 ml culture tube containing liquid LB plus 150 μg/ml ampicillin. This culture tube was allowed to incubate overnight at 37° C. After overnight growth, the 5 ml culture tube is supplemented with 100 ml of M9 with ampicillin and allowed to grow at 37° C. for six to eight hours. This 100 ml culture is then centrifuged at 4750 rpm for 25 minutes (Beckman Coulter Allegra) and re-suspended in 50 ml of fresh M9 medium with 150 μg/ml ampicillin. This culture was used as the inoculant for the fed-batch growth. The 3-liter Applikon bioreactor (Foster City, Calif.) contained 1 liter of M9 plus 150 μg/ml ampicillin and 1 ml silicone anti-foam.

The Applikon unit was equipped with BioXpert Advisory software from Applikon, an Applisense pH probe, and a dissolved oxygen probe. To maintain proper dissolved oxygen, the reactor was supplemented with pure oxygen provided by a compressed gas cylinder with a controllable flow rate. To insure effective gas dispersal, the culture was initially stirred at 750 rpm and was later increased to 1000 rpm based on cell density. Adjustments in oxygen delivery were made as necessary during the process to ensure that the dissolved oxygen concentration did not drop below 35%. The pH was maintained at approximately 6.8 (with a range of 6.75 to 7) during the cultivation by adding 7M $NH_4OH$ as needed. Temperature was maintained at 37° C. using a heating jacket and cooling loop. Optical densities were monitored using a Bugeye optical density probe (BugLab, Foster City, Calif.) and a DU800 Beckman Coulter spectrophotometer (Brea, Calif.). A linear correlation for the Bugeye response to the actual optical density (OD) as measured by the spectrophotometer was determined for each individual experiment.

The fed-batch fermentation process has two phases, a batch phase and a feeding phase. In the batch phase, the culture uses only the carbon sources provided in the media at the start of the cultivation and no nutrients are fed to the reactor. This phase lasted approximately 7-8 hours, depending on the lag phase of the culture and how rapidly the culture grew on the initial carbon substrate. The shift from batch phase to feeding phase can be determined by two indicators, a rise in pH and a sharp decline in oxygen concentration, which indicate that the initial carbon substrate has been depleted. In the fed-batch experiments, these two events occur simultaneously and are displayed by the Applikon software. The feeding profile used for fermentation experiments is based on that of a collaborator (McKinzie Fruchtl) and was originally proposed by Korz et al. (1995) *Journal of Biotechnology* 39(1):59-65 and Lee et al. (1996) *Trends in Biotechnology* 14(3):98-105. A feeding profile was programmed into the Applikon software that mimics the exponential feed based on substrate concentrations.

An exponential fed-batch fermentation method commonly used to pre-determine the amount of glucose that should be fed into the reactor to achieve a certain growth rate was proposed by Korz et al. and Lee et al., supra:

$$M_S(t) = F(t)S_F(t) = \left(\frac{\mu}{Y_{X/S}} + m\right)X(t)V(t) = \left(\frac{\mu}{Y_{X/S}} + m\right)X(t_F)V(t_F)\exp^{\mu(t-t_F)} \quad \text{Equation 4}$$

where $M_s$ is the mass flow rate (g/h) of the substrate, F is the feeding rate (l/h), $S_F$ is the concentration of the substrate in the feed (g/l), μ is the specific growth rate (1/h), $Y_{X/S}$ represents the biomass on substrate yield coefficient (g/g), m is the maintenance coefficient (g/g h), and X and V represent the biomass concentration (g/l) and cultivation volume (l), respectively. The yield coefficient for *E. coli* on glucose is generally taken to be 0.5 g/g (Korz et al., supra; Shiloach et al. (2005) *Biotechnology Advances* 23(5):345-57). The maintenance coefficient is often 0.025 g/g h (Korz D J et al., supra). This equation has been widely adapted for fed-batch fermentation processes, as exponential feeding allows cells to grow at a constant rate (Kim et al. (2004) 26(3):147-50).

During fed-batch fermentation, the cells were left un-induced to prevent/minimize the addition of the recombinant protein to the native protein pool. This strategy provided the stress associated with plasmid maintenance common to all bacterial fermentations where the gene for the target peptide, polypeptide, or protein is housed on a plasmid. Furthermore, this strategy permits the derivation of a separatome that is not biased by large amounts of target peptide, polypeptide, or protein, attesting to the universal nature of the approach. The fermentation was allowed to grow for a total of 24 hours from inoculation to harvest. At the end of the fermentation process, cells were harvested from the reactor by pumping the reactor contents into centrifuge bottles. The reactor contents were then centrifuged at 12,000×g for 30 minutes at 5° C. (Beckman Coulter Avanti, JLA-10.500 fixed angle rotor) to separate the cell pellet from the media. The pellet was separated into four 50 ml conical bottom tubes for storage at −20° C.

Lysate Preparation

One of the 50 ml pellets (58.9 g) was re-suspended in 150 ml of 25 mM Tris buffer, pH 7. To enable cell lysis, 2 mg/ml lysozyme were added to the mixture. In addition, 1 mM phenylmethylsulphonyl fluoride (PMSF), 20 μg/ml aprotinin, and 1 mM ethylenediamine-tetraacetic acid (EDTA) was added to minimize protein degradation. The mixture was then incubated on ice with stirring for 30 minutes to lyse the cells. The mixture was then centrifuged at 50,000×g (Beckman Coulter Avanti, JA-25.50 fixed-angle rotor) for 30 minutes at 5° C. to separate the proteins from the cell debris.

The proteins in the supernatant were carefully pipetted out of the centrifuge tubes, to minimize contaminants from the insoluble fraction, and were clarified by syringe filtration through 0.45 μm cellulose acetate. Lastly, the total protein concentration of the cell lysate was determined by using a Bio-Rad DC Protein Assay which is a detergent compatible colorimetric assay that is read by spectrophotometer at 750 nm (Beckman Coulter DU 800 HP). Bovine serum albumin standards were used to determine the baseline correlation between protein concentration and absorbance at 750 nm.

Fast Protein Liquid Chromatography

Fast protein liquid chromatography (FPLC) was used to separate the natively expressed proteins into groups based on the salt concentration at which they elute, which correlates to their surface charge. The chromatography was performed using an Amersham ÄkTA FPLC. The system consists of dual syringe pumps (P-920), gradient mixer, a monitor (UPC-900) for UV (280 nm), pH and conductivity, a fraction collector (Frac-900) and UNICORN® V3.21 data collection and archive software.

Resin

For the initial separatome database development, diethylaminoethyl cellulose (DEAE) was selected as the ion exchange (IEX) resin due to its prevalence of use in industrial manufacturing. Specifically, the column used was a 1 ml HiTrap DEAE FF from GE Healthcare. DEAE is a weak anion exchanger, meaning that it is a positively charged matrix with a narrow working pH of 2-9 (GE Healthcare. Instructions 71-5017-51 AG HiTrap ion exchange columns 1-24.).

Buffer Composition 25 mM Tris buffer, pH 7, was selected for all of the FPLC purification steps. The loading buffer contained 10 mM NaCl to minimize non-specific binding (Buffer A). The elution buffer contained 1M NaCl, which is sufficient to desorb bound proteins (Buffer B).

Column Loading Conditions

Prior to loading the column, the system was washed with buffer A until equilibrium was achieved (roughly 10 ml). At this point, all system monitors were base-lined. The column was loaded at 10% breakthrough as per industry standard. The amount of total lysate to be applied to the column to achieve this breakthrough was determined as follows. According to GE Healthcare, the dynamic binding capacity (DBC) of HiTrap DEAE FF is 110 mg HSA (human serum albumin)/ml solvent (resin). This number gives the amount of protein that can be bound per milliliter of resin. The next step was to determine what percentage of the native proteins bound to the DEAE resin at pH 7. To do this, 5 ml of lysate was loaded on the column and washed with 10 ml of buffer A. The flow-through was collected in a single fraction. The column was then washed with the buffer B and the resulting flow-through was collected. Both fractions were then analyzed for their total protein concentration using the previously mentioned Bio-Rad assay. The amount of lysate (ml) to load onto the column was determined by the following equation:

$$lysate\ (ml) = \frac{DBC*(1 + \%_{BT})*V_C}{\%_{bound}*C_l} \quad \text{Equation 5}$$

where DBC is the dynamic binding capacity of the resin (mg/ml), $\%_{BT}$ is the desired percent breakthrough, $V_c$ is the volume of the column (ml), $\%_{bound}$ is the percent of the total lysate that binds to the resin, and $C_l$ is the protein concentration of the lysate (mg/ml).

The column was loaded at 1 ml/min and then washed with 10 column volumes (CV) of buffer A to remove any unbound proteins. The unbound fraction was collected for later analysis.

Column Elution Conditions

To identify where the bulk of the bound proteins eluted, the proteins were desorbed through roughly 100 mM salt steps from 10 mM to 1M. This process allows for the identification of the priority salt fractions that need to be spaced out into smaller steps for later analysis.

TABLE 3

10% Elution Windows

| Step # | % B | NaCl (mM) | Step Length (CV) |
|---|---|---|---|
| wash | 0% | 10 | 10 |
| 1 | 10% | 109 | 5 |
| 2 | 20% | 208 | 5 |
| 3 | 30% | 307 | 5 |
| 4 | 40% | 406 | 5 |
| 5 | 50% | 505 | 5 |
| 6 | 60% | 604 | 5 |
| 7 | 70% | 703 | 5 |
| 8 | 80% | 802 | 5 |
| 9 | 90% | 901 | 5 |
| 10 | 100% | 1000 | 5 |
| clean | 100% | 1000 | 5 |

The flow rate was maintained at 1 ml/min and the pressure limit was set to 0.5 MPa for the duration of the experiment. During elution, all fractions were collected and immediately stored at 2° C. to reduce protein degradation. After all of the proteins have been desorbed in the 1000 mM step, the fraction collector is stopped and the column is cleaned with buffer B to ensure all proteins have been desorbed and washed out of the column. The column is then washed with sufficient buffer A to re-equilibrate the column.

For finer focusing on the primary elution windows, smaller 5% steps are used (Table 4). In this instance, the focus was on the 10 mM to 500 mM window.

TABLE 4

5% Elution Windows

| Step # | % B | NaCl (mM) | Step Length (CV) |
|---|---|---|---|
| wash | 0% | 10 | 20 |
| 1 | 5% | 59.5 | 15 |
| 2 | 10% | 109 | 15 |
| 3 | 15% | 158.5 | 15 |
| 4 | 20% | 208 | 15 |
| 5 | 25% | 257.5 | 15 |
| 6 | 30% | 307 | 15 |
| 7 | 35% | 356.5 | 15 |
| 8 | 40% | 406 | 15 |
| 9 | 45% | 455.5 | 15 |
| 10 | 50% | 505 | 15 |
| wash | 100% | 1000 | 20 |

Analytical Assays

Sample Processing

Prior to the samples undergoing further analysis, they were concentrated using a GE Lifesciences Vivaspin 20 (5,000 MWCO). This reduced the 20 ml fractions to 2 ml total volume. This was split into two 1 ml samples, one was sent for LC-MS/MS, and the other was kept for SDS-PAGE.

Protein Gels—SDS-PAGE

Sodium dodecyl sulfate-polyacrylamide gel electrophoresis (SDS-PAGE) was used to observe the approximate number of proteins in each FPLC salt fraction and their molecular weight. Prior to SDS-PAGE, the samples were desalted by buffer exchange. To do this, the previously mentioned 1 ml sample of the desired fraction was concentrated in a GE Lifesciences Vivaspin 2 (5,000 MWCO) and re-suspended in 25 mM Tris buffer, pH 7. The concentration and re-suspension process was repeated two more times to ensure all salt had been removed. After the last concentration step, the sample was left in its concentrated form to be loaded onto the SDS-PAGE.

A Bio-Rad Protean II system was used for the electrophoresis with SDS buffer. The SDS buffer is made as a 10× stock, where the 1× running buffer is 25 mM Tris, 192 mM glycine, and 0.1% SDS at a pH of 8.6. For visualization of the chromatography samples, a 12.5% gel was used. The samples are mixed 5:1 with a 5× loading dye.

Electrophoresis was carried out at 100V until the sample was through the stacking gel, then increased to 140V. Average run time was around 1 hour. Gels were stained using a Coomassie Blue stain (40% methanol, 10% acetic acid and 0.5% Coomassie blue) for 3 hours and then de-stained with a 10% acetic acid and 40% methanol solution. Gel images were captured by scanning on a computer flatbed scanner.

Liquid Chromatography Mass Spectroscopy (LC-MS/MS)

Samples of each FPLC salt fraction were sent to Bioproximity (Chantilly, Va.) for protein identification via liquid chromatography mass spectroscopy (LC-MS/MS). The protocol for the LC-MS/MS was provided by Bioproximity as follows.

Protein Denaturation and Digestion

Prior to digestion, proteins were prepared using the filter-assisted sample preparation (FASP) method (Wiśniewski et al. (2009) 6(5):359-62). Next, the sample was mixed with 8 M urea, 10 mM dithiothreitol (DTT), 50 mM Tris-HCl at pH 7.6 and sonicated briefly. Samples were then concentrated in a Millipore Amicon Ultra (30,000 MWCO) device and centrifuged at 13,000×g for 30 min. The remaining sample was buffer exchanged with 6 M urea, 100 mM Tris-HCl at pH 7.6, then alkylated with 55 mM iodoacetamide. Concentrations were measured using a Qubit fluorometer (Invitrogen). The urea concentration was reduced to 2 M, trypsin was added at a 1:40 enzyme to substrate ratio, and the sample incubated overnight on a Thermomixer (Eppendorf) at 37 C. The Amicon was then centrifuged and the filtrate collected.

Peptide Desalting

Digested peptides were desalted using C18 stop-and-go extraction (STAGE) tips (Rappsilber et al. (2003) Analytical Chemistry. *American Chemical Society* 75(3):663-70). For each sample, the C18 STAGE tip was briefly activated with methanol, and then conditioned with 60% acetonitrile and 0.5% acetic acid, followed by 2% acetonitrile and 0.5% acetic acid. Samples were loaded onto the tips and desalted with 0.5% acetic acid. Peptides were eluted with a 60% acetonitrile, 0.5% acetic acid solution and dried in a vacuum centrifuge (Thermo Savant).

Liquid Chromatography-Tandem Mass Spectrometry

Peptides were analyzed by LC-MS/MS. LC was performed on an Easy-nanoLC II HPLC system (Thermo). Mobile phase A was 94.5% MilliQ water, 5% acetonitrile, 0.5% acetic acid. Mobile phase B was 80% acetonitrile, 19.5% MilliQ water, 0.5% acetic acid. The 120 min LC gradient ran from 2% B to 50% B over 90 min, with the remaining time used for sample loading and column regeneration. Samples were loaded to a 2 cm×100 um I.D. trap column positioned on an actuated valve (Rheodyne). The column was 13 cm×100 μm I.D. fused silica with a pulled tip emitter. Both trap and analytical columns were packed with 3.5 μm C 18 resin (Magic C 18-AQ, Michrom). The LC was interfaced to a dual pressure linear ion trap mass spectrometer (LTQ Velos, Thermo Fisher) via nano-electrospray ionization. An electrospray voltage of 2.4 kV was applied to a pre-column tee. The mass spectrometer was programmed to acquire, by data-dependent acquisition, tandem mass spectra from the top 15 ions in the full scan from 400-1400 m/z. Dynamic exclusion was set to 30 seconds.

Data Processing and Library Searching

Mass spectrometer RAW data files were converted to MGF (Mascot generic format) using msconvert (Kessner et al. (2008) *Bioinformatics* 24(21):2534-6). Detailed search parameters are printed in the search output XML (extensible markup language) files. All searches required strict cryptic cleavage, up to three missed cleavages, fixed modification of cysteine alkylation, variable modification of methionine oxidation and expectation value scores of 0.01 or lower. Searches used the sequence libraries: UniProt *Escherichia coli* (strain B/BL21-DE3, The UniProt Consortium (2012) *Nucleic Acids Research* 40(Database issue):D71-5), the common Repository of Adventitious Proteins (cRAP) (*The Global Proteome Machine. Common Repository of Adventitious Proteins*, 2012.01.01) and the given sequence for plasmid product GST-PTH-CBD. MGF files were searched using X!!Tandem (Craig et al. (2004) *Bioinformatics* 20(9): 1466-7) using both the native and k-score (MacLean et al. (2006) *Bioinformatics* 22(22):2830-2) scoring algorithms and by the Open Mass Spectrometry Search Algorithm (OMSSA) (Geer et al. *Journal of Proteome Research* 3(5): 958-64). All searches were performed on Amazon Web Services-based cluster compute instances using the Proteome Cluster interface. XML output files were parsed and non-redundant protein sets determined using MassSieve. Proteins were required to have two or more unique peptides across the analyzed samples with E-value scores of 0.01 or less, 0.001 for X!Hunter and protein E-value scores of 0.0001 or less.

Protein Quantitation

Proteins were quantified the spectral counting method (Liu et al. (2004) *Analytical Chemistry* 76(14):4193-201). This results in a hit count, which is approximate of protein concentration in the sample.

Database Construction

Compilation of Data

The received LC-MS/MS data was imported into Microsoft Access 2010 for data management. The EcoGene's EcoTools Database Table Download (Rudd K E. Database Table Download|EcoGene 3.0. Department of Biochemistry and Molecular Biology R-629, University of Miami Miller School of Medicine; 2012) was used to supplement the received LC-MS/MS data with additional genomic and proteomic data. The data added were: the protein length (in amino acids), direction of replication (clockwise or counterclockwise), left end position of the gene (in base pairs), right end position of the gene (in base pairs), molecular weight of the protein, common gene name, synonym gene name, protein name, protein function, description, GenBank GI ID(Benson et al. (2013) GenBank. *Nucleic acids Research* 41(Database issue):D36-42) and UniProtKB/Swiss-Prot ID (The Uniprot Consortium (2012) *Nucleic acids Research* 40(Database issue):D71-5). The EcoGene Cross Reference Mapping and Download tool was used to Bnum (Blattner number) (Blattner et al. (1997) *Science* 277(5331):1453-62). Microsoft Access was used to build relationships between the various datasets that allowed for searches across the compiled database.

Gene essentiality data were retrieved from Gerdes et al. (2003) *J. Bacteriol.* 185(19):5673-84) which compiles gene essentiality from their own research as well as the Profiling of *E. coli* Chromosome (PEC) database (Hashimoto et al. (2005) *Molecular Microbiology* 55(1):137-49; Kato and Hashimoto (2007) *Molecular Systems Biology* 3(132):132; and Kang Y et. al. (2004) *J. Bacteriol.* 186(15):4921-30).

All of the compiled data represent a portion of the DEAE separatome database and are the foundation for future work in this area. This example describes a DEAE separatome unique to choice of resin and loading condition (pH and NaCl concentration). Other combinations of resins and loading conditions can be used to define additional separatomes, the compilation of which is of commercial significance.

Data Manipulation

Proteins within a separatome can reduce chromatographic efficiency. In order to determine the priority of genes to be deleted, each gene was given a score for each elution window (shown in Table 4). This criterion, or importance score, was defined by:

$$\text{importance}_i = \sum_j \left[ b_1 \left( \frac{y_{cj}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i \quad \text{Equation 3}$$

with the following definitions: b1=scaling parameter; $y_{cj}$ and $y_{max}$=concentration of mobile phase eluent in fraction (j) and maximum value, respectively; and $h_{i,j}$ and $h_{i,total}$=the amount of protein (i) in fraction (j) and total bound protein (i), respectively; and $h_{j,total}$=total amount of protein in fraction (j); MWi=molecular weight of protein (i); MWref=molecular weight of a reference protein within the separatome; α=steric factor; and i=protein.

We chose to define the Importance Score (IS) in this fashion because the empirically derived equation captures the characteristics of both binding and elution data without solving numerical models of multi-component liquid chromatography to define the association and dissociation rate constants.

In the function given, the score can range from 1 (high negative impact on column capacity) to 0 (low or no impact on column capacity). The summation ranges over the desired elution windows (j) and can be adjusted to cover all of the windows, or target a select few. The first ratio accounts for adsorption strength with $y_{cj}$ being the concentration of the elution solvent (in the case of ion exchange, this is NaCl) and $y_{max}$ being the maximum solvent concentration. The second ratio accounts for adsorption specificity with $h_{i,j}$ being the protein concentration in the window, over the total protein concentration in all windows ($h_{i,total}$). For proteins that elute in only one window, this value will be 1, where proteins that elute in multiple windows will have a lower ratio. The third ratio describes the relative amount a protein has in a given fraction, and the forth ratio accounts for the possibility of steric hindrance.

A protein that remains bound and requires stringent conditions for elution exhibits a ratio $$\left(\frac{y_{cj}}{y_{max}}\right)$$

close to, or equal to, unity, whereas a protein that emerges as a tight peak has a $$\left(\frac{h_{i,j}}{h_{i,total}}\right)$$

ratio close to unity. Finally, a $$\left(\frac{h_{i,j}}{h_{j,total}}\right)$$

ratio is close to unity if it constitutes the majority of fraction or elution window(j).

Molecular weight is included in the fourth ratio of the IS since it plays a role when the column is under fully loaded or breakthrough loading conditions. This ratio is raised to $\alpha$, where the $\alpha$ term accounts for column saturation, wherein when the column is fully saturated $\alpha=1$ and when the column is unsaturated $\alpha<1$. This causes the MW term to be dropped in cases where the column is not fully saturated, and thus molecular weight, or the approximate size, of the protein does not factor into overall column capacity.

The IS equation is then used to analyze a separatome database. When used to analyze the aforementioned DEAE separatome database for example, gene rpoB is present in all fractions of the gradient and has a $h_{i,total}$ value of 1120, with ratio values of $$\left(\frac{h_{i,j}}{h_{i,total}}\right)$$

ranging from $8.98\times10^{-3}$ to 0.52. For proteins that elute in only one or two windows, for example gene rsd, this ratio will be close to 1. The protein resulting from gene skp only elutes in one window, and thus has a $h_{i,total}$ value of 17 and a single non-zero $$\left(\frac{h_{i,j}}{h_{i,total}}\right)$$

ratio value of 1. For gene rpoB in the 100 mM elution window, the ratio of $$\left(\frac{h_{i,j}}{h_{j,total}}\right)$$

is $1.8\times10^{-3}$, indicating that the gene product of rpoB is a minimal contributor to contamination in that elution window. The fourth ratio accounts for steric hindrance as a function of molecular weight. Again, the gene product of rpoB has a molecular weight of 150 kDa. This molecular weight is divided by the protein with the largest molecular weight, mukB at 170 kDa, to yield a ratio of 0.88. In this case, the $\alpha$ term is 1 because the column was loaded to 10% breakthrough. Finally the $b_1$ term for rpoB is zero, thus forcing the IS to zero, because gene rpoB is considered essential for cellular growth. The $b_1$ term for skp is 1 because the gene product is considered unessential. This demonstrates that while the importance of HCP contaminants can be ranked via the importance equation, their deletion, modification, inhibition, etc., to improve chromatographic separation capacity may not be feasible due to their essentiality for acceptable cell growth, viability, etc., in fermentation. As discussed earlier in connection with the definition of "essential genes", however, there are potential ways to circumvent this problem.

Table 5 presents the calculations for the aforementioned in tabular format, describing the mathematics associated with rpoB and skp for the 100 mM NaCl fraction (j=100); the math was repeated for all the remaining salt fractions (j=50, 150, 200, 250, 300, 350, 400, 450, 500, 1000) and summed to determine the total importance score and thus determine the ranking in terms of the gene's negative impact on total column capacity. A high importance score indicates a large negative impact on chromatographic separation efficiency.

TABLE 5

| Gene Name | NaCl Fraction (j) | $b_1$ | $\left(\frac{y_{c,j}}{y_{max}}\right)$ | $\left(\frac{h_{i,j}}{h_{i,total}}\right)$ | $\left(\frac{h_{i,j}}{h_{j,total}}\right)$ | $\left(\frac{MW_i}{MW_{ref}}\right)$ | $\alpha$ | $IS_{100}$ |
|---|---|---|---|---|---|---|---|---|
| rpoB | 100 | 0 | 100/1000 | 12/1120 | 12/20556 | 150632/170230 | 1 | 0 |
| skp | 100 | 1 | 100/1000 | 17/17 | 17/20556 | 17688/170230 | 1 | 8.6E−06 |

Once the final IS is determined, rpoB tied for last place in the ranking due to the $b_1$ of zero (due to gene essentiality, as disclosed by Gerdes et al. (2003) *J. Bacteriol.* 185(19):5673-84), and skp is ranked 333. From the IS, it can be determined that while rpoB has a large impact on column capacity, it cannot be deleted due to its impact on cell viability and skp has such little impact that it does not merit deletion.

In contrast to literature such as Liu et al. (2009) *J. Chromatog. A* 1216:2433-2438, Bartlow et al. (2011) *Protein Expression and Purification* 78:216-224, Bartlow et al. (2012) *American Institute of Chemical Engineers Biotechnol. Prog.* 28:137-145, and Campbell et al. U.S. Pat. No. 8,178,339, which might suggest the removal of skp if a target recombinant protein would co-elute in the 100 mM fraction, the methodology presented in this example demonstrates that the potential column capacity improvement from this deletion would result in a negligible column capacity improvement of approximately less than 0.01%. This demonstrates that the present separatome concept employing the importance equation provides a novel quantitative and rational means of identifying and ranking host cell proteins that negatively impact chromatographic separation capacity, and therefore chromatographic selectivity and purity of the final recovered target product. Once identified and ranked in this way, such host cell chromatography nuisance proteins can be deleted, modified, or inhibited to produce optimized host cells for recombinant expression of a broad spectrum of target peptides, polypeptides, and proteins, where such cells still maintain good (or possibly even improved) fermentation characteristics such as growth rates, viability, protein expression, etc.

The second and third equations define how much capacity is recovered when the protein is removed, and the overall capacity recovery as one modifies, deletes, or inhibits n genes, respectively $$\text{recovery potential}_i = h_{i,total}/h_{total,ms} \text{ and} \quad \text{Equation 1}$$

$$\text{capacity recovery} = 100\% \times \sum_{i=1}^{n} \text{recovery potential}_i \quad \text{Equation 2}$$

Homologous Recombination

Figure 5:
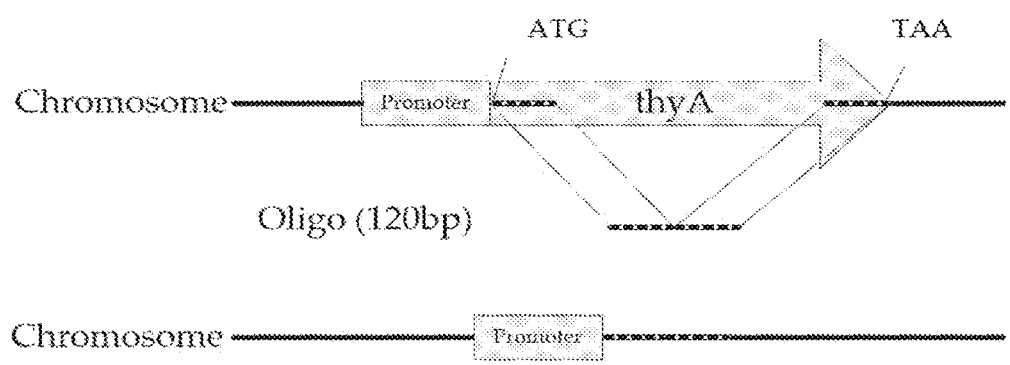
FIG. 5 shows removal of thyA prior to homologous recombination.

Flexible Recombineering Using Integration of thyA (FRUIT) as described by Stringer et al., FRUIT, a Scar-Free System for Targeted Chromosomal Mutagenesis, Epitope Tagging, and Promoter Replacement in *Escherichia coli* and *Salmonella enterica*. *PloS one*. 2012 January; 7(9):e44841, a modification of the Datsenko λ-Red homologous recombination system, was used to delete the targeted genes from the genome of *E. coli* strain MG1655. This is a new system, which utilizes the gene thyA as a growth oriented positive and negative selection marker. The method begins by creating an MG1655 ΔthyA strain (LTS00; Table 7) by swapping the gene for an oligonucleotide designed to have 60 bp of homology at the beginning and the end of the thyA gene. FIG. 5 shows the process by which this deletion is performed.

To Delete thyA

This oligonucleotide was ordered as two linear ssDNA fragments from Integrated DNA Technologies (Coralville, Iowa). The fragments were hydrated in Qiagen EB buffer (Tris, pH 8, 1.4M NaCl) and mixed at a 1:1 ratio. The mixture was then placed in an MJ Research PTC-200 DNA Engine thermocycler that was programed to heat to 98° C. and then drop the temperature by 2° C. every 30 seconds until it reached 25° C.

To delete thyA, MG1655+pKD46 (described in Datsenko et al. and Stringer et al., supra) was cultured overnight at 30° C. in LB plus ampicillin (100 µg/ml). The following morning, the overnight culture was sub-cultured 1:100 into 5 ml of fresh LB-ampicillin with 0.2% L-arabinose (w/v) and allowed to grow for approximately three hours until the culture reached an $OD_{600}$ (determined using a HP DU800) of 0.6 to 0.8. All proper controls were also taken to validate the recombination event. To prepare the cells for electroporation, the 5 ml induced culture was split into four 1 ml aliquots and moved to 1.5 ml microfuge tubes. The final 1 ml was refrigerated for later analysis or for further sub-culturing. The microfuge tubes were centrifuged for 60 seconds at 14,000 rpm in a cooled (placed in a refrigerator at 2° C.) bench-top microfuge centrifuge (Eppendorf, MiniSpin). The supernatant was discarded by gently pouring off the liquid and then the pellet was placed on ice. The pellet was then re-suspended in 1 ml of chilled ddH2O and then centrifuged again. This process was repeated once more. After the supernatant is poured off the final time, there is roughly 100 µl of liquid left in the tube. Next, the cells are re-suspended in the remaining fluid and kept on ice. To this, the prepared linear fragment is added, in this case the thyA deletion template, various concentrations, usually ranging from 200-1000nmol. This mixture was then pipetted into chilled sterile electroporation cuvettes (Bio-Rad, 0.1 cm gap). The sample was then electroporated using a Bio-Rad MicroPulser set to Ec1 (*E. coli*, 0.1 cm cuvette, 1.8 kV, one pulse). Next, 1 ml of LB containing ampicillin (50 µg/ml), thymine (100 µg/ml), and trimethoprim (20 µg/ml) (LB-amp-thy-tri) was gently added directly to the cuvette before incubating the sample at 30° C. with shaking for 3 hours. Since the strain now lacks thyA, it is necessary to supplement the medium with thymine. Trimethoprim acts as a secondary selector because if the strain still contains an active thyA gene, the trimethoprim is toxic. After that time, the cultures were streaked out onto LB-amp-thy-tri agar plates and allowed to incubate at 30° C. overnight. In addition, 250 µl of each culture were sub-cultured into 5 ml of LB-ampicillin-thymine-trimethoprim and incubated overnight at 30° C. with shaking.

In summary, the gene deletion protocol is a two-step process. The first step uses thyA as a selection marker that disrupts the targeted gene. The second step removes thyA from the genome again, following the protocol described above. For the first step, strain LTS00 is grown overnight in LB-amp-thy-tri and is sub-cultured 1:100 the following morning into 5 ml LB-amp-thy-tri plus 0.2% L-arabinose. These cells are allowed to grow for approximately 6 hours (growth is significantly diminished when lacking thyA) until the $OD_{600}$ reaches 0.6 to 0.8. The cells are then prepared for electroporation as described above. Prior to electroporation, 2 µl of the PCR product containing the thyA gene with homology to the gene to be deleted is added to the sample. Electroporation follows the protocol described above. After electroporation, 1 ml of LB with ampicillin (50 µg/ml) was added, and the cells were allowed to incubate for 3 hours at 30° C. with shaking. After that time, the cultures were streaked out onto LB-ampicillin (150 µg/ml) agar plates and allowed to incubate at 30° C. overnight. In addition, 250 µl of each culture were sub-cultured into 5 ml of LB-ampicillin (150 µg/ml) and incubated overnight at 30° C. with shaking.

Figure 6:
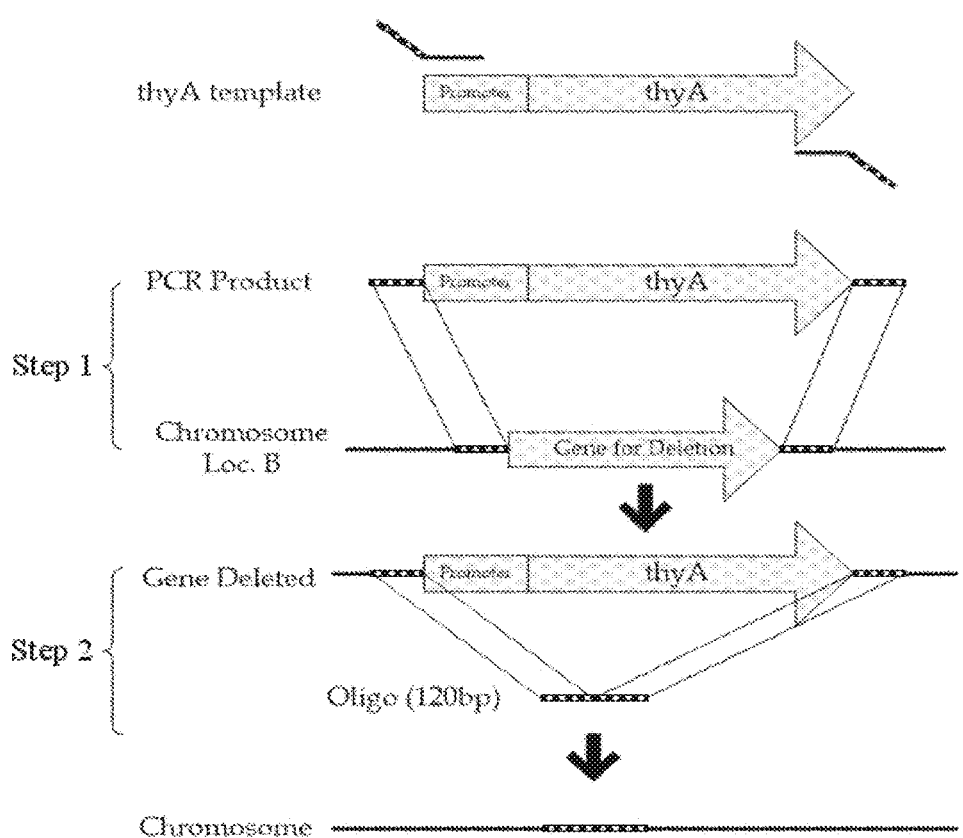
FIG. 6 shows removal of a gene targeted for deletion via a two step process.

FIG. 6 shows the process by which the selection marker is used to cause a gene deletion. Step 1 creates the intermediary thyA+ strain, where the target gene has been deleted but the selection marker remains. At this point, the cell is able to survive on thymine-depleted medium. Step 2 removes the thyA marker so that it can be used again for future gene deletions. The protocol is the same as that for the removal of thyA but the 120 bp oligonucleotide has homology to the new gene target and removes thyA and its promoter.

Successful deletion of the gene was confirmed via PCR amplification of the deleted region and agarose gel electrophoresis. The amplified regions were also sent for genomic sequencing to further confirm that the homologous recombination event successfully occurred.

TABLE 6

Deletion Fragments.
Deletion Fragments

| Name | Gene Target | Sequence |
|---|---|---|
| thyAdt | thyA | GCAAAATTTCGGGAAGGCGTCTCGAAGAATTTAA CGGAGGGTAAAAAAACCGACGCACACGTGTTGCT GTGGGCTGCGACGATATGCCCAGACCATCATGAT CACACCCGCGACAATCAT (SEQ ID NO: 4) |
| metHdt | metH | TTTGTTGAATTTTTATTAAATCTGGGTTGAGCGT GTCGGGAGCAAGTGCTGGGGTATGACGCGGACTG ATTCACAAATCTGTCACTTTTCCTTACAAC (SEQ ID NO: 5) |
| entFdt | entF | GGCGTACTCTGACACCGACGAATTTTACCCAGTT GCAGGAGGCACACGCGCAACGCTAAACAGGTAAA TTAATATTATTTATAAACCCATAATTAC (SEQ ID NO: 6) |
| tgtdt | tgt | CGCTGGTTTAAAACGTTGGACTGTTTTTCTGACG TAGTGGAGAAAAACCACCTTTGAACGTTGATTAA TATTAATAATGAGGGAAATTTAATGAGCT (SEQ ID NO: 7) |
| mrdt | rnr | GTGGAGTGACGAAAATCTTCATCAGAGATGACAA CGGAGGAACCGAGAAGAAAAAAGTGGCAGAGTGA TCAATACCCTCTTTAAAAGAAGAGGGTTA (SEQ ID NO: 8) |
| ycaOdt | ycaO | TAAAACCCGTATTATTGCGCGCTTTCCGTACGAC TAAAGTGATTTTCGCAGCATTCTGGGCAAAATAA AATCAAATAGCCTACGCAATGTAGGCTTA (SEQ ID NO: 9) |

These results demonstrate how the separatome can be defined for a chromatographic technique, ion exchange in particular, and can be used to design and construct novel host cells that have certain genes deleted, modified, or inhibited. For example, Table 6 describes ten separate *E. coli* MG1655 derivatives that have one or more gene deletions associated with high affinity host cell proteins. These strains in their current form can be used to express a target recombinant protein and will have enhanced separation efficiency, column capacity in particular, as these proteins are contained in several fractions of high salt concentration.

TABLE 7

E. coli Deletion Strains

| Name | Genotype |
|---|---|
| MG1655 | Wild Type: F-, λ-, rph-1 |
| LTS00 | ΔthyA |
| LTS01+ | ΔmetH |

TABLE 7-continued

E. coli Deletion Strains

| Name | Genotype |
|---|---|
| LTS01 | ΔthyAΔmetH |
| LTS02+ | ΔmetHΔentF |
| LTS02 | ΔthyAΔmetHΔentF |
| LTS03+ | ΔmetHΔentFΔtgt |
| LTS03 | ΔthyAΔmetHΔentFΔtgt |
| LTS04+ | ΔmetHΔentFΔtgtΔrnr |
| LTS04 | ΔthyAΔmetHΔentFΔtgtΔrnr |
| LTS05+ | ΔmetHΔentFΔtgtΔrnrΔycaO |

Table 8 lists high priority genes for DEAE ion exchange media. This table was generated by analyzing the DEAE separatome database with the importance score (Equation 3). In this iteration of analyisis, the IS variables were specifically defined as follows. The summation included NaCl fractions 60 mM, 109 mM, 159 mM, 208 mM, 258 mM, 307 mM, 357 mM, 406 mM, 456 mM, 505 mM, 1000 mM. b1=1, $y_{max}$=1000 mM; for $h_{i,j}$, $h_{i,total}$, and $h_{j,total}$, a count of distinct peptides identified in the sample was used to indicate amount of protein; MWref=170 kDa (the molecular weight of the largest gene product, mukB); α=1.

Future strains of the LTS series of Table 7 will have additional genes, alone or in various combinations, identified in Tables 8 and 9, deleted, modified, and/or inhibited as the recovery capacity is pushed toward higher values.

TABLE 8

High priority genes of the DEAE separatome, Loading pH 7
Gene Name rpoC
rpoB
hldD
metH
entF
mukB
tgt
rnr
glgP
recC
ycaO
glnA
ptsI
metE
sucA
hrpA
groL
gatZ
speA
thiI
nusA
tufA
degP
clpB
rapA
metL
ycfD
nagD
ilvA
fusA
cyaA
gldA
dnaK
ygiC
gyrA
glnE
carB
ppsA
degQ
usg
ilvB

TABLE 8-continued

High priority genes of the DEAE separatome, Loading pH 7
Gene Name thrS
recB
entB
dusA
typA
prs
cysN
atpD
purL The high priority genes in Table 8 are listed in descending rank order, from greater importance to lesser importance, according to their importance score as calculated using Equation 3.

TABLE 9

Further High Priority Genes of the DEAE Separatome, Loading pH 7
Gene Name hldD
cutA
rraA
usg
tufA
nagD
ycfD
ptsI
gldA
slyD
speA
prs
tgt
argG
glnA
rpoB
hemL
groL
rpoC
metE
typA
entB
fusA
csrA
gatZ The high priority genes in Table 9 are listed in descending rank order, from greater importance to lesser importance, according to their importance score as calculated using Equation 3. The summation included NaCl fractions 60 mM, 109 mM, 159 mM, 208 mM, 258 mM, 307 mM, 357 mM, 406 mM, 456 mM, 505 mM, 1000 mM. b1=1, $y_{max}$=1000 mM. For $h_{i,j}$, $h_{i,total}$, and $h_{j,total}$, mass spectroscopy data were used to determine the amount of protein, which was defined as the number of confident sequencing events that matched to peptides associated with a given protein ($h_i$). MWref=170 kDa (the molecular weight of the largest gene product, mukB); α=0. Six genes listed in Table 9 are unique compared to those listed in Table 8: cutA, rraA, slyD, argG, hemL, and csrA.

The genes listed in Tables 8 and 9 have been determined by the inventors to represent preferred/suitable genes to target for deletion, etc., for improving the chromatographic separation efficiency of target host cell or target recombinant peptides, polypeptides, or proteins expressed in the E. coli host cells disclosed herein via DEAE anion exchange chromatography adsorbed at pH 7 and 60 mM NaCl.

As would be apparent to one of ordinary skill in the art, the genes listed in each of Tables 8 and 9 can advantageously be used alone, or together with one another in various combinations, to improve chromatographic separation efficiency of peptides, polypeptides, and proteins expressed in E. coli host cells. In addition, the genes listed in each of these two tables can further advantageously be used in various combinations with one another as well.

The number of such combinations of genes, either for Table 8 alone, Table 9 alone, or Tables 8 and 9 together, is determined by the combination equation:

$$\frac{n!}{r!(n-r)!} \quad \text{Equation 6}$$

where n is the set of genes out of which selection occurs (the unique set of genes from Table 8 or Table 9 taken alone or in combination, i.e., without repetition), and r is the number of genes selected for deletion, modification, and/or inhibition together.

The number of combinations of n genes selected r at a time is equal to n factorial divided by r factorial multiplied by n minus r factorial, or $$nCr = n!/(r!((n-r)!)) \quad \text{Equation 7}$$

where nCr represents the number of possible unique combinations of gene selections from a master group with n distinct genes.

The number of genes (r) selected can be 2 or more, 3 or more, 4 or more, 5 or more, 6 or more, 7 or more, 8 or more, 9 or more, 10 or more, 11 or more, 12 or more, and so on, encompassing all the genes listed in Tables 8 and 9. By way of example only and not limitation, the number of genes (r) selected can be in ranges from 1-12 and any range therein, including the end points; 2-12 and any range therein, including the end points; 3-12 and any range therein, including the end points; 4-12 and any range therein, including the end points; 5-12 and any range therein, including the end points; 6-12 and any range therein, including the end points; 7-12 and any range therein, including the end points; 8-12 and any range therein, including the end points; 9-12 and any range therein, including the end points; 10-12 and any range therein, including the end points; or 11-12. Twelve is merely an illustrative upper limit: upper limits for each table include all the listed genes, including any range of genes therein.

As a non-limiting example, selecting 5 genes for deletion from those listed in Table 8 and using the combination equation, i.e., when n equals 50 and r equals 5, results in 2,118,760 unique combinations, one of which includes five genes in the list of non-essential genes published by Gerdes et al. (2003), discussed below in Section II.

As the genes listed in Tables 8 and 9 have been identified as high priority candidates for deletion, modification, or inhibition to construct improved E. coli host cell strains for target peptide, polypeptide, and protein expression and purification, it is highly likely, and fully expected, that most, if not all, combinations of these genes will be effective in improving separation efficiency of target biomolecules from host cells in which these biomolecules are expressed and in which combinations of these genes are deleted, modified, or inhibited.

Deletion, modification, and/or reduction/total inhibition of expression of various combinations of genes listed in Tables 8 and 9 as calculated above includes both sequential (contiguous) and non-sequential (non-contiguous) combinations (which involve "skipping" or omitting listed genes), as well as random combinations of high ranking genes listed in these Tables, i.e., any combinations predicted by equations 6 and 7. Essential genes that can be modified by the methods discussed below can also be included in any of these gene combinations when necessary.

A consideration in designing such combinations involves gene essentiality. Essential genes can be deleted, etc., if the modified host cells exhibit acceptable viability, growth rates, protein expression levels, etc., for the intended application. Alternatively, essential genes can be modified, for example, by reducing their expression by replacing their naturally occurring promoters with weaker promoters, introducing strategic point mutations to replace amino acids involved in resin binding while still maintaining satisfactory levels of gene/protein activity, or replacing endogenous *E. coli* genes with genes from other organisms that perform the same or similar functions and that do not significantly adversely affect chromatographic separation efficiency and separation capacity, or cell growth, viability, and capacity for expression, rather than deleting them entirely. Such replacement genes include heterologs, homologs, analogs, paralogs, orthologs, and xenologs. These strategies facilitate improvements in chromatographic separation efficiency even when interfering host cell proteins are expressed from essential genes. In addition, as discussed above in the definition of "essential genes", various feeding strategies can be used in the present host cells and methods to circumvent potentially deleterious effects due to deletion, etc., of essential genes that would otherwise adversely impact chromatographic separation efficiency if present.

The effectiveness of any of the various possible combinations of genes targeted for deletion, selected from either Table 8 alone, Table 9 alone, or Tables 8 and 9 together, as described above in improving chromatographic separation efficiency of target host cell or target recombinant peptides, polypeptides, and proteins can be determined without undue experimentation by the methods disclosed herein.

Section II.
Cloning Strains and Vectors: *E. coli* Strain K-12
Construction of Knockout Strain K-12 MG1655
Parent Cell Line Selection There are two predominant strain derivatives within *E. coli*: the B-strains and the K-12-strains, with the ones used herein to demonstrate separatome principles being B-strain BL21 (DE3) (note Section I., above) and K-12-strain MG1655, exemplified in this section.

While the data generated in Section I. described above were based on the proteome of BL21, it was desirable to build a knockout strain in the K-12 derivative MG1655 as well. However, it should be noted that besides K-12 strain MG1655, many other strains can be used in embodiments of this invention, including those listed in, and immediately below, Table 1.

Fortunately, the differences between the two strains are minimal. The most apparent difference between the two strains is that the BL21(DE3) strain has the T7 RNA polymerase incorporated into its genome under the control of the lac repressor, allowing for the use of T7 promoters for tight control of recombinant expression (Studier and Moffatt (1986), *Journal of Molecular Biology* 189 (1): 113-30). Other than that modification, the two strains are otherwise highly similar. In fact, the B and K genomes align with greater than 99% base-pair matching over approximately 92% of their genome (Jeong (2009), *Journal of Molecular Biology* 394(4): 644-652). The remaining un-matched segments can be mostly accounted for as insertion sequences, and the remaining differences are a few full-gene deletions and single-nucleotide polymorphisms that cause frame shifts (Studier, (2009) *Journal of Molecular Biology* 394(4): 653-80). While these differences are interesting in the scope of phylogenetics, they are minimal enough that they have little to no impact on the proteomics of the cell lines.

Genes Selected for Deletion in the K-12 Strain

Five non-essential genes (from among a list of non-essential genes published by Gerdes et al. (2003) *J. Bacteriol.* 185, (19): 5673-5684) were selected for deletion from the K-12 genome. These were metH, entF, tgt, rnr, and ycaO. Using the importance score calculated from 59-1000 mM according to importance score Equation 3, the deleted genes rank: tgt: 13, entF: 40, ycaO: 34, metH: 67, and rnr: 120. Lower rank numbers are more important than higher rank numbers, i.e., lower rank numbers reflect higher importance scores. The primers used for gene deletion and the double stranded DNA deletion templates are shown in Table 10.

TABLE 10

Deletion Templates and Primers

| Name | Base Pairs | Sequence |
|---|---|---|
| Deletion Templates | | |
| metHdt3 | 98 | GTT GTA AGG AAA AGT GAC AGA TTT GTG AAT CAG TCC GCG TCA TAC CCC AGC ACT TGC TCC CGA CAC GCT CAA CCC AGA TTT AAT AAA AAT TCA ACA AA (SEQ ID NO: 10) |
| metHdt5 | 98 | TTT GTT GAA TTT TTA TTA AAT CTG GGT TGA GCG TGT CGG GAG CAA GTG CTG GGG TAT GAC GCG GAC TGA TTC ACA AAT CTG TCA CTT TTC CTT ACA AC (SEQ ID NO: 11) |
| entFdt3 | 96 | GTA AAT ATG GGT TTA TAA ATA ATA TTA ATT TAC CTG TTT AGC GTT GCG CGT GTG CCT CCT GCA ACT GGG TAA AAT TCG TCG GTG TCA GAG TAC GCC (SEQ ID NO: 12) |
| entFdt5 | 96 | GGC GTA CTC TGA CAC CGA CGA ATT TTA CCC AGT TGC AGG AGG CAC ACG CGC AAC GCT AAA CAG GTA AAT TAA TAT TAT TTA TAA ACC CAT AAT TAC (SEQ ID NO: 13) |
| tgtdt3 | 97 | AGC TCA TTA AAT TTC CCT CAT TAT TAA TAT TAA TCA ACG TTC AAA GGT GGT TTT TCT CCA CTA CGT CAG AAA AAC AGT CCA ACG TTT TAA ACC AGC G (SEQ ID NO: 14) |
| tgtdt5 | 97 | CGC TGG TTT AAA ACG TTG GAC TGT TTT TCT GAC GTA GTG GAG AAA AAC CAC CTT TGA ACG TTG ATT AAT ATT AAT AAT GAG GGA AAT TTA ATG AGC T (SEQ ID NO: 15) |
| rnrdt3 | 97 | TAA CCC TCT TCT TTT AAA GAG GGT ATT GAT CAC TCT GCC ACT TTT TTC TTC TCG GTT CCT CCG TTG TCA TCT CTG ATG AAG ATT TTC GTC ACT CCA C (SEQ ID NO: 16) |

TABLE 10-continued

Deletion Templates and Primers

| Name | Base Pairs | Sequence |
|---|---|---|
| rnrdt5 | 97 | GTG GAG TGA CGA AAA TCT TCA TCA GAG ATG ACA ACG GAG GAA CCG AGA AGA AAA AAG TGG CAG AGT GAT CAA TAC CCT CTT TAA AAG AAG AGG GTT A (SEQ ID NO: 17) |
| ycaOdt3 | 97 | TAA GCC TAC ATT GCG TAG GCT ATT TGA TTT TAT TTT GCC CAG AAT GCT GCG AAA ATC ACT TTA GTC GTA CGG AAA GCG CGC AAT AAT ACG GGT TTA A (SEQ ID NO: 18) |
| ycaOdt5 | 97 | TAA AAC CCG TAT TAT TGC GCG CTT TCC GTA CGA CTA AAG TGA TTT TCG CAG CAT TCT GGG CAA AAT AAA ATC AAA TAG CCT ACG CAA TGT AGG CTT A (SEQ ID NO: 19) |
| Primers | | |
| metH-F | 68 | TTT GTT GAA TTT TTA TTA AAT CTG GGT TGA GCG TGT CGG GAG CAA GTG CGC CAC CCA TCA CAG CTT TA (SEQ ID NO: 20) |
| metH-R | 70 | GTT GTA GGG AAA AGT GAC AGA TTT GTG AAT CAG TCC GCG TCA TAC CCC AGG GGA AGG CGT CTC GAA GAA T (SEQ ID NO: 21) |
| entF-F | 66 | GGC GTA CTC TGA CAC CGA CGA ATT TTA CCC AGT TGC AGG AGG CAC ACG CCA CCC ATC ACA GCT TTA (SEQ ID NO: 22) |
| entF-R | 70 | GTA ATT ATG GGT TTA TAA ATA ATA TTA ATT TAC CTG TTT AGC GTT GCG CGG GGA AGG CGT CTC GAA GAA T (SEQ ID NO: 23) |
| tgt-F | 67 | CGC TGG TTT AAA ACG TTG GAC TGT TTT TCT GAC GTA GTG GAG AAA AAC GCC ACC CAT CAC AGC TTT A (SEQ ID NO: 24) |
| tgt-R | 70 | AGC TCA TTA AAT TTC CCT CAT TAT TAA TAT TAA TCA ACG TTC AAA GGT GGG GGA AGG CGT CTC GAA GAA T (SEQ ID NO: 25) |
| rnr-F | 67 | GTG GAG TGA CGA AAA TCT TCA TCA GAG ATG ACA ACG GAG GAA CCG AGC GCC ACC CAT CAC AGC TTT A (SEQ ID NO: 26) |
| rnr-R | 70 | TAA CCC TCT TCT TTT AAA GAG GGT ATT GAT CAC TCT GCC ACT TTT TTC TTG GGA AGG CGT CTC GAA GAA T (SEQ ID NO: 27) |
| ycaO-F | 67 | TAA AAC CCG TAT TAT TGC GCG CTT TCC GTA CGA CTA AAG TGA TTT TCC GCC ACC CAT CAC AGC TTT A (SEQ ID NO: 28) |
| ycaO-R | 70 | TAA GCC TAC ATT GCG TAG GCT ATT TGA TTT TAT TTT GCC CAG AAT GCT GCG GGA AGG CGT CTC GAA GAA T (SEQ ID NO: 29) |

The FRUIT method (Flexible Recombineering Using Integration of thyA) as described by Stringer et al. ((2012) PloS one. 7(9):e44841) was selected as the gene deletion method for this example for several reasons.

The predominant homologous recombination method utilizes antibiotic resistance as the selectable deletion marker, but maintenance of the pKD46 plasmid requires the presence of ampicillin. This requirement then necessitates using a different antibiotic resistance as the selection marker and growing newly transformed cells in the presence of two different antibiotics during selection (in the case that it is desirable for the plasmid to be maintained, as in this instance). Growth in the presence of dual antibiotic selection is very hard on the cells post electroporation, and additionally can cause severe growth inhibition. The growth inhibition causes the cloning process to be very slow, in addition to making it difficult to select for the clones that still have favorable growth characteristics.

Secondly, antibiotic selection markers are positive selectors only, meaning that one can only select for the presence of the resistance gene, not for the absence. After the selection marker is removed, clones must be selected by growth on antibiotic-deficient agar overnight, and then replica plated onto agar containing antibiotics and incubated again overnight. After the second overnight growth, positive clones can be identified on the first plate by the absence of growth on the second. This process takes two days for clone selection, and there is room for significant error when replica plating.

The FRUIT method utilizes gene thyA as the selection marker, which can be positively and negatively identified by the lack of thymine or the inclusion of trimethoprim, respectively. The thyA gene is returned to the genome when gene deletion is finalized, so that the final knockout host strains contain this gene. Additionally, this method requires a single plating step for clone selection for both the inclusion and removal of the marker.

The gene deletions were confirmed by PCR as well as by DNA sequencing.

Figure 7:
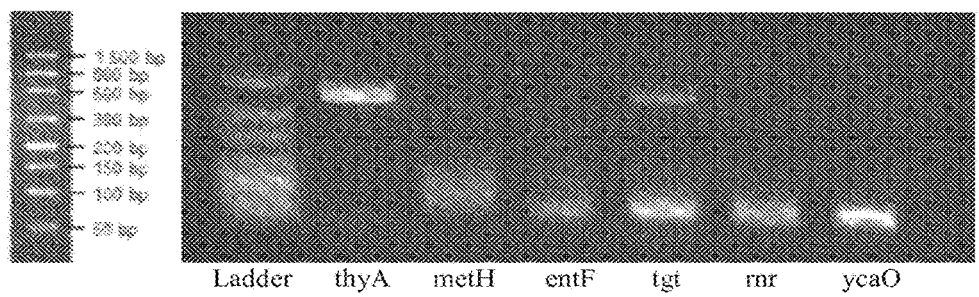
FIG. 7 shows the electrophoresis of the PCR amplification of each target gene after deletion as described in Example 2, Section II.

FIG. 7 shows the electrophoresis of the PCR amplification of each target gene after deletion. As shown, genes metH, entF, tgt, rnr, and ycaO all have 120 bp bands, which correspond to the inserted deletion fragment. The lane corresponding to tgt also shows a larger band that corresponds with the intermediate deletion step where thyA is inserted as part of the knockout process. This indicates that there is a mixture of the two clones present, and further agar plating on trimethoprim and selection needs to be performed to select for the completed clone. The smaller tgt band, in addition to the other single bands, was isolated and sent for DNA sequencing. DNA sequencing confirmed the presence of the deletion template, which confirms that the targeted genes were successfully removed from the chromosome.

Growth Studies

Figure 8:
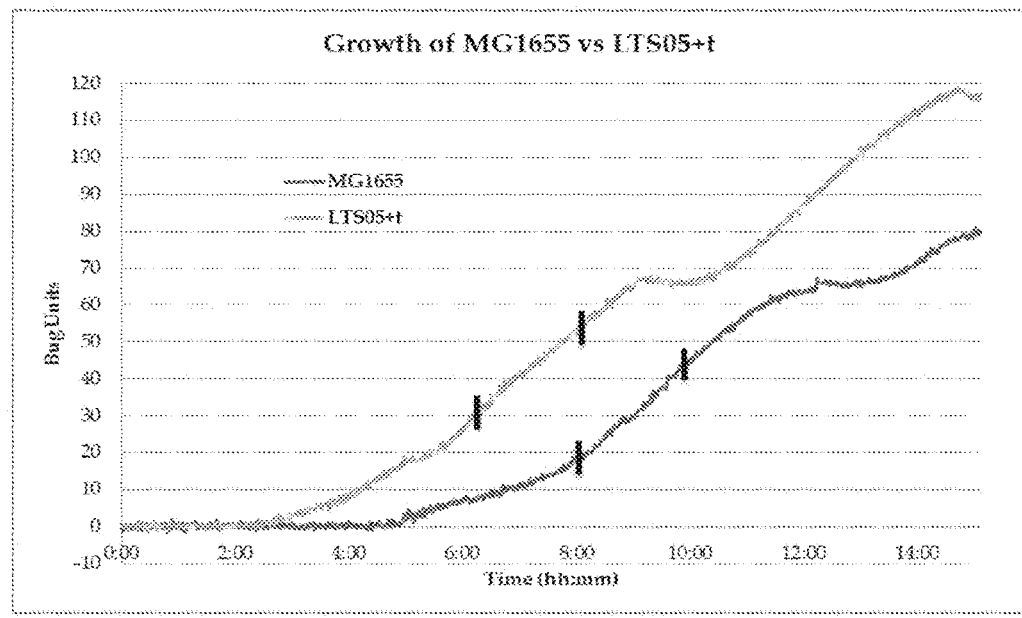
FIG. 8 shows the results of fed-batch growth studies in Example 2, Section II.

Fed-batch growth studies of K-12 knockout strain LTS05+t were conducted to determine whether growth had not been considerably diminished (i.e., whether doubling time had increased by greater than 5%) in comparison to the parent strain MG1655. Both the LTS05+t strain and the MG1655 strain contained pKD46 (ampr) plasmid and were grown in the presence of ampicillin to ensure selection of the desired strain, but neither strain was induced during growth. FIG. 8 shows the results of these two growth studies, where Bug Units, as defined by the BugEye Biomass monitor, are arbitrary optical density units that allow the user to monitor the relative growth of cultures. These units are dependent on growth conditions and linearly correlate to optical density units as measured by a spectrophotometer ($OD_{600}$)

As shown in FIG. 8, the lag phase of LTS05+t was roughly half that of MG1655. Once the growth entered log phase, both cultures grew at roughly the same rate as evaluated by comparing the slope of the curves. From time point 6:00 to 9:00, the slope of growth for LTS05+t was 0.212, whereas the slope of growth for MG1655 was 0.225 from time point 8:00 to 11:00. While exponential growth was maintained in the wild-type for roughly 10 hours and reached a final $OD_{600}$ of 48.8, LTS05+t grew exponentially for approximately 15 hours, reaching a final $OD_{600}$ of 92, almost double that of the parent strain. This growth difference could result from the tgt knockout, as previously mentioned by Noguchi et al. (1982) *J. Biol. Chem.* (11): 6544-6550.

Figure 9:
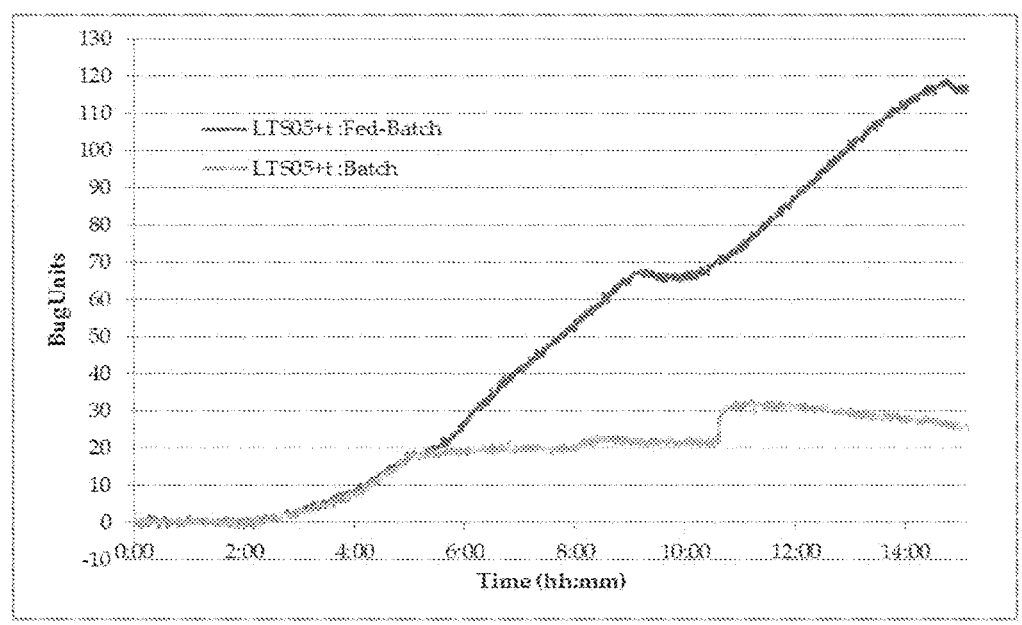
FIG. 9 shows the results of a fed-batch growth study and a standard batch growth study in Example 2, Section II.
Figure 10:
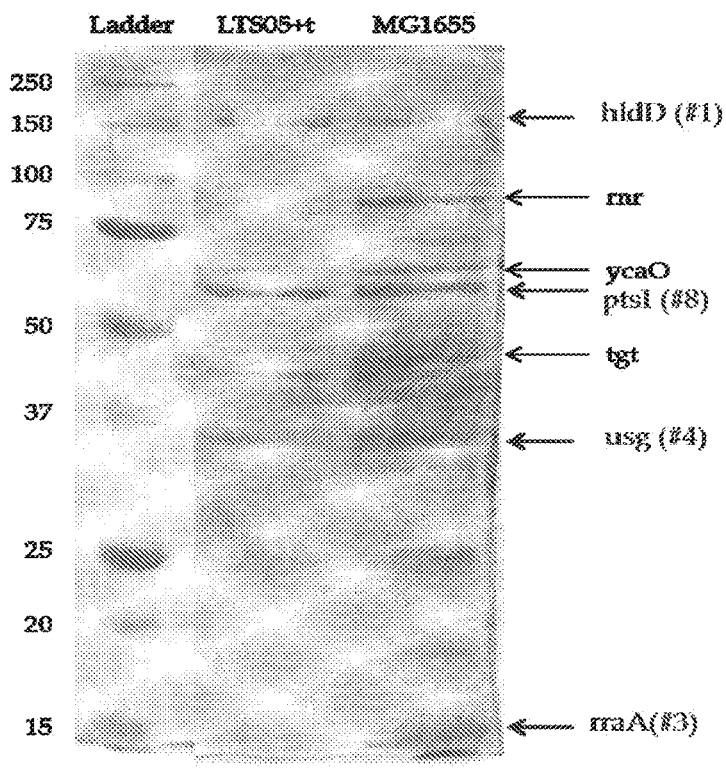
FIG. 10 shows 207 mM bound fraction for the knockout and control strain as described in Example 2, Section II. As shown, the bands corresponding to the gene products of rnr, tgt, and ycaO disappear in the LTS05+t strain. The bands corresponding to metH and entF are not visible because they do not typically bind at this salt concentration. Known key contaminants, hldD, ptsI, usg, and rraA are also labeled on the gel.

The shortened lag phase of LTS05+t was confirmed by two separate growth studies, the first run being the fed-batch discussed above, and the second run being a standard batch. These data are shown in FIG. 9, where it is evident that the transition from lag phase to log phase occurs at the same time for both batch and fed-batch fermentation.

These data demonstrate that the gene deletions do not cause a significant reduction in cellular growth and function. In fact, growth of deletion strain LTS05+t was actually improved under fed-batch conditions.

Column Capacity Measurements

The mass spectroscopy data disclosed above in Section I. provide protein quantitation through the spectral counting method. These data can be utilized to provide a rough estimation of column capacity improvement (Total Contaminant Pool: TCP) as well as the reduction of protein bound in each individual Elution Contaminant Pool (ECP) by examining the changes in theoretical protein concentration as targeted genes are removed. The results of these calculations are shown in Table 11.

TABLE 11

Predicted Improvement for the Five Selected Gene Knockouts TCP and ECP Improvement

| Total Contaminant Pool | 2.7% |
|---|---|
| 60 mM | 0.7% |
| 109 mM | 1.2% |
| 159 mM | 2.1% |
| 208 mM | 3.8% |
| 258 mM | 1.0% |
| 307 mM | 2.9% |
| 357 mM | 4.6% |
| 406 mM | 7.2% |
| 456 mM | 4.5% |
| 505 mM | 3.9% |
| 1000 mM | 1.2% |

Total Contaminant Pool Assessment

Modifications to the total contaminant pool (TCP) were measured by determining the percent of proteins that bound to DEAE under various loading conditions. This was accomplished by applying 40 mg of total protein to the column under binding conditions while collecting the flow through. The binding conditions used were 25 mM Tris, pH 7, at a salt concentration of 159 mM NaCl, which represents a typical column operating condition as used by commercial manufacturers in their purification processes. The bound proteins were then eluted using 1M NaCl, and the peak was collected. Two runs were completed at each salt concentration, per cell line, to verify the data.

A BioRad DC assay was used to determine the total protein in each collected fraction and thus determine the percent protein bound to the resin. The BioRad DC assay is a colormetric assay, requiring a standard curve to be utilized to determine protein concentration. A new BSA standard curve was built using the same Fast Protein Liquid Chromatography (FPLC) buffers as the solvent. The readable range for the assay is between 0.1 and 1 for the $A_{750}$, but is most accurate between 0.1 and 0.5 (0.2 to 2 mg protein). Since most of the samples were concentrated, they required dilution for the assay. To improve accuracy of the assay, samples were assayed at four different dilutions (often between 1× and 20×), and the measurements that fell within the readable range were used to calculate the protein concentration, which was then averaged with themselves. The FPLC runs were repeated twice. Where the data were averaged, they are presented in and Table 12 as a % avg. If only one point was used, it was because the other point was well outside the readable range of (0.1-0.5).

TABLE 12

Column Capacity at 159 mM Salt

| Strain | Data Points | Average Bound % | Error |
|---|---|---|---|
| LTS05 + t | 3 | 20.6% | ±1.1% |
| MG1655 | 1 | 30.7% | |
| Measured Improvement | | 10.1% | ±1.1 |
| Predicted Improvement | | 1.6% | |

Under these conditions, 30.7% of the proteins from the control (MG1655) bound to the resin. In contrast, 20.6% of the proteins from deletion strain LTS05+t bound the resin, representing a significant improvement (approximately 10%) in Total Column Capacity.

When compared to the theoretical TCP improvement of 2.7% (as shown in Table 10), it can be seen that the improvement is in the same order of magnitude. The gel images of the bound proteins for these two experiments show little difference (data not shown). This is likely because there are multiple proteins at the same molecular weight as the deleted proteins in the knockout strain.

These results demonstrate that the data from Section I. can be used to predict downstream column capacity improvements with relative accuracy, i.e., within the same order of magnitude.

Eluting Contaminant Pool Assessment

In addition to the measurement of column capacity changes due to Total Contaminant Pool reduction, it is important to recognize that gene deletions also change the Eluting Contaminant Pool (ECP). The assessment of the ECPs was measured using the same protocol and salt windows as described in Section I. Again, the column was loaded at 10% breakthrough to simulate commercial practices. The resulting samples were concentrated using a Vivaspin2 (GE Healthcare, 28-9322-40) with a 5 kDa cutoff to a final volume of approximately 200 µl. The samples were then analyzed by BioRad DC assay to determine total protein content, and loaded on an SDS-PAGE gel for further analysis.

Figure 11:
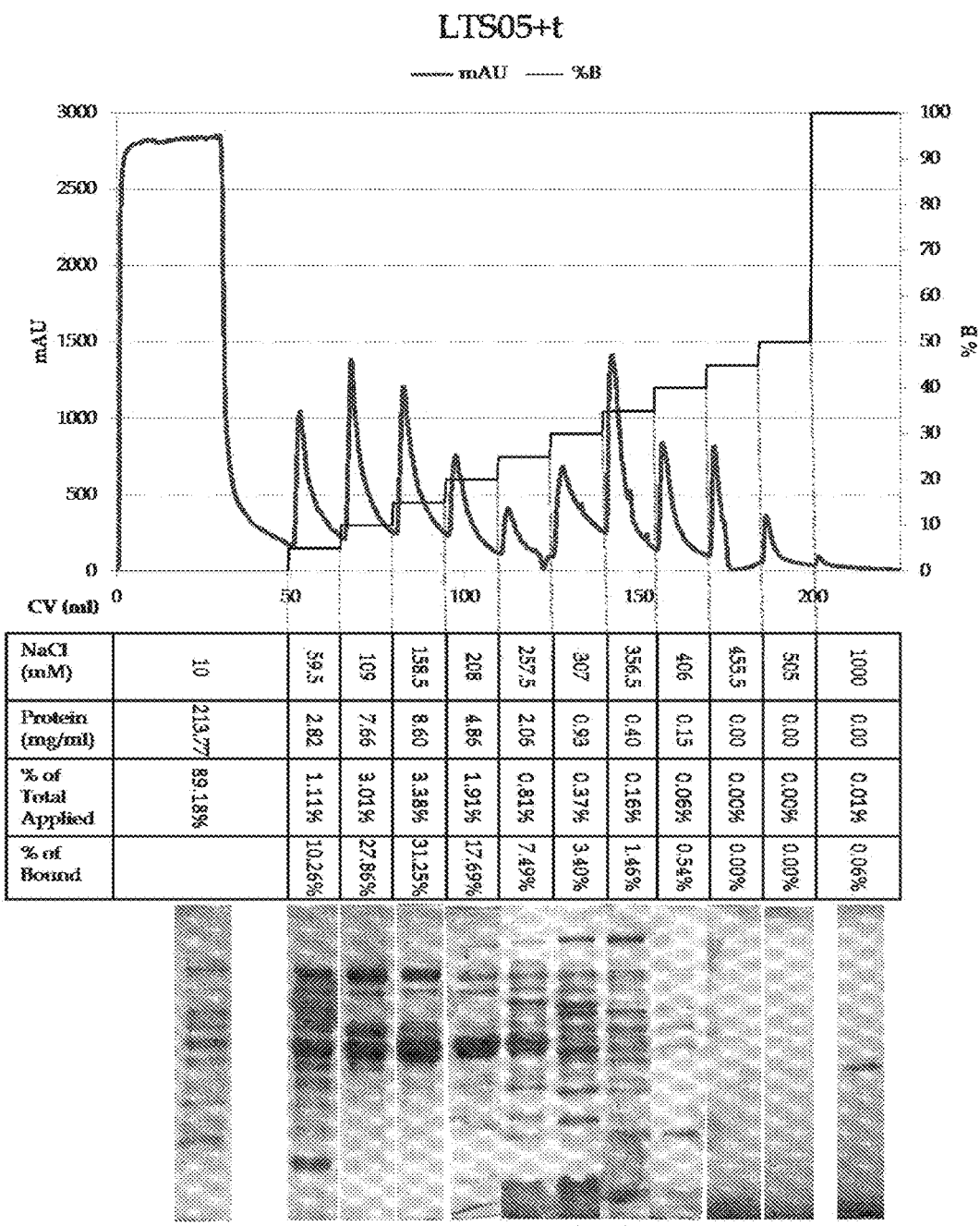
FIG. 11 shows ECP analysis of LTS05+t as described in Example 2, Section II. The top portion of the figure shows the FPLC chromatogram with the A280 on the left axis and % buffer B on the right axis. Below the chromatogram is a table showing the % buffer B converted into a mM salt concentration followed by the measured protein concentration in the window. The third row of the table shows a breakdown of how all of the applied proteins distributed over the elution windows as a percentage calculated as mg protein in elution window/total mg of protein applied to the column. The fourth row focuses on the breakdown of just the bound protein into specific windows and gives a percentage calculated as mg protein in the window/mg protein in all bound fractions (59.5 mM to 1000 mM). This number provides the best indication of how the ECP changed in the knockout strain. The bottom of the figure shows the SDS-PAGE gel for the sample.
Figure 12:
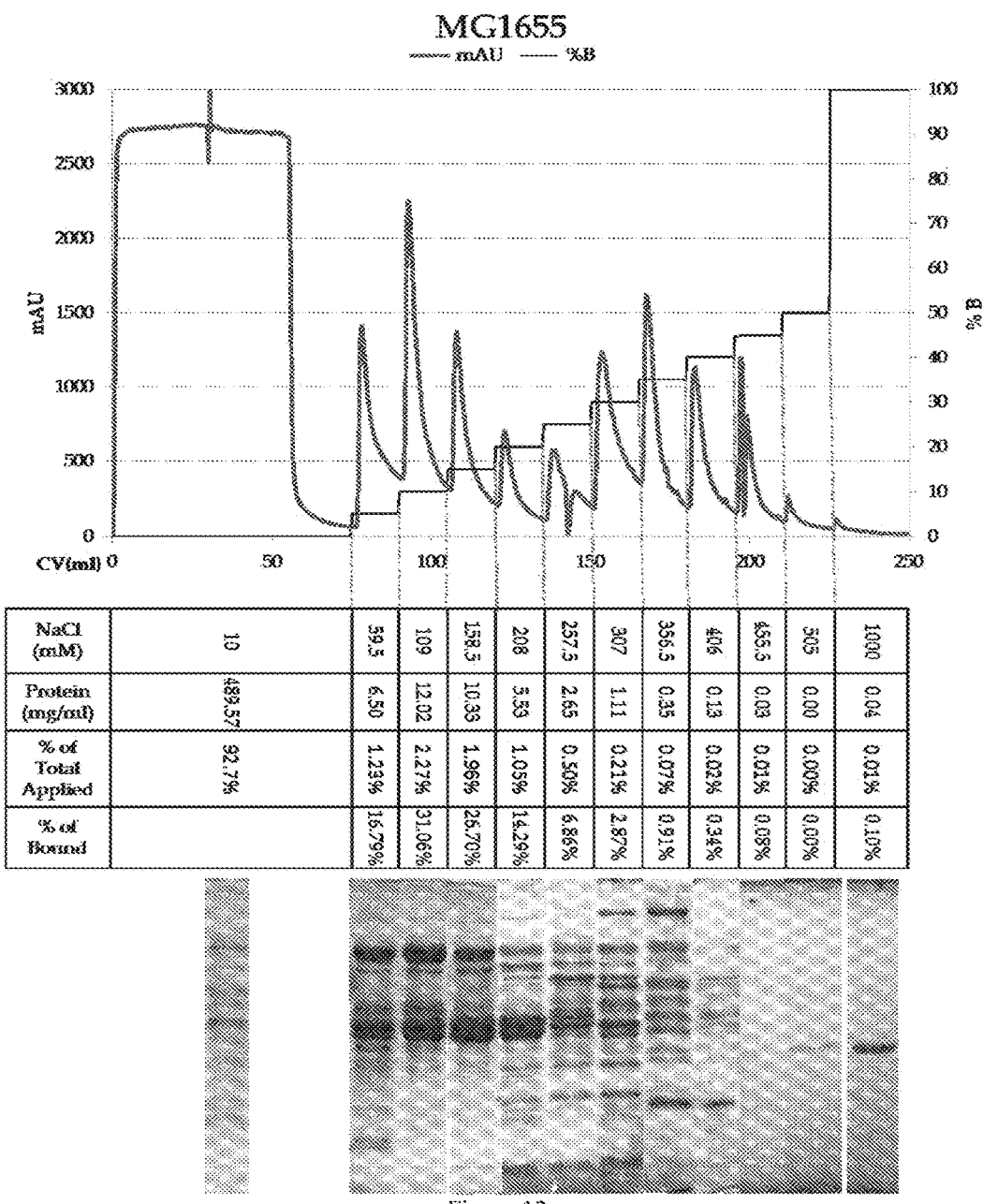
FIG. 12 shows ECP analysis of MG1655 as described in Example 2, Section II. The description of the figure is the same as that for FIG. 11.

The results of the ECP measurements for LTS05+t are shown in FIG. 11, and the results of the ECP measurements for wild-type MG1655 are shown in FIG. 12. The top portion of each figure shows the Fast Protein Liquid Chromatography chromatogram, with the $A_{280}$ on the left axis and % buffer B on the right axis. Below each chromatogram is a table showing the % buffer B converted into a mM salt concentration, followed by the measured protein concentration in the window. As each of these step fractions was 15 ml of total volume, it was necessary to concentrate the samples prior to further analysis. The samples were concentrated using a 5 kDa VivaSpin2 concentrator to reduce the final volume to approximately 200 µl. It is important to note that due to the high absorbance reading of the $A_{280}$ (outside of the linear correlation described by Beer's law) and the presence of DNA and RNA in the sample, it cannot be used as an accurate measure of protein concentration. Instead, a BioRad DC assay was used to determine the protein content of each sample, but the minimum threshold for this assay is around 0.2 mg/ml. Even after concentration, a few of the samples had a protein concentration below the readable range for the assay and are noted at 0 mg/ml despite the $A_{280}$ and subsequent SDS-PAGE indicating otherwise. The next row shows a breakdown of how all of the applied proteins distributed over the elution windows as a percentage calculated as mg protein in elution window/total mg of protein applied to the column. Note that while the percent of protein unbound seems higher than what was measured in the TCP binding experiments, this is due to the 10% overloading of the column. The fourth row focuses on the breakdown of just the bound protein into specific windows, and gives a percentage calculated as mg protein in the window/mg protein in all bound fractions (59.5 mM to 1000 mM). This number provides the best indication of how the ECP changed in knockout strain LTS05+t.

Finally, the corresponding lane from the SDS-PAGE gel is shown at the bottom. This is particularly important for the samples that were below the readable range for the protein concentration assay. Each lane of the protein gel was loaded with 25 µg of proteins, for the samples where the protein assay worked, or at the maximum volume possible for the samples that were too dilute to assay. It is important to keep in mind that each band in the protein gel may consist of multiple proteins due to the large variety of proteins being eluted in each window (from as many as 300 to as few as 70).

Figure 13:
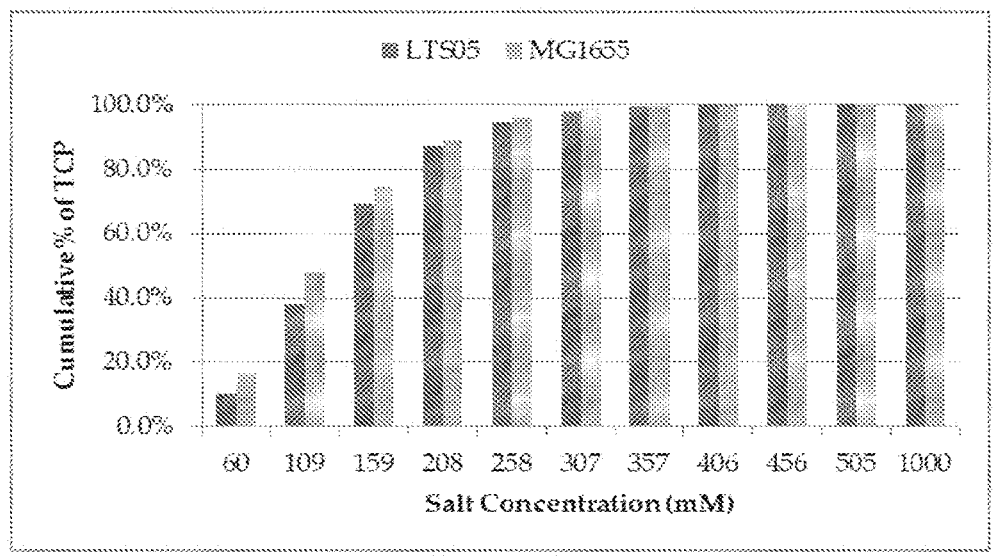
FIG. 13 shows that if the percent of bound protein for both the knockout strain and MG1655 are added cumulatively, the result is a measure of the column loading profile as described in Example 2, Section II.

If the percent of bound protein for both knockout strain LTS05+t and parent MG1655 are added cumulatively (FIG. 13), the result is a measure of the column loading profile. As shown in FIG. 13, the knockout strain LTS05+t has a reduced column binding in the earlier windows, which matches the predicted ECP reductions due to the gene deletions.

The knockout strain shows decreased percentage of proteins eluting in the 60 mM and 109 mM windows, and it also appears to have a reduced number of proteins in the 307 mM window. Additionally, by comparing the gels, the number of bands in the 456 mM window decreases from four to one (FIGS. 11 and 12). Further analysis of the elution windows by LC-MS/MS would be able to indicate where the energy was shifted metabolically and what protein concentrations were increased or decreased based upon the original deletions.

The results presented herein demonstrate that selective gene deletions in host cells that can be used to produce target peptides, polypeptides, and proteins of interest not only result in an improvement in overall column capacity, but additionally simplify specific elution windows. Exploitation of these phenomena by the concepts and methods exemplified herein will significantly improve overall purification, i.e., total recovery as well as level of purity, of target peptides, polypeptides, and proteins of interest from host cells more quickly and more economically than is possible using conventional host cells and chromatographic purification methods.

EXAMPLE 3

Data-Informed Construction of *Escherichia coli* for Improved Bioseparation: Construction of an *E. coli* Cell Line Having a Reduced Set of Host Cell Proteins Associated with DEAE Ion Exchange Chromatography A key step and potential bottleneck associated with the expression and isolation of a recombinant product is the initial chromatography capture of the protein, for as the mixture containing the target or desired protein passes over a chromatography resin, host cell proteins (HCPs) and the target compete for binding sites. This competition reduces column efficiency, and due to the binding/elution of HCPs, requires additional purification steps. This is especially problematic in the production of a biotherapeutic, for example, because the exacting requirements of purity and efficacy can require multiple purification steps, and as these steps become numerous, reduce the overall efficiency of the process. While work can be done to tailor a downstream processing regimen for a particular recombinant product, modern techniques like bioinformatics, computational genomics, and proteomics can be harnessed to improve the basic knowledge and design of the cell line used in recombinant manufacturing. Anticipated benefits of exploiting these techniques would be the development of a series of cell lines optimized for a method of purification that does not require the use of an affinity tail or biospecific interaction to achieve a high degree of efficiency.

This example describes the mapping of the *E. coli* chromosome to discern relationships between the loci of genes of key nuisance proteins (e.g., those in large concentration and/or of high binding affinity) associated with chromatographic techniques, for example DEAE ion exchange and Immobilized Metal Affinity Chromatography, to guide host cell line development with a reduced number of HCPs that are widely applicable to recombinant peptide, polypeptide, and protein production irrespective of the exact target molecule, exemplifying the separatome concept. This is an example of improving separation capacity for a chromatographic resin/buffer combination in the absence of expression of a recombinant peptide, polypeptide, or protein.

Materials and Methods

Host Cells

Wild type *E. coli* MG1655 (parent cell) was obtained from the Yale *Coli* Genetic Stock Center (New Haven, Conn.). The *E. coli* host cell line derived from this parent cell, having a reduced set of HCPs associated with DEAE ion exchange chromatography via selective gene deletions of rfaD, usg, rraA, cutA, nagD, and speA, is designated LTSF06. In this example, LTSF06 does not express any recombinant peptide, polypeptide, or protein.

Primers

The primers used for gene deletions are based on those developed and described in the Keio collection (Baba et al. (2006) *Mol Systems Biol.* 2: 2006.0008, doi:10.1038/msb4100050). Further information concerning the Keio collection is stored in their online data repository, Genobase Ver. 8.

TABLE 13

Primers used for gene deletion and PCR confirmation

| Primer name | Sequence |
|---|---|
| rfaD-F_Frt | GCAAAACCAACATCCGCCATGAAGGACTAGCTAAAAC CCAAACTAGTTTGGTGTAGGCTGGAGCTGCTTC (SEQ ID NO: 30) |
| rfaD-R_Frt | CCGGTGCCATCACATCGATTATCGCCTGGGGATAGCG CGCCTGGAGCGTGATGGGAATTAGCCATGGTCC (SEQ ID NO: 31) |
| rfaD-F2 | GCAAAACCAACATCCGCCAT (SEQ ID NO: 32) |
| rfaD-R2 | CCGGTGCCATCACATCGATTA (SEQ ID NO: 33) |
| usg-F_Frt | CGGCATCATTGCTGTGTAAACTGGGTTTTAACGCCGT TCATCATCCGGCAGTGTAGGCTGGAGCTGCTTC (SEQ ID NO: 34) |
| usg-R_Frt | GAAGACGGTGATGGGTTCGTTCGCCACCTGGGAGAGC GCCTTTTCCAGCTATGGGAATTAGCCATGGTCC (SEQ ID NO: 35) |
| usg-R2 | GCGGCATCATTGCTGTGTAA (SEQ ID NO: 36) |
| usg-F2 | GAAGACGGTGATGGGTTCGT (SEQ ID NO: 37) |
| rraA-F_Frt | CGTACTGTCAAGGGAGCGTTACTGACTAACCTGCTGT TTGTTTTAGGGATGTGTAGGCTGGAGCTGCTTC (SEQ ID NO: 38) |
| rraa-R_Frt | GAGCTGGAGCGTGAGAACAACCATCTGAAAGAACAGC AGAACGGCTGGCAATGGGAATTAGCCATGGTCC (SEQ ID NO: 39) |
| rraA-F2 | CGTACTGTCAAGGGAGCGTT (SEQ ID NO: 40) |
| rraA-R2 | AAGAGCTGGAGCGTGAGAAC (SEQ ID NO: 41) |
| cutA-F_Frt | CGACTAACATCCTTCCCCCGTCCGTTGTATAGTGACC TCTCTCTTGCGGTGTGTAGGCTGGAGCTGCTTC (SEQ ID NO: 42) |
| cutA-R_Frt | AAAGCAAAGGCTTGATCCGCGGGGACAAATTGTGAAC GTCCCGGCGCGTCATGGGAATTAGCCATGGTCC (SEQ ID NO: 43) |
| cutA-F2 | CGACTAACATCCTTCCCCCG (SEQ ID NO: 44) |
| cutA-R2 | AAAGCAAAGGCTTGATCCGC (SEQ ID NO: 45) |
| nagD-F_Frt | TTGGAGCGTCAGCATTCACTGCTGGAAAATCCATGTG CTTATGGGTTGTTGTGTAGGCTGGAGCTGCTTC (SEQ ID NO: 46) |
| nagD-R_Frt | TATTGCAGGAGCTGCGTAGGCCTGATAAGCGTAGCGC ATCAGGCAGTTTGATGGGAATTAGCCATGGTCC (SEQ ID NO: 47) |
| nagD-F2 | CGTTTCGCACTAATCTGCCG (SEQ ID NO: 48) |
| nagD-R2 | TATTGCAGGAGCTGCGTAGG (SEQ ID NO: 49) |
| speA-F_Frt | TTGGAGCGTCAGCATTCACTGCTGGAAAATCCATGTG CTTATGGGTTGTTGTGTAGGCTGGAGCTGCTTC (SEQ ID NO: 50) |
| speA-R-Frt | CGACGAGGAAGGGTTGGATTTGTCACAATAAATTGTG GCGGATTATCACCATGGGAATTAGCCATGGTCC (SEQ ID NO: 51) |
| speA-F2 | TTGGAGCGTCAGCATTCACT (SEQ ID NO: 52) |
| speA-R2 | CGACGAGGAAGGGTTGGATT (SEQ ID NO: 53) |

"Gene"-F-Frt are the forward primers with homology to antibiotic resistant cassettes with FRT sites specific to the gene of interest. "Gene"-R-Frt are the reverse primers with homology to antibiotic resistant cassettes with FRT sites specific to the gene of interest. The final 20 bp portion of the sequence is the part homologous to pKD3 or pKD4, which are plasmids containing the antibiotic resistance cassette. "Gene"-F2 are the forward primers with homology to the gene of interest and homology to the gene specific FRT-antibiotic resistant cassette, depending on the design. "Gene"-R2 are the reverse primers with homology to the gene of interest and homology to the gene specific FRT-antibiotic resistant cassette, depending on the design.

Construction of the Knockout Strain

The DEAE separatome database presented in Example 2 was utilized to provide the raw protein data needed for the importance score calculation. Six non-essential genes were selected for deletion from the genome based on their importance score (IS) determined from importance equation 3:

$$\text{importance}_i = \sum_j \left[ b_1 \left( \frac{y_{cj}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i$$

The summation included NaCl fractions 60 mM, 109 mM, 159 mM, 208 mM, 258 mM, 307 mM, 357 mM, 406 mM, 456 mM, 505 mM, 1000 mM. $b1=1$, $y_{max}=1000$ mM. For $h_{i,j}$, $h_{i,total}$, and $h_{j,total}$, the mass spectroscopy data that reported the number of confident sequencing events that matched to peptides associated with the given protein was used to indicate amount of protein; MWref=170 kDa (the molecular weight of the largest gene product, mukB); $\alpha=1$.

The genes selected for deletion in this example were rfaD, usg, rraA, cutA, nagD, and speA.

Knockouts were performed via homologous recombination according to the protocol described by Datsenko and Wanner (Datsenko et al. (2000) *PNAS* 97(12):6640-5), which utilizes the Lambda Red system in conjunction with FLP-FRT recombination to remove the desired genomic regions. Confirmation of gene deletions was determined by PCR.

Fed-Batch Cultivation

To start a fermentation, a 3 L Applikon® bioreactor (Foster City, Calif.) was charged with 1 L of M9 salts, 1 ml silicone anti-foam, 10 g/l glucose, and ampicillin (150 µg/ml). The reactor was inoculated with 100 ml of culture grown for eight hours in M9 medium. Prior to inoculation, culture broth was centrifuged and resuspended in fresh medium. During growth, adjustments in oxygen delivery and agitation rate were made as necessary to ensure that the dissolved oxygen concentration did not drop below 35%. The pH was maintained at approximately 6.8 during the cultivation by adding 7M NH₄OH as needed, and the temperature was maintained at 37° C. using a heating jacket and cooling loop. An exponential feeding profile of glucose (500 g/l) was based on that of a collaborator (Mckinzie Fruchtl), originally proposed by Korz et al. (1995) *Journal of Biotechnology* 39(1):59-65 and Lee et al. (1996) *Trends in Biotechnology* 14(3):98-105.

At the end of the fermentation process, cells were harvested via centrifugation at 12,000×g for 30 minutes at 5° C. (Beckman Coulter Avanti, JLA-10.500 fixed angle rotor). Optical densities were monitored using a Bugeye optical density probe (BugLab, Foster City, Calif.), providing a measurement of arbitrary growth units, and a DU800 Beckman Coulter spectrophotometer (Brea, Calif.), providing growth measurements as $OD_{600}$.

Lysate Preparation

A 50 g cell pellet was re-suspended in 150 ml of 25 mM Tris buffer, pH 7, 1 mM phenylmethylsulphonyl fluoride (PMSF), 20 μg/ml aprotinin, and 1 mM ethylenediaminetetraacetic acid (EDTA), sonicated, and clarified by centrifugation at 50,000×g for 30 minutes followed by filtration through a 0.45 μm SUPOR® membrane to produce the lysate applied to the column.

Column Capacity Measurements

Chromatography was performed using an ÄKTA FPLC. Diethylaminoethyl cellulose (DEAE) was selected as the ion exchange (IEX) resin due to its prevalence of use in manufacturing; specifically, the column used was a 1 ml HiTrap DEAE FF from GE (Piscataway, N.J.). 25 mM Tris buffer, pH 7, was selected for all of the FPLC purification steps. The loading buffer contained 10 mM NaCl to minimize non-specific binding (Buffer A). The elution buffer contained 2M NaCl, which is sufficient to desorb bound proteins (Buffer B). The flowrate for all FPLC experiments was set to 1 ml/min Prior to loading the column with lysate, the system was washed with 10 column volumes (CVs) Buffer A. The column was loaded at 10% breakthrough, and then washed with 10 column volumes (CV) of Buffer A to remove any unbound proteins.

Reductions in the amount of HCPs that natively bind were measured by determining the percent of proteins that bound to DEAE under various loading conditions. This was accomplished by applying 40 mg of total protein to the column under binding conditions while collecting the flow through. The binding conditions used were 25 mM Tris, pH 7, at salt concentrations of 5 mM, 100 mM, and 250 mM NaCl. The bound proteins were then eluted using 2M NaCl and the peak was collected. Three runs were completed at each salt concentration to verify data. A BioRad DC™ Protein assay was used to determine the total protein in each collected fraction and thus determine the percent protein bound and unbound.

Results and Discussion

To construct an *E. coli* cell line that has a reduced set of HCPs associated with DEAE ion exchange chromatography, we analyzed the DEAE separatome database, developed in Example 2, using the Importance Score (IS) equation (Equation 3).

$$\text{importance}_i = \sum_j \left[ b_1 \left( \frac{y_{cj}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_j \quad \text{Equation 3}$$

The IS provides the ability to quickly interpret chromatography data and rank HCPs to indicate their effect on column capacity. Candidate genes for knockout, etc., can be selected based on the IS and data on essentiality to avoid lethality. While the IS ranked all 784 proteins identified in the DEAE separatome, the top six genes that are not considered essential, i.e., rfaD, usg, rraA, cutA, nagD, and speA, were deleted in the initial prototype host cell of this example.

The high priority genes in Table 14 are listed in descending rank order, from greater importance to lesser importance, according to their importance score as calculated using Equation 3. The summation included NaCl fractions 60 mM, 109 mM, 159 mM, 208 mM, 258 mM, 307 mM, 357 mM, 406 mM, 456 mM, 505 mM, 1000 mM. $b_1=1$ for all genes regardless of essentiality, $y_{max}=1000$ mM. For $h_{i,j}$, $h_{i,total}$, and $h_{j,total}$, mass spectroscopy data were used to determine the amount of protein, which was defined as the number of confident sequencing events that matched to peptides associated with a given protein ($h_i$). MWref=170 kDa (the molecular weight of the largest gene product, mukB); $\alpha=1$.

The top 50 genes in the IS ranking for purposes of this example are shown in Table 14:

TABLE 14 rfaD
usg
rraA
rpoB
rpoC
tufA
cutA
ptsI
nagD
ycfD
speA
gldA
glnA
metE
tgt
argG
groL
prs
typA
fusA
entF
hemL
ycaO
slyD
gatZ
ilvB
glgP
nusA
metH
gdhA
entB
prmB
rho
uvrB
infB
mukB
ilvA
metA
hslO
ppsA
recC
rnt
thiI
ybiT
clpB
iscS
metL
degP
rapA
purL This table lists genes ordered by decreasing importance as determined from the importance equation. While only six genes were removed from the wild type E. coli MG1655 parent cell in this experiment to produce the improved host cell LTSF06, continuing to delete, modify, or inhibit the expression of genes (while skipping or modifying genes considered to be essential) by moving down the list would continue to reduce the total number of HCPs present in the modified host cell and thus improve E. coli host cells for expression of recombinant peptides, polypeptides, and proteins by improving total column capacity.

Figure 14:
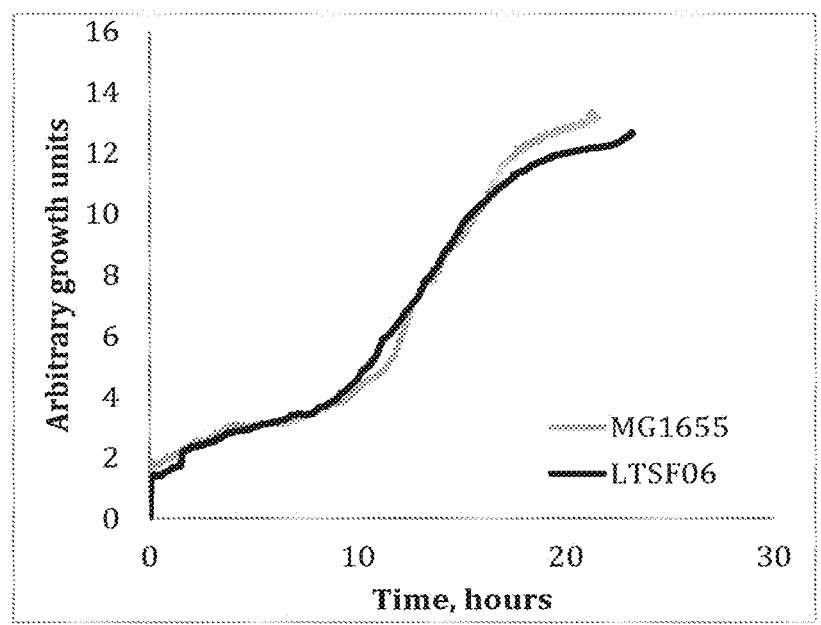
FIG. 14 shows the growth rates of parent E. coli strain MG1655 and knockout strain LTSF06 in Example 3.

Fed-batch culture of LTSF06 demonstrated that growth of this knockout strain was not compromised, as similar trajectories of growth units versus elapsed fermentation time were obtained for the parent (MG1655) and mutant strain (LTSF06) (FIG. 14).

Figure 15:
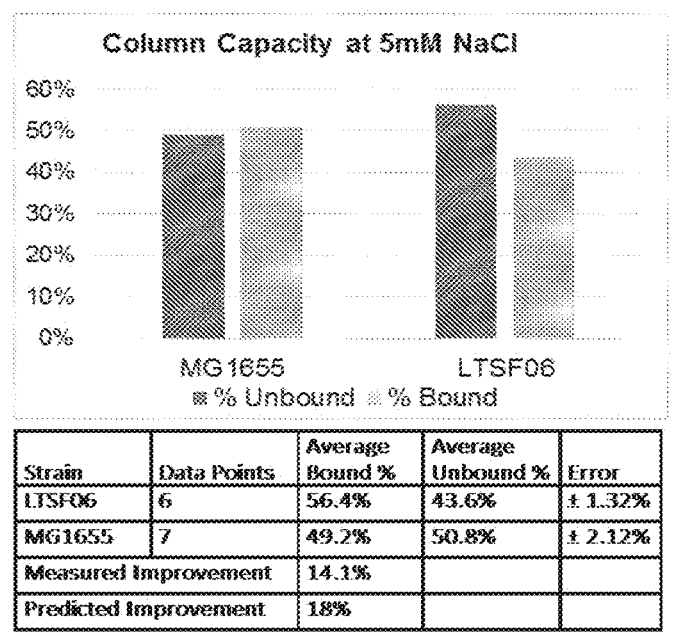
FIG. 15 shows the amount of proteins in parent E. coli strain MG1655 and knockout strain LTSF06 bound to DEAE at 5 mM NaCl (Example 3).
Figure 16:
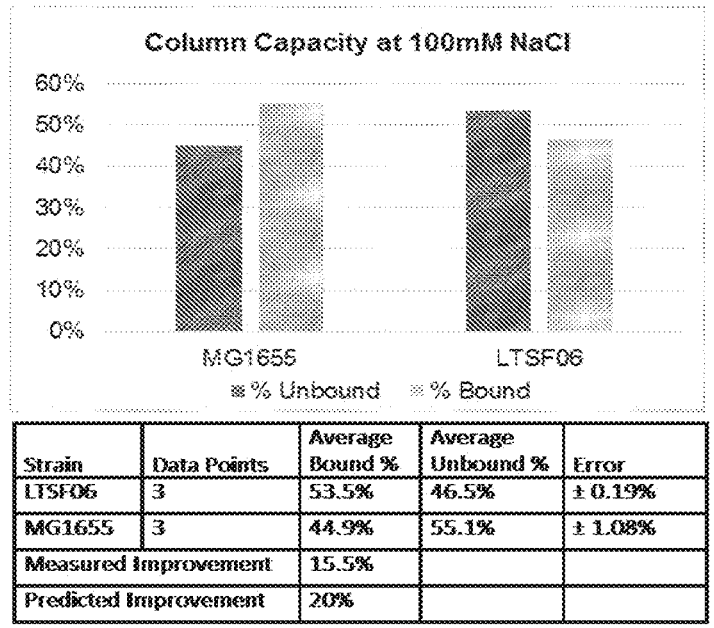
FIG. 16 shows the amount of proteins in parent E. coli strain MG1655 and knockout strain LTSF06 bound to DEAE at 100 mM NaCl (Example 3).
Figure 17:
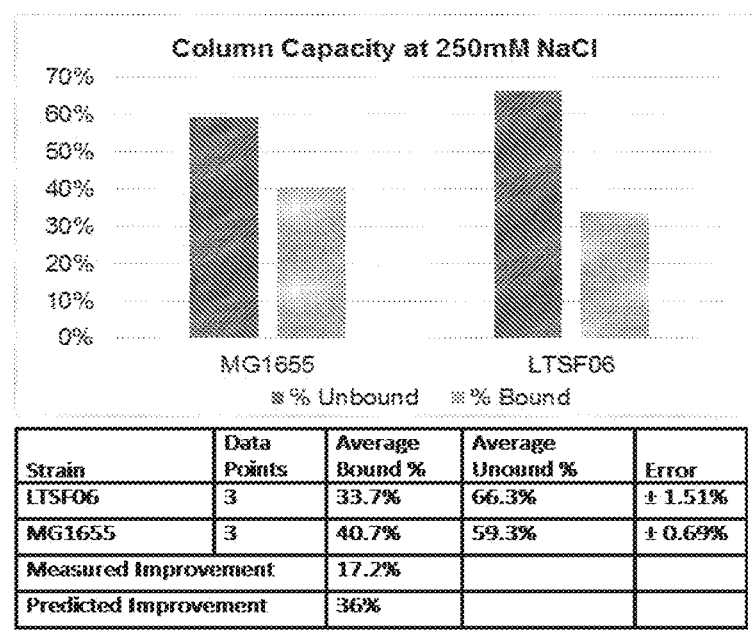
FIG. 17 shows the amount of proteins in parent E. coli strain MG1655 and knockout strain LTSF06 bound to DEAE at 250 mM NaCl (Example 3).

Lysates of LTSF06 and MG1655 were prepared and loaded to DEAE columns to determine the total amount of HCPs bound in each case. FIGS. 15, 16, and 17 show comparisons of the HCPs bound to DEAE that differ in the amount of NaCl present in the binding buffer, i.e., loading buffer containing 5 mM NaCl to minimize non-specific binding. Adding NaCl to the running buffer used to equilibrate the column and to the injected lysate is common practice to attenuate the column behavior of both HCPs and potential target protein, so a range of salt concentrations was examined and included in both low and stringent values. In all cases as shown in FIGS. 15, 16, and 17, there is a favorable difference in the amount of HCPs bound to the DEAE between the LTSF06 knockout strain compared to control parent E. coli strain MG1655. The reduction in HCPs in knockout strain LTSF06 varied between 14% to 17%.

These data demonstrate that the small number of deletions (six) contained in LTSF06, i.e., removal of only 0.119% of the total genome, significantly decreased the total amount of HCPs that would be encountered during target recombinant protein isolation via ion exchange chromatography.

These results demonstrate that the present separatome concept employing the importance equation provides a novel quantitative and rational means of identifying and ranking host cell proteins that negatively impact chromatographic separation capacity, and therefore chromatographic selectivity and purity of the final recovered target product. Once identified and ranked in this way, such host cell chromatography nuisance proteins can be deleted, modified, or inhibited to produce optimized host cells for recombinant expression of a broad spectrum of target peptides, polypeptides, and proteins, where such cells will still maintain good (or possibly even improved) fermentation characteristics such as growth rates, viability, capacity for expression, etc.

Extrapolating from the results obtained via the six gene deletions in LTSF06, it is reasonable to predict and fully expected that gene combinations containing increased numbers of genes, e.g., 7, 8, 9, 10, and so on similarly up to 50, can be selected from Table 14 for deletion, modification, and/or inhibition of expression in order to produce improved E. coli host cells for expression of recombinant peptides, polypeptides, and proteins. In addition to deletion, etc., of sequential (contiguous) combinations of high ranking genes listed in Table 14, deletions, etc., of non-sequential and non-contiguous combinations (which involve "skipping" (omitting) listed genes), and random combinations of high ranking genes in this table are also encompassed herein. Essential genes that can be modified by the methods discussed below can also be included in any of these gene combinations when necessary.

A consideration in designing such combinations involves gene essentiality. Essential genes can be deleted, etc., if the modified host cells exhibit acceptable viability, growth rates, protein expression levels, etc., for the intended application. Alternatively, essential genes can be modified, for example, by reducing their expression by replacing their naturally occurring promoters with weaker promoters, introducing strategic point mutations to replace amino acids involved in resin binding while still maintaining satisfactory levels of gene/protein activity, or replacing endogenous E. coli genes with genes from other organisms that perform the same or similar functions and that do not significantly adversely affect chromatographic separation efficiency and separation capacity, or cell growth, viability, and capacity for expression, rather than deleting them entirely. Such replacement genes include heterologs, homologs, analogs, paralogs, orthologs, and xenologs. These strategies facilitate improvements in chromatographic separation efficiency even when interfering host cell proteins include essential genes. In addition, as discussed above in the definition of "essential genes", various feeding strategies can be used in the present host cells and methods to circumvent potentially deleterious effects due to deletion, etc., of essential genes that would otherwise adversely impact chromatographic separation efficiency if present.

In addition to sequential and non-sequential, and contiguous and non-contiguous, deletions of genes listed in Table 14, calculation and identification of combinations of genes useful in the E. coli host cells and methods disclosed herein as mathematically described in Example 2 are equally applicable to the list of genes disclosed in Table 14 in this example. That mathematical description and accompanying discussion, including equations 6 and 7, are herein incorporated by reference in their entirety and applied herein.

The effectiveness of any of the various possible combinations of genes targeted for deletion, etc., selected from Table 14 in improving chromatographic separation efficiency of target host cell or target recombinant peptides, polypeptides, and proteins as described above can be determined without undue experimentation by the methods disclosed herein.

In summary, the data presented in this example demonstrate that the separatome concept, including importance equation 3, facilitates reduction in HCPs encountered during bioprocessing, improving column capacity and overall chromatographic separation efficiency, without adversely impacting host cell growth, viability, or capacity for expression, and that this can be achieved in a rational, stepwise predictable way. Results with LTSF06 show that with strategic deletions, significant improvement in column efficiency can be achieved. Identification and ordering of high ranking genes as determined from the importance equation out of the thousands of genes in the E. coli genome facilitates maximum improvements in E. coli host cells used for expression of a wide range of recombinant products without having to engineer individual host cells for specific targets. While other investigations have considered knockout or mutation to improve the purity of a single recombinant product, the mathematical framework disclosed herein guided minimal changes made to the E. coli genome that are useful regardless of target recombinant product. These minimal but strategic changes positively affect the initial chromatographic capture step, identified as a key bottleneck by polling several biotherapeutic and enzyme manufacturers.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of purifying a target peptide, polypeptide, or protein, comprising the steps of:
   1) recombinantly or non-recombinantly expressing said target peptide, polypeptide, or protein in *E. coli* wherein a combination of genes selected from the group consisting of the following combinations of genes is deleted:

ΔhldDΔusgΔrraA;
   ΔhldDΔusgΔrraAΔcutA;
   ΔhldDΔusgΔrraAΔcutAΔnagD;
   ΔhldDΔusgΔrraAΔcutAΔnagDΔspeA;
   ΔhldDΔusgΔrraAΔcutAΔnagDΔspeAΔgldA;
   ΔhldDΔusgΔrraAΔcutAΔnagDΔspeAΔgldAΔglnA;
   ΔhldDΔusgΔrraAΔcutAΔnagDΔspeAΔgldAΔglnAΔmetE;
   ΔhldDΔusgΔrraAΔcutAΔnagDΔspeAΔgldAΔglnAΔmetEΔtgt;
   ΔhldDΔusgΔrraAΔcutAΔnagDΔspeAΔgldAΔglnAΔmetEΔtgtΔargG;
   ΔhldDΔusgΔrraAΔcutAΔnagDΔspeAΔgldAΔglnAΔmetEΔtgtΔargGΔtypA;
   ΔhldDΔusgΔrraAΔcutAΔnagDΔspeAΔgldAΔglnAΔmetEΔtgtΔargGΔtypAΔentF;
   ΔhldDΔusgΔrraAΔcutAΔnagDΔspeAΔgldAΔglnAΔmetEΔtgtΔargGΔtypAΔentFΔycaO;
   ΔhldDΔusgΔrraAΔcutAΔnagDΔspeAΔgldAΔglnAΔmetEΔtgtΔargGΔtypAΔentFΔycaOΔslyD;
   ΔhldDΔusgΔrraAΔcutAΔnagDΔspeAΔgldAΔglnAΔmetEΔtgtΔargGΔtypAΔentFΔycaOΔslyDΔgatZ;
   ΔhldDΔusgΔrraAΔcutAΔnagDΔspeAΔgldAΔglnAΔmetEΔtgtΔargGΔtypAΔentFΔycaOΔslyDΔgatZΔilvB;
   ΔhldDΔusgΔrraAΔcutAΔnagDΔspeAΔgldAΔglnAΔmetEΔtgtΔargGΔtypAΔentFΔycaOΔslyDΔgatZΔilvBΔglgP;
   ΔhldDΔusgΔrraAΔcutAΔnagDΔspeAΔgldAΔglnAΔmetEΔtgtΔargGΔtypAΔentFΔycaOΔslyDΔgatZΔilvBΔglgPΔnusA; and
   ΔhldDΔusgΔrraAΔcutAΔnagDΔspeAΔgldAΔglnAΔmetEΔtgtΔargGΔtypAΔentFΔycaOΔslyDΔgatZΔilvBΔglgPΔnusAΔmetH;

2) in the case where said expressed target peptide, polypeptide, or protein is not secreted from said *E. coli*, preparing a lysate of said *E. coli* containing said expressed target peptide, polypeptide, or protein, producing an initial expressed target peptide-, polypeptide-, or protein-containing mixture; or
3) in the case where said expressed target peptide, polypeptide, or protein is secreted from said *E. coli*, harvesting culture medium in which said *E. coli* is grown, containing said expressed target peptide, polypeptide, or protein, thereby obtaining an initial expressed target peptide-, polypeptide-, or protein-containing mixture;
4) chromatographing said initial expressed target peptide-, polypeptide-, or protein-containing mixture of step 2) or step 3) using an affinity chromatography column comprising an affinity ligand bound to a solid phase, or an adsorption-based, non-affinity chromatography medium-containing column, and collecting elution fractions, thereby obtaining one or more fractions containing an enriched amount of said expressed target peptide, polypeptide, or protein relative to other peptides, polypeptides, or proteins in said fraction compared to the amount of said expressed target peptide, polypeptide, or protein relative to other peptides, polypeptides, or proteins in said initial expressed target peptide-, polypeptide-, or protein-containing mixture; and
5) further chromatographing an enriched fraction of step 4) to obtain said expressed target peptide, polypeptide, or protein in a desired degree of purity.

2. The method of claim 1, further comprising recovering purified expressed target peptide, polypeptide, or protein.

3. The method of claim 1, where said adsorption-based, non-affinity chromatography column is an ion exchange chromatography column.

4. The method of claim 1, wherein said recombinantly expressed target peptide, polypeptide, or protein is an endogenous peptide, polypeptide, or protein of said *E. coli*, or a heterologous peptide, polypeptide, or protein.

5. The method of claim 4, wherein:
said recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed heterologous peptide, polypeptide, or protein is selected from the group consisting of an enzyme, a therapeutic peptide, a therapeutic polypeptide, and a therapeutic protein.

6. The method of claim 5, wherein:
said recombinantly expressed heterologous enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, lung surfactant protein, serum albumin, tissue plasminogen activator, and tumor necrosis factor.

7. The method of claim 6, wherein said recombinantly expressed therapeutic enzyme is selected from the group consisting of $\alpha_1$-Antitrypsin, deoxyribonuclease, and superoxide dismutase.

8. The method of claim 1, wherein said non-recombinantly expressed peptide, polypeptide, or protein is an endogenous peptide, polypeptide, or protein of said *E. coli*.

9. The method of claim 8, wherein said non-recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

10. A method of enriching the amount of a target peptide, polypeptide, or protein relative to other peptides, polypeptides, or proteins present in an initial protein mixture comprising said target peptide, polypeptide, or protein, comprising the steps of:
1) recombinantly or non-recombinantly expressing said target peptide, polypeptide, or protein in *E. coli* wherein a combination of genes selected from the group consisting of the following combinations of genes is deleted:
ΔhldDΔusgΔrraA;
ΔhldDΔusgΔrraAΔcutA;
ΔhldDΔusgΔrraAΔcutAΔnagD;
ΔhldDΔusgΔrraAΔcutAΔnagDΔspeA;
ΔhldDΔusgΔrraAΔcutAΔnagDΔspeAΔgldA;
ΔhldDΔusgΔrraAΔcutAΔnagDΔspeAΔgldAΔglnA;
ΔhldDΔusgΔrraAΔcutAΔnagDΔspeAΔgldAΔglnAΔmetE;
ΔhldDΔusgΔrraAΔcutAΔnagDΔspeAΔgldAΔglnAΔmetEΔtgt;
ΔhldDΔusgΔrraAΔcutAΔnagDΔspeAΔgldAΔglnAΔmetEΔtgtΔargG;
ΔhldDΔusgΔrraAΔcutAΔnagDΔspeAΔgldAΔglnAΔmetEΔtgtΔargGΔtypA;
ΔhldDΔusgΔrraAΔcutAΔnagDΔspeAΔgldAΔglnAΔmetEΔtgtΔargGΔtypAΔentF;
ΔhldDΔusgΔrraAΔcutAΔnagDΔspeAΔgldAΔglnAΔmetEΔtgtΔargGΔtypAΔentFΔycaO;
ΔhldDΔusgΔrraAΔcutAΔnagDΔspeAΔgldAΔglnAΔmetEΔtgtΔargGΔtypAΔentFΔycaOΔslyD;
ΔhldDΔusgΔrraAΔcutAΔnagDΔspeAΔgldAΔglnAΔmetEΔtgtΔargGΔtypAΔentFΔycaOΔslyDΔgat Z;
ΔhldDΔusgΔrraAΔcutAΔnagDΔspeAΔgldAΔglnAΔmetEΔtgtΔargGΔtypAΔentFΔycaOΔslyDΔgat ZΔilvB;
ΔhldDΔusgΔrraAΔcutAΔnagDΔspeAΔgldAΔglnAΔmetEΔtgtΔargGΔtypAΔentFΔycaOΔslyDΔgat ZΔilvBΔglgP;
ΔhldDΔusgΔrraAΔcutAΔnagDΔspeAΔgldAΔglnAΔmetEΔtgtΔargGΔtypAΔentFΔycaOΔslyDΔgat ZΔilvBΔglgPΔnusA; and
ΔhldDΔusgΔrraAΔcutAΔnagDΔspeAΔgldAΔglnAΔmetEΔtgtΔargGΔtypAΔentFΔycaOΔslyDΔgat ZΔilvBΔglgPΔnusAΔmetH;
2) in the case where said expressed target peptide, polypeptide, or protein is not secreted from said *E. coli*, preparing a lysate of said *E. coli* containing said expressed target peptide, polypeptide, or protein, producing an initial expressed target peptide-, polypeptide-, or protein-containing mixture; or
3) in the case where said expressed target peptide, polypeptide, or protein is secreted from said *E. coli*, harvesting culture medium in which said *E. coli* is grown, containing said expressed target peptide, polypeptide, or protein, thereby obtaining an initial expressed target peptide-, polypeptide-, or protein-containing mixture;
4) chromatographing said initial expressed target peptide-, polypeptide-, or protein-containing mixture of step 2) or step 3) using an affinity chromatography column comprising an affinity ligand bound to a solid phase, or an adsorption-based, non-affinity chromatography medium-containing column, and collecting elution fractions, thereby obtaining one or more fractions containing an enriched amount of said expressed target peptide, polypeptide, or protein relative to other peptides, polypeptides, or proteins in said fraction compared to the amount of said expressed target peptide, polypeptide, or protein relative to other peptides, polypeptides, or proteins in said initial expressed target peptide-, polypeptide-, or protein-containing mixture.

11. The method of claim 10, further comprising chromatographing an enriched fraction of step 4) to obtain said expressed target peptide, polypeptide, or protein in a desired degree of purity.

12. The method of claim 11, further comprising recovering said expressed target peptide, polypeptide, or protein.

13. The method of claim 10, wherein said adsorption-based, non-affinity chromatography column is an ion exchange chromatography column.

14. The method of claim 10, wherein said recombinantly expressed target peptide, polypeptide, or protein is an endogenous peptide, polypeptide, or protein of said *E. coli*, or a heterologous peptide, polypeptide, or protein.

15. The method of claim 14, wherein:
said recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed heterologous peptide, polypeptide, or protein is selected from the group consisting of an enzyme, a therapeutic peptide, a therapeutic polypeptide, and a therapeutic protein.

16. The method of claim 15, wherein:
said recombinantly expressed heterologous enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, lung surfactant protein, serum albumin, tissue plasminogen activator, and tumor necrosis factor.

17. The method of claim 16, wherein said recombinantly expressed therapeutic enzyme is selected from the group consisting of $\alpha_1$-Antitrypsin, deoxyribonuclease, and superoxide dismutase.

18. The method of claim 10, wherein said non-recombinantly expressed peptide, polypeptide, or protein is an endogenous peptide, polypeptide, or protein of said *E. coli*.

19. The method of claim 18, wherein said non-recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

* * * * *

SEQUENCE LISTING

<160> NUMBER OF SEQ ID NOS: 53

<210> SEQ ID NO 1
<211> LENGTH: 6
<212> TYPE: PRT
<213> ORGANISM: Artificial Sequence
<220> FEATURE:
<223> OTHER INFORMATION: Primer

<400> SEQUENCE: 1

His His His His His His
1               5

<210> SEQ ID NO 2
<211> LENGTH: 52
<212> TYPE: DNA
<213> ORGANISM: Artificial Sequence
<220> FEATURE:
<223> OTHER INFORMATION: Primer

<400> SEQUENCE: 2
gccaagcttg tggcatcatc atccgcatat gagtaaagga gaagaacttt tc          52

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ttggaattca ttatttgtag agct                                         24

<210> SEQ ID NO 4
<211> LENGTH: 120
<212> TYPE: DNA
<213> ORGANISM: Escherichia coli

<400> SEQUENCE: 4
gcaaaatttc gggaaggcgt ctcgaagaat ttaacggagg gtaaaaaaac cgacgcacac    60
gtgttgctgt gggctgcgac gatatgccca gaccatcatg atcacacccg cgacaatcat   120

<210> SEQ ID NO 5
<211> LENGTH: 98
<212> TYPE: DNA
<213> ORGANISM: Escherichia coli

<400> SEQUENCE: 5
tttgttgaat ttttattaaa tctgggttga gcgtgtcggg agcaagtgct ggggtatgac    60
gcggactgat tcacaaatct gtcactttc cttacaac                             98

<210> SEQ ID NO 6
<211> LENGTH: 96
<212> TYPE: DNA
<213> ORGANISM: Escherichia coli

<400> SEQUENCE: 6
ggcgtactct gacaccgacg aattttaccc agttgcagga ggcacacgcg caacgctaaa    60
caggtaaatt aatattattt ataaacccat aattac                              96

<210> SEQ ID NO 7
<211> LENGTH: 97
<212> TYPE: DNA

<213> ORGANISM: Escherichia coli

<400> SEQUENCE: 7

| cgctggttta aaacgttgga ctgttttttct gacgtagtgg agaaaaacca cctttgaacg | 60 |
| ttgattaata ttaataatga gggaaattta atgagct | 97 |

<210> SEQ ID NO 8
<211> LENGTH: 97
<212> TYPE: DNA
<213> ORGANISM: Escherichia coli

<400> SEQUENCE: 8

| gtggagtgac gaaaatcttc atcagagatg acaacggagg aaccgagaag aaaaaagtgg | 60 |
| cagagtgatc aataccctct ttaaaagaag agggtta | 97 |

<210> SEQ ID NO 9
<211> LENGTH: 97
<212> TYPE: DNA
<213> ORGANISM: Escherichia coli

<400> SEQUENCE: 9

| taaaacccgt attattgcgc gctttccgta cgactaaagt gattttcgca gcattctggg | 60 |
| caaaataaaa tcaaatagcc tacgcaatgt aggctta | 97 |

<210> SEQ ID NO 10
<211> LENGTH: 98
<212> TYPE: DNA
<213> ORGANISM: Escherichia coli

<400> SEQUENCE: 10

| gttgtaagga aaagtgacag atttgtgaat cagtccgcgt catacccag cacttgctcc | 60 |
| cgacacgctc aacccagatt taataaaaat tcaacaaa | 98 |

<210> SEQ ID NO 11
<211> LENGTH: 98
<212> TYPE: DNA
<213> ORGANISM: Escherichia coli

<400> SEQUENCE: 11

| tttgttgaat ttttattaaa tctgggttga gcgtgtcggg agcaagtgct ggggtatgac | 60 |
| gcggactgat tcacaaatct gtcactttc cttacaac | 98 |

<210> SEQ ID NO 12
<211> LENGTH: 96
<212> TYPE: DNA
<213> ORGANISM: Escherichia coli

<400> SEQUENCE: 12

| gtaattatgg gtttataaat aatattaatt tacctgttta gcgttgcgcg tgtgcctcct | 60 |
| gcaactgggt aaaattcgtc ggtgtcagag tacgcc | 96 |

<210> SEQ ID NO 13
<211> LENGTH: 96
<212> TYPE: DNA
<213> ORGANISM: Escherichia coli

<400> SEQUENCE: 13

| ggcgtactct gacaccgacg aattttaccc agttgcagga ggcacacgcg caacgctaaa | 60 |
| caggtaaatt aatattattt ataaacccat aattac | 96 |

<210> SEQ ID NO 14
<211> LENGTH: 97
<212> TYPE: DNA
<213> ORGANISM: Escherichia coli

<400> SEQUENCE: 14
agctcattaa atttccctca ttattaatat taatcaacgt tcaaaggtgg ttttctcca    60 ctacgtcaga aaacagtcc aacgttttaa accagcg                             97

<210> SEQ ID NO 15
<211> LENGTH: 97
<212> TYPE: DNA
<213> ORGANISM: Escherichia coli

<400> SEQUENCE: 15
cgctggttta aaacgttgga ctgttttct gacgtagtgg agaaaaacca cctttgaacg    60
ttgattaata ttaataatga gggaaattta atgagct                            97

<210> SEQ ID NO 16
<211> LENGTH: 97
<212> TYPE: DNA
<213> ORGANISM: Escherichia coli

<400> SEQUENCE: 16
taaccctctt cttttaaaga gggtattgat cactctgcca ctttttctt ctcggttcct    60 ccgttgtcat ctctgatgaa gattttcgtc actccac                            97

<210> SEQ ID NO 17
<211> LENGTH: 97
<212> TYPE: DNA
<213> ORGANISM: Escherichia coli

<400> SEQUENCE: 17
gtggagtgac gaaaatcttc atcagagatg acaacggagg aaccgagaag aaaaaagtgg   60
cagagtgatc aataccctct ttaaaagaag agggtta                            97

<210> SEQ ID NO 18
<211> LENGTH: 97
<212> TYPE: DNA
<213> ORGANISM: Escherichia coli

<400> SEQUENCE: 18
taagcctaca ttgcgtaggc tatttgattt tattttgccc agaatgctgc gaaaatcact   60
ttagtcgtac ggaaagcgcg caataatacg ggttta                             97

<210> SEQ ID NO 19
<211> LENGTH: 97
<212> TYPE: DNA
<213> ORGANISM: Escherichia coli

<400> SEQUENCE: 19
taaaacccgt attattgcgc gctttccgta cgactaaagt gattttcgca gcattctggg   60
caaaataaaa tcaaatagcc tacgcaatgt aggctta                            97

<210> SEQ ID NO 20
<211> LENGTH: 68
<212> TYPE: DNA
<213> ORGANISM: Artificial Sequence
<220> FEATURE:

<223> OTHER INFORMATION: Primer

<400> SEQUENCE: 20
tttgttgaat ttttattaaa tctgggttga gcgtgtcggg agcaagtgcg ccacccatca    60
cagcttta                                                             68

<210> SEQ ID NO 21
<211> LENGTH: 70
<212> TYPE: DNA
<213> ORGANISM: Artificial Sequence
<220> FEATURE:
<223> OTHER INFORMATION: Primer

<400> SEQUENCE: 21
gttgtaagga aaagtgacag atttgtgaat cagtccgcgt cataccccag gggaaggcgt    60
ctcgaagaat                                                           70

<210> SEQ ID NO 22
<211> LENGTH: 66
<212> TYPE: DNA
<213> ORGANISM: Artificial Sequence
<220> FEATURE:
<223> OTHER INFORMATION: Primer

<400> SEQUENCE: 22
ggcgtactct gacaccgacg aattttaccc agttgcagga ggcacacgcc acccatcaca    60
gcttta                                                               66

<210> SEQ ID NO 23
<211> LENGTH: 70
<212> TYPE: DNA
<213> ORGANISM: Artificial Sequence
<220> FEATURE:
<223> OTHER INFORMATION: Primer

<400> SEQUENCE: 23
gtaattatgg gtttataaat aatattaatt tacctgttta gcgttgcgcg gggaaggcgt    60
ctcgaagaat                                                           70

<210> SEQ ID NO 24
<211> LENGTH: 67
<212> TYPE: DNA
<213> ORGANISM: Artificial Sequence
<220> FEATURE:
<223> OTHER INFORMATION: Primer

<400> SEQUENCE: 24
cgctggttta aaacgttgga ctgttttct gacgtagtgg agaaaaacgc cacccatcac     60
agcttta                                                              67

<210> SEQ ID NO 25
<211> LENGTH: 70
<212> TYPE: DNA
<213> ORGANISM: Artificial Sequence
<220> FEATURE:
<223> OTHER INFORMATION: Primer

<400> SEQUENCE: 25
agctcattaa atttccctca ttattaatat taatcaacgt tcaaaggtgg gggaaggcgt    60
ctcgaagaat                                                           70

```
<210> SEQ ID NO 26
<211> LENGTH: 67
<212> TYPE: DNA
<213> ORGANISM: Artificial Sequence
<220> FEATURE:
<223> OTHER INFORMATION: Primer

<400> SEQUENCE: 26
gtggagtgac gaaaatcttc atcagagatg acaacggagg aaccgagcgc cacccatcac    60
agcttta                                                              67

<210> SEQ ID NO 27
<211> LENGTH: 70
<212> TYPE: DNA
<213> ORGANISM: Artificial Sequence
<220> FEATURE:
<223> OTHER INFORMATION: Primer

<400> SEQUENCE: 27
taaccctctt cttttaaaga gggtattgat cactctgcca ctttttttctt gggaaggcgt   60 ctcgaagaat                                                           70

<210> SEQ ID NO 28
<211> LENGTH: 67
<212> TYPE: DNA
<213> ORGANISM: Artificial Sequence
<220> FEATURE:
<223> OTHER INFORMATION: Primer

<400> SEQUENCE: 28 taaaaccgt attattgcgc gctttccgta cgactaaagt gattttccgc cacccatcac     60
agcttta                                                              67

<210> SEQ ID NO 29
<211> LENGTH: 70
<212> TYPE: DNA
<213> ORGANISM: Artificial Sequence
<220> FEATURE:
<223> OTHER INFORMATION: Primer

<400> SEQUENCE: 29
taagcctaca ttgcgtaggc tatttgattt tattttgccc agaatgctgc gggaaggcgt    60
ctcgaagaat                                                           70

<210> SEQ ID NO 30
<211> LENGTH: 70
<212> TYPE: DNA
<213> ORGANISM: Artificial Sequence
<220> FEATURE:
<223> OTHER INFORMATION: Primer

<400> SEQUENCE: 30
gcaaaaccaa catccgccat gaaggactag ctaaaaccca aactagtttg gtgtaggctg    60
gagctgcttc                                                           70

<210> SEQ ID NO 31
<211> LENGTH: 70
<212> TYPE: DNA
<213> ORGANISM: Artificial Sequence
<220> FEATURE:
<223> OTHER INFORMATION: Primer

<400> SEQUENCE: 31
```

```
ccggtgccat cacatcgatt atcgcctggg gatagcgcgc ctggagcgtg atgggaatta    60
gccatggtcc                                                          70

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gcaaaaccaa catccgccat                                               20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ccggtgccat cacatcgatt a                                             21

<210> SEQ ID NO 34
<211> LENGTH: 70
<212> TYPE: DNA
<213> ORGANISM: Artificial Sequence
<220> FEATURE:
<223> OTHER INFORMATION: Primer

<400> SEQUENCE: 34
cggcatcatt gctgtgtaaa ctgggtttta acgccgttca tcatccggca gtgtaggctg    60
gagctgcttc                                                          70

<210> SEQ ID NO 35
<211> LENGTH: 70
<212> TYPE: DNA
<213> ORGANISM: Artificial Sequence
<220> FEATURE:
<223> OTHER INFORMATION: Primer

<400> SEQUENCE: 35
gaagacggtg atgggttcgt tcgccacctg ggagagcgcc ttttccagct atgggaatta    60
gccatggtcc                                                          70

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gcggcatcat tgctgtgtaa                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gaagacggtg atgggttcgt                                               20
```

```
<210> SEQ ID NO 38
<211> LENGTH: 70
<212> TYPE: DNA
<213> ORGANISM: Artificial Sequence
<220> FEATURE:
<223> OTHER INFORMATION: Primer

<400> SEQUENCE: 38
cgtactgtca agggagcgtt actgactaac ctgctgtttg ttttagggat gtgtaggctg      60
gagctgcttc                                                            70

<210> SEQ ID NO 39
<211> LENGTH: 70
<212> TYPE: DNA
<213> ORGANISM: Artificial Sequence
<220> FEATURE:
<223> OTHER INFORMATION: Primer

<400> SEQUENCE: 39
gagctggagc gtgagaacaa ccatctgaaa gaacagcaga acggctggca atgggaatta      60
gccatggtcc                                                            70

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
cgtactgtca agggagcgtt                                                  20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
aagagctgga gcgtgagaac                                                  20

<210> SEQ ID NO 42
<211> LENGTH: 70
<212> TYPE: DNA
<213> ORGANISM: Artificial Sequence
<220> FEATURE:
<223> OTHER INFORMATION: Primer

<400> SEQUENCE: 42
cgactaacat ccttcccccg tccgttgtat agtgacctct ctcttgcggt gtgtaggctg      60
gagctgcttc                                                            70

<210> SEQ ID NO 43
<211> LENGTH: 70
<212> TYPE: DNA
<213> ORGANISM: Artificial Sequence
<220> FEATURE:
<223> OTHER INFORMATION: Primer

<400> SEQUENCE: 43
aaagcaaagg cttgatccgc ggggacaaat tgtgaacgtc ccggcgcgtc atgggaatta      60
```
gccatggtcc                                                              70

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
cgactaacat ccttcccccg                                                   20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
aaagcaaagg cttgatccgc                                                   20

<210> SEQ ID NO 46
<211> LENGTH: 70
<212> TYPE: DNA
<213> ORGANISM: Artificial Sequence
<220> FEATURE:
<223> OTHER INFORMATION: Primer

<400> SEQUENCE: 46
ttggagcgtc agcattcact gctggaaaat ccatgtgctt atgggttgtt gtgtaggctg        60
gagctgcttc                                                              70

<210> SEQ ID NO 47
<211> LENGTH: 70
<212> TYPE: DNA
<213> ORGANISM: Artificial Sequence
<220> FEATURE:
<223> OTHER INFORMATION: Primer

<400> SEQUENCE: 47
tattgcagga gctgcgtagg cctgataagc gtagcgcatc aggcagtttg atgggaatta        60
gccatggtcc                                                              70

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
cgtttcgcac taatctgccg                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tattgcagga gctgcgtagg                                                   20

```
<210> SEQ ID NO 50
<211> LENGTH: 70
<212> TYPE: DNA
<213> ORGANISM: Artificial Sequence
<220> FEATURE:
<223> OTHER INFORMATION: Primer

<400> SEQUENCE: 50
ttggagcgtc agcattcact gctggaaaat ccatgtgctt atgggttgtt gtgtaggctg      60
gagctgcttc                                                             70

<210> SEQ ID NO 51
<211> LENGTH: 70
<212> TYPE: DNA
<213> ORGANISM: Artificial Sequence
<220> FEATURE:
<223> OTHER INFORMATION: Primer

<400> SEQUENCE: 51
cgacgaggaa gggttggatt tgtcacaata aattgtggcg gattatcacc atgggaatta      60
gccatggtcc                                                             70

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
ttggagcgtc agcattcact                                                  20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
cgacgaggaa gggttggatt                                                  20
```